US008193123B2

(12) United States Patent
Rank et al.

(10) Patent No.: US 8,193,123 B2
(45) Date of Patent: Jun. 5, 2012

(54) ARTICLES HAVING LOCALIZED MOLECULES DISPOSED THEREON AND METHODS OF PRODUCING SAME

(75) Inventors: David R. Rank, Palo Alto, CA (US); Jeffery Wegener, Cupertino, CA (US); Jonas Korlach, Castro Valley, CA (US); Daniel Roitman, Menlo Park, CA (US); Yue Xu, Fremont, CA (US); John Lyle, Redwood Shores, CA (US); Stephen Turner, Menlo Park, CA (US); Paul Peluso, Hayward, CA (US); Geoff Otto, Santa Clara, CA (US); Ron Cicero, Palo Alto, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 869 days.

(21) Appl. No.: 11/978,171

(22) Filed: Oct. 26, 2007

(65) Prior Publication Data

US 2008/0176769 A1    Jul. 24, 2008

Related U.S. Application Data

(63) Continuation of application No. 11/731,748, filed on Mar. 29, 2007, which is a continuation-in-part of application No. 11/394,352, filed on Mar. 30, 2006.

(51) Int. Cl.
*C40B 99/00* (2006.01)
(52) U.S. Cl. .............. 506/43; 506/33; 506/32; 435/91.2
(58) Field of Classification Search .................. None
See application file for complete search history.

(56) References Cited

U.S. PATENT DOCUMENTS

| | | | |
|---|---|---|---|
| 5,001,050 A | 3/1991 | Blanco et al. | |
| 5,143,854 A | 9/1992 | Pirrung et al. | |
| 5,198,543 A | 3/1993 | Blanco et al. | |
| 5,412,087 A | 5/1995 | McGall et al. | |
| 5,547,839 A | 8/1996 | Dower et al. | |
| 5,576,204 A | 11/1996 | Blanco et al. | |
| 5,624,711 A | 4/1997 | Sundberg et al. | |
| 5,723,584 A | 3/1998 | Schatz | |
| 5,733,651 A | 3/1998 | Wank et al. | |
| 5,821,058 A | 10/1998 | Smith et al. | |
| 5,851,840 A * | 12/1998 | Sluka et al. ................... | 436/525 |
| 5,874,239 A | 2/1999 | Schatz | |
| 5,919,523 A | 7/1999 | Sundberg et al. | |
| 5,932,433 A | 8/1999 | Schatz | |
| 6,028,025 A | 2/2000 | Ying et al. | |
| 6,210,896 B1 | 4/2001 | Chan | |
| 6,235,488 B1 * | 5/2001 | Tom-Moy et al. ............. | 435/7.5 |
| 6,265,552 B1 | 7/2001 | Schatz | |
| 6,787,308 B2 | 9/2004 | Balasubramanian et al. | |
| 6,818,395 B1 | 11/2004 | Quake et al. | |
| 6,869,764 B2 | 3/2005 | Williams et al. | |
| 6,887,665 B2 | 5/2005 | Trulson et al. | |
| 6,917,726 B2 | 7/2005 | Levene et al. | |
| 6,982,146 B1 | 1/2006 | Schneider et al. | |
| 6,991,726 B2 | 1/2006 | St. Germain | |
| 7,013,054 B2 | 3/2006 | Levene et al. | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,170,050 B2 | 1/2007 | Turner et al. | |
| 7,302,146 B2 | 11/2007 | Turner et al. | |
| 7,315,019 B2 | 1/2008 | Turner et al. | |
| 7,476,503 B2 | 1/2009 | Turner et al. | |
| 7,763,423 B2 | 7/2010 | Roitman et al. | |
| 2002/0128234 A1 | 9/2002 | Hubbell et al. | |
| 2002/0137053 A1 | 9/2002 | Ault-Riche et al. | |
| 2003/0044781 A1 | 3/2003 | Korlach et al. | |
| 2003/0174992 A1 * | 9/2003 | Levene et al. ................. | 385/129 |
| 2003/0186276 A1 | 10/2003 | Odedra | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0048301 A1 | 3/2004 | Sood et al. | |
| 2004/0224319 A1 | 11/2004 | Sood et al. | |
| 2004/0234964 A1 * | 11/2004 | Cole et al. ........................ | 435/6 |
| 2005/0131219 A1 | 6/2005 | Urdea et al. | |
| 2005/0148027 A1 | 7/2005 | Pirrung et al. | |
| 2005/0208557 A1 | 9/2005 | Korlach et al. | |
| 2005/0233473 A1 | 10/2005 | Cicero et al. | |
| 2006/0177855 A1 | 8/2006 | Utermohlen et al. | |
| 2007/0036511 A1 | 2/2007 | Lundquist et al. | |
| 2007/0077564 A1 | 4/2007 | Roitman et al. | |
| 2007/0128133 A1 | 6/2007 | Eid et al. | |
| 2007/0196846 A1 | 8/2007 | Hanzel et al. | |
| 2008/0032301 A1 | 2/2008 | Rank et al. | |
| 2008/0176761 A1 | 7/2008 | Menchen et al. | |
| 2008/0176769 A1 | 7/2008 | Rank et al. | |
| 2009/0061429 A1 | 3/2009 | Roitman et al. | |
| 2010/0261158 A1 | 10/2010 | Nordman et al. | |

FOREIGN PATENT DOCUMENTS

| | | |
|---|---|---|
| EP | 1 105 529 B1 | 11/2005 |
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO/00/53805 * | 9/2000 |
| WO | WO 00/53805 A1 | 9/2000 |
| WO | WO 01/16375 A2 | 3/2001 |
| WO | WO 2004/017042 A2 | 2/2004 |
| WO | WO 2004/055160 A2 | 7/2004 |
| WO | WO 2005/084367 A2 | 9/2005 |
| WO | WO 2007/064597 A2 | 6/2007 |
| WO | WO 2007/075873 A2 | 7/2007 |

OTHER PUBLICATIONS

Kambhampati et al. (2001) "Novel silicon dioxide sol-gel films for potential sensor applications: a surface plasmon resonance study," Langmuir, 17:1169-1175.

(Continued)

*Primary Examiner* — Christopher M Gross
(74) *Attorney, Agent, or Firm* — Quine Intellectual Property Law Group, P.C.; Monicia Elrod-Erickson; Robert Reamey

(57) ABSTRACT

Methods of producing substrates having selected active chemical regions by employing elements of the substrates in assisting the localization of active chemical groups in desired regions of the substrate. The methods may include optical, chemical and/or mechanical processes for the deposition, removal, activation and/or deactivation of chemical groups in selected regions of the substrate to provide selective active regions of the substrate.

18 Claims, 24 Drawing Sheets

OTHER PUBLICATIONS

Osborn & Yager (1995) "Formation of planar solvent-free phospholipid bilayers by Langmuir-Blodgett transfer of monolayers to micromachined apertures in silicon," Langmuir, 11:8-12.

Bakiamoh and Blanchard (2001) "Surface second harmonic generation from asymmetric multilayer assemblies: gaining insight into layer-dependent order," Langmuir, 17:3438-3446.

Blonder et al. (1997) "Application of a Nitrospiropyran-FAD-Reconstituted Glucose Oxidase and Charged Electron Mediators as Optobioelectronic Assemblies for the Amperometric Transduction of Recorded Optical Signals: Control of the "On"—"Off" Direction of the Photoswitch," JACS, 119(49):11747-11757.

Blonder et al. (1997) "Development of Amperometric and Microgravimetric Immunosensors and Reversible Immunosensors Using Antigen and Photoisomerizable Antigen Monolayer Electrodes," JACS, 119(43):10467-10478.

Bruckbauer et al. (2004) "An addressable antibody nanoarray produced on a nanostructured surface," J. Am. Chem. Soc., 126(21):6508-6509.

Brukman et al. (2006) "Nanotribological properties of alkanephosphonic acid self-assembled monolayers on aluminum oxide: effects of fluorination and substrate crystallinity," Langmuir, 22(9):3988-3998.

Danelon et al. (2006) "Cell membranes suspended across nanoaperture arrays," Langmuir, 22(1):22-25.

Decher (1997) "Fuzzy, nanoassemblies: toward layered polymeric multicomposites," Science, 277:1232-1237.

Fore et al. (2007) "Pulsed-interleaved excitation FRET measurements on single duplex DNA molecules inside C-shaped nanoapertures," Nano Lett. 7(6):1749-1756.

Foster et al. (2006) "Friction force microscopy of alkylphosphonic acid and carboxylic acids adsorbed on the native oxide of aluminum," Langmuir, 22(22):9254-9259.

Gardner et al. (1995) "Systems for orthogonal self-assembly of electroactive monolayers on Au and ITO—an approach to molecular electronics," J. Am. Chem. Soc., 117(26):6927-6933.

Glatthar and Giese (2000) "A new photocleavable linker in solid-phase chemistry for ether cleavage," Org. Lett., 2(15):2315-2317.

Herrwerth et al. (2003) "Factors that determine the protein resistance of oligoether self-assembled monolayers—internal hydrophilicity, terminal hydrophilicity, and lateral packing density," J. Am. Chem. Soc., 125(31):9359-9366.

Hodneland and Mrksich (2000) "Biomolecular Surfaces that Release Ligands under Electrochemical Control," J. Am. Chem. Soc., 122(17):4235-4236.

Hofer et al. (2001) "Alkyl Phosphate Monolayers, Self-Assembled from Aqueous Solution onto Metal Oxide Surfaces," Langmuir, 17(13):4014-4020.

Huang et al. (2002) "Biotin-Derivatized Poly(L-lysine))-g-Poly(ethylene glycol): A Novel Polymeric Interface for Bioaffinity Sensing" Langmuir, 18(1): 220-230.

Kelley et al. (2003) "High-Performance OTFTs Using Surface-Modified Alumina Dielectrics," J. Phys. Chem. B, 107(24):5877-5881.

Libera et al. (2005) "Comparative X-ray standing wave analysis of metal-phosphonate multilayer films of dodecane and porphyrin molecular square," J. Phys. Chem. B 109(4):1441-1450.

Liu et al. (2004) "Biosensing based upon molecular confinement in metallic nanocavity arrays," Nanotechnology, 15:1368-1374.

Love et al. (2005) "Self-assembled monolayers of thiolates on metals as a form of nanotechnology," Chem. Rev. 105(4):1103-1169.

Messerschmidt and Schwartz (2001) Growth Mechanisms of Octadecylphosphonic Acid Self-Assembled Monolayers on Sapphire (Corundum): Evidence for a Quasi-equilibrium Triple Point, Langmuir, 17(2):462-467.

Michel et al. (2002) "A novel approach to produce biologically relevant chemical patterns at the nanometer scale: Selective molecular assembly patterning combined with colloidal lithography," Langmuir, 18(22):8580-8586.

Michel et al. (2002) "Selective molecular assembly patterning: A new approach to micro- and nanochemical patterning of surfaces for biological applications," Langmuir, 18(8):3281-3287.

Mutin et al. (2004) "Selective Surface Modification of $SiO_2$—$TiO_2$ Supports with Phosphonic Acids," Chemistry of Materials, 16(26):5670-5675.

Novotny et al. (1997) "Theory of Nanometric Optical Tweezers.," Phys. Rev. Letts. 79(4):645-648.

Pellerite et al. (2003) "Effects of Fluorination on Self-Assembled Monolayer Formation from Alkanephosphonic Acids on Aluminum: Kinetics and Structure," J. Phys. Chem. B, 107(42):11726-11736.

Raman et al. (2006) "Formation of self-assembled monolayers of alkylphosphonic acid on the native oxide surface of SS316L," Langmuir, 22(15):6469-6472.

Ramsier et al. (1988) "Adsorption of phosphorus-acids on alumina," Surface Science, 203(1-2):72-88.

Rodebaugh et al. (1997) "A new o-nitrobenzyl photocleavable linker for solid phase synthesis," Tetrahedron Lett., 38(44), 7653-7656.

Rossetti et al. (2005) "Interactions between titanium dioxide and phosphatidyl serine-containing liposomes: formation and patterning of supported phospholipid bilayers on the surface of a medically relevant material," Langmuir, 21(14):6443-6450.

Tosatti et al. (2002) "Self-Assembled Monolayers of Dodecyl and Hydroxy-dodecyl Phosphates on Both Smooth and Rough Titanium and Titanium Oxide Surfaces," Langmuir,18(9):3537-3548.

Voros et al. (2003) "Polymer Cushions to Analyze Genes and Proteins" BioWorld 2:16-17.

Xia and Whitesides (1996) "Shadowed sputtering of gold on V-shaped microtrenches etched in silicon and applications in microfabrication," Advanced Materials, 8(9):765-768.

Zoulalian et al. (2006) "Functionalization of titanium oxide surfaces by means of poly(alkyl-phosphonates)" J. Phys. Chem. B 110(51):25603-25605.

Zwahlen et al. (2002) "Orientation in Methyl- and Hydroxyl-Terminated Self-Assembled Alkanephosphate Monolayers on Titanium Oxide Surfaces Investigated with Soft X-ray Absorption," Langmuir, 18(10):3957-3962.

M.J. Levene et al. (Jan. 31, 2003) "Zero-Mode Waveguides for Single-Molecule Analysis at High Concentrations," *Science*, 299: 682-686.

Office Action dated Mar. 29, 2011 from related AU application No. 2006299641.

Office Action dated May 11, 2010 from corresponding CN application No. 200780012053.3.

Office Action dated Nov. 4, 2010 from corresponding CN application No. 200780012053.3.

Office Action dated Apr. 25, 2011 from corresponding CN application No. 200780012053.3.

Cha et al. (2004) "Immobilization of oriented protein molecules on poly(ethylene glycol)-coated Si(111)," Proteomics, 4(7):1965-1976.

Ruiz-Taylor et al. (2001) "Monolayers of derivatized poly(L-lysine)-grafted poly(ethylene glycol) on metal oxides as a class of biomolecular interfaces," PNAS, 98(3)852-857.

Sofia et al. (1998) "Poly(ethylene oxide) grafted to silicon surfaces: grafting density and protein adsorption," Macromolecules, 31:5059-5070.

Yeo & Mrksich (2003) "Self-Assembled Monolayers That Transduce Enzymatic Activities to Electrical Signals," Angew. Chem. Int. Ed., 42:3121-3124.

* cited by examiner

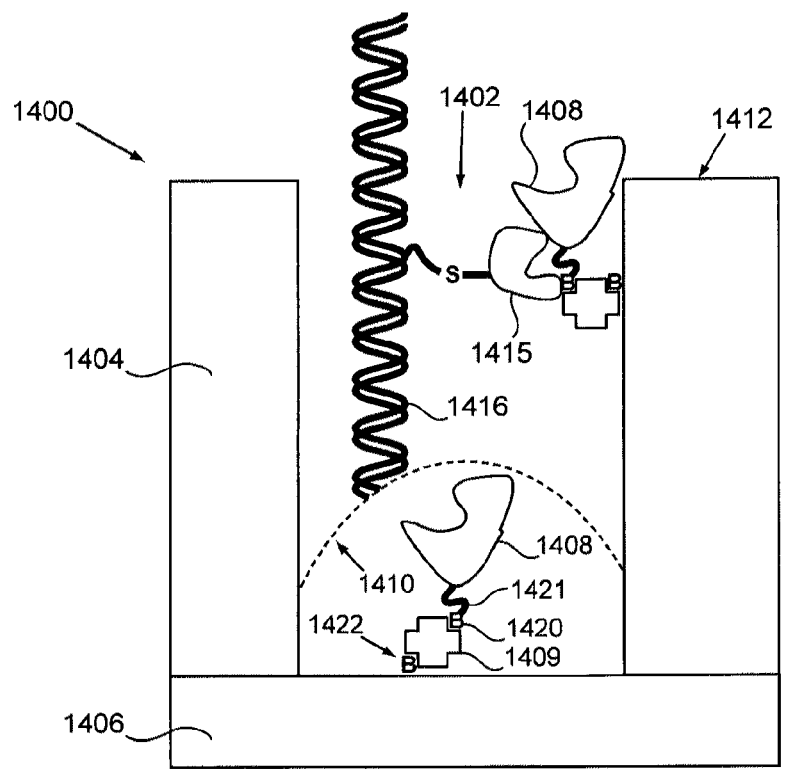
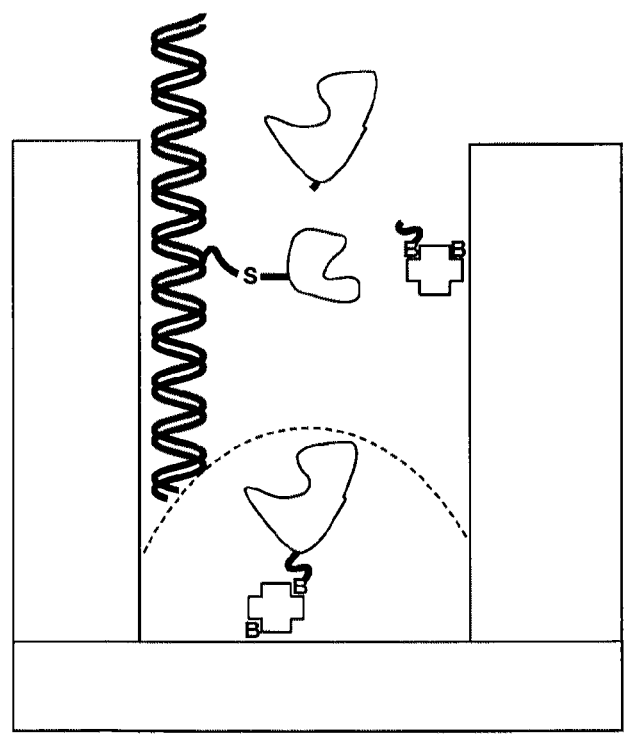
Fig. 14I
Fig. 14II

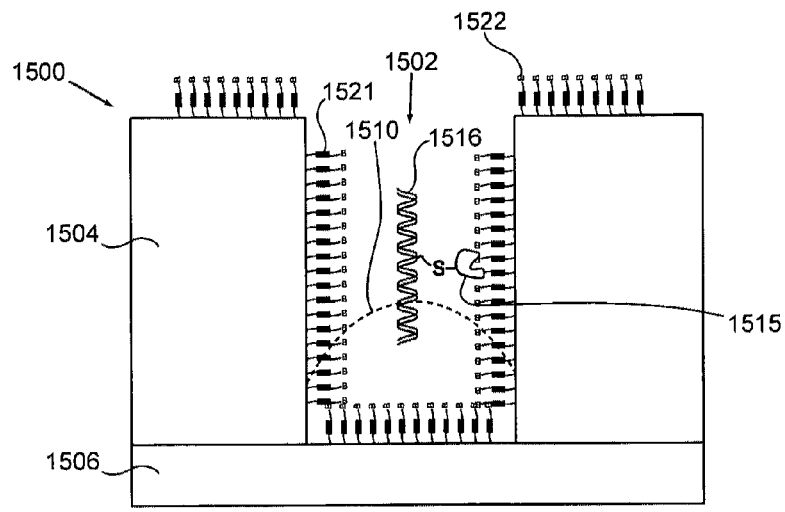
Fig. 15I
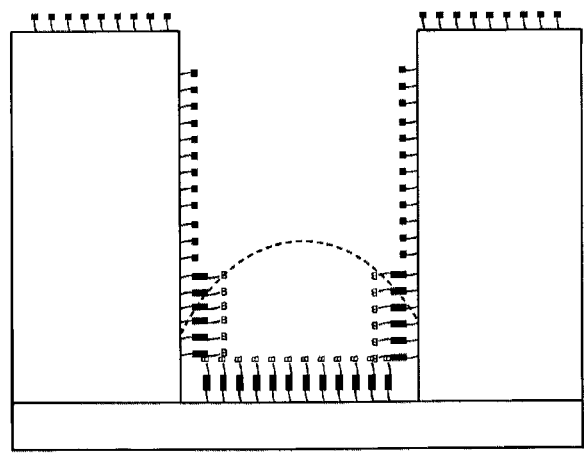
Fig. 15II
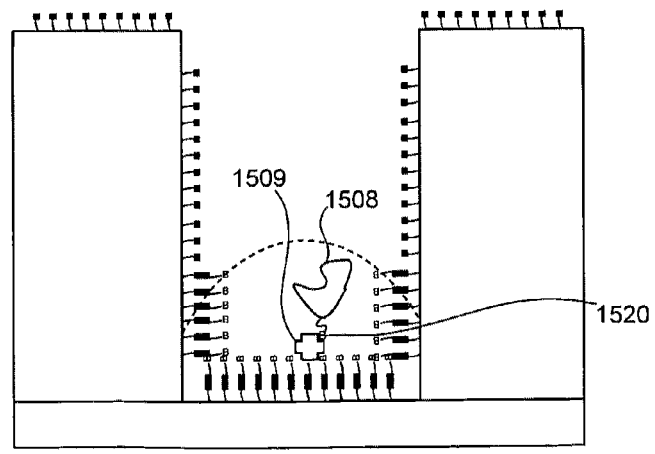
Fig. 15III

ARTICLES HAVING LOCALIZED MOLECULES DISPOSED THEREON AND METHODS OF PRODUCING SAME

CROSS-REFERENCE TO RELATED APPLICATIONS

This application is a continuation of U.S. patent application Ser. No. 11/731,748 filed Mar. 29, 2007 which is a continuation-in-part of application U.S. Ser. No. 11/394,352, filed Mar. 30, 2006, entitled "ARTICLES HAVING LOCALIZED MOLECULES DISPOSED THEREON AND METHODS OF PRODUCING SAME" by David R. Rank et al., which is incorporated herein by reference in its entirety for all purposes.

STATEMENT REGARDING FEDERALLY SPONSORED RESEARCH

Portions of the invention were made with government support under NHGRI Grant No. R01-HG003710-01 and the government may have certain rights to the invention.

FIELD OF THE INVENTION

The present invention relates to methods of producing substrates having selected active chemical regions by employing elements of the substrates in assisting the localization of active chemical groups in desired regions of the substrate. Methods that include optical, chemical and/or mechanical processes for the deposition, removal, activation and/or deactivation of chemical groups in selected regions of the substrate to provide selective active regions of the substrate are described.

BACKGROUND OF THE INVENTION

There are a wide range of analytical operations that may benefit from the ability to analyze the reaction of individual molecules, relatively small numbers of molecules, or molecules at relatively low concentrations. A number of approaches have been described for providing these sparsely populated reaction mixtures. For example, in the field of nucleic acid sequence determination, a number of researchers have proposed single molecule or low concentration approaches to obtaining sequence information in conjunction with the template dependent synthesis of nucleic acids by the action of polymerase enzymes.

The various different approaches to these sequencing technologies offer different methods of monitoring only one or a few synthesis reactions at a time. For example, in some cases, the reaction mixture is apportioned into droplets that include low concentrations of reactants. In other applications, certain reagents are immobilized onto surfaces such that they may be monitored without interference from other reaction components in solution. In still another approach, optical confinement techniques are used to ascertain signal information only from a relatively small number of reactions, e.g., a single molecule, within an optically confined area. Notwithstanding the availability of the above-described techniques, there are instances where further selectivity of reaction components for analysis would be desirable. The present invention meets these and a variety of needs.

BRIEF SUMMARY OF THE INVENTION

The present invention generally provides methods of providing functional surface modifications, e.g., active chemical groups, in selected regions of substrates, as well as the resultant substrates produced thereby, and the use of such substrates.

In a first aspect, the present invention provides methods of producing a substrate having selectively active regions thereon. The methods comprise providing a substrate having a plurality of nanostructures defined thereon, wherein each of the nanostructures limits an ability of a first activation controlling agent to provide active chemical groups on selected portions of a surface of the substrate. The substrate is then exposed to at least the first activation controlling agent to selectively provide active chemical groups on the selected portions of a surface of the substrate. Active chemical groups include, for example, chemical functional groups, active molecules (e.g., enzymes), and coupling or binding groups.

In another, related aspect, the invention provides methods of preparing an analytical substrate having selected active regions thereon. The method provides a substrate having an optical analysis structure disposed thereon, the optical analysis structure providing enhanced optical access to selected regions of the substrate. Surface functional groups are then provided that are capable of being activated or deactivated by a first electromagnetic radiation, which is directed at the substrate whereby the optical analysis structure directs the electromagnetic radiation to selectively activate or deactivate the surface functional groups in the selected regions of the substrate to provide selectively active regions of the substrate.

Another aspect of the invention features a method of providing a zero mode waveguides having an active chemical surface substantially at a bottom portion of the waveguide. The method comprises providing a zero mode waveguide disposed in a substrate, providing functional chemical groups on surfaces of the zero mode waveguide, and exposing first portions, but not second portions, of the surfaces of the zero mode waveguide to an activation controlling agent that selectively activates or deactivates the functional chemical groups on the first portions to provide an active chemical surface substantially at a bottom portion of the zero mode waveguide.

The invention also provides substrates and devices made using such methods, including zero mode waveguide arrays that comprise a plurality of zero mode waveguide cores disposed in a cladding layer, each core having a bottom surface, and a chemically active surface substantially only within the cores.

The invention further provides methods of providing a substrate having selected active regions disposed thereon that comprise providing a substrate having an optical enhancement structure defined thereon, the optical enhancement structure being capable of directing electromagnetic radiation to provide an enhanced electromagnetic field proximal to a selected region of the substrate surface sufficient to create a trapping force proximal to the selected region. Electromagnetic radiation is directed at the substrate to provide the enhanced electromagnetic field at the selected region sufficient to create a trapping force upon an active molecule proximal to the selected region. The active molecule is then coupled to the selected region.

The invention additionally provides methods of producing a substrate having selected active regions disposed thereon that comprise providing a substrate having a surface comprised of chemical functional groups, and a plurality of discrete nanoscale reaction regions defined thereon, and patterning one or more of a chemical functional group or an activation controlling agent onto the surface in selected regions to provide active chemical functional regions substantially only in the discrete nanoscale reaction regions.

Another aspect of the invention provides methods of identifying a sequence of a nucleic acid molecules. The method comprises providing a plurality of nucleic acid polymerase/template/primer complexes within discrete observation regions on a substrate, and detecting sequential addition of nucleotides or nucleotide analogs in a template dependent manner to identify a sequence of incorporation of the nucleotides or nucleotide analogs in the plurality of observation regions. In such methods, the substrate has been prepared to substantially reduce one or more of polymerase activity, polymerase presence, template presence, and primer presence in regions outside of the observation regions.

Relatedly, the invention provides a method of identifying a sequence of a nucleic acid molecule, comprising providing a plurality of nucleic acid polymerase/template/primer complexes within discrete observation regions on a substrate surface, and detecting sequential addition of nucleotides or nucleotide analogs in a template dependent manner to identify a sequence of incorporation of the nucleotides or nucleotide analogs in the plurality of observation regions. In such methods, an intra-observation region barrier is provided upon the substrate surface between at least first and second discrete observation regions to substantially prevent intra-observation region diffusion of one or more reactants or products.

The invention also provides methods of preferentially localizing desired molecules within an optical confinement disposed upon a substrate. The methods comprise depositing the desired molecules over the surface of the substrate, and selectively removing the desired molecules from the surface of the substrate that is not within the optical confinement. In one aspect, the substrate comprises an opaque (non-transparent) layer and a transparent layer, and the optical confinement comprises a zero mode waveguide disposed through the opaque layer to the transparent layer.

Selectively removing the desired molecules from the surface of the substrate that is not within the optical confinement optionally involves contacting the substrate with a deactivation component coupled to an exclusionary component that is at least partially excluded from entering into the optical confinement. The deactivation component removes the molecules it can access from the surface (e.g., from the upper surface and upper walls of the core of a zero mode waveguide); it is prevented from accessing the optical confinement, or the entirety of the optical confinement, by the exclusionary component.

In one class of embodiments, the deactivation component comprises an enzyme, for example, a protease (e.g., a non-specific or a site-specific protease), a nuclease, or a carbohydrase. The exclusionary component is optionally a large particle such as a bead, a macromolecule, or a rigid or semi-rigid elongated polymer. In one class of embodiments, the exclusionary component comprises a double-stranded nucleic acid molecule, e.g., a double-stranded DNA molecule coupled to a protease deactivation component.

The desired molecules that are selectively immobilized can be essentially any molecules, for example, active molecules such as enzymes (e.g., nucleic acid polymerases) or molecules comprising binding or coupling moieties (e.g., biotin molecules) which can be employed in turn to immobilize other molecules.

Further provided are methods of localizing a molecule within an optical confinement disposed on a substrate that comprise providing a light activated coupling group on the surface of the substrate, including within the optical confinement. Activating radiation is then directed at the substrate, wherein the optical confinement permits activating radiation to be incident only within the optical confinement. The molecule is then coupled to the light activated coupling group.

Another aspect of the invention provides methods of selectively immobilizing a molecule of interest on a substrate. The methods comprise providing a substrate having a first surface component and a second surface component where the first and second surface component have different surface characteristics, and selectively coupling the molecule of interest to the first surface component, based upon a difference between the surface characteristics of the first surface component and the surface characteristics of the second surface component.

In one class of embodiments, the differing surface characteristics comprise surface charge or electrostatic interactions at the surface. For example, the first surface component can have or acquire a negative surface charge and the second surface component a positive surface charge (or vice versa). As another example, the surface components can have different surface chemisorption characteristics; for example, the second surface component can have strong chemical affinity for a particular group (e.g., phosphonate or phosphate groups), while the first surface component does not have strong affinity for the group.

The methods can be employed to selectively immobilize molecules of interest, e.g., in a ZMW or other hybrid substrate. Thus, for example, the substrate optionally comprises a layer of the second surface component on a layer of the first surface component, with a zero mode waveguide disposed through the second surface component layer to the first surface component layer. In such embodiments (among others), the first surface component can comprise $SiO_2$ and/or the second surface component can comprise a metal or metal oxide (e.g., aluminum or aluminum oxide). In embodiments in which the hybrid substrate is in contact with a solution, the substrate can comprise a first surface component that is a material with a point of zero charge below the pH of the solution (e.g. $SiO_2$ at pH>2) and/or a second surface component that comprises a metal oxide with a point of zero charge above the pH of the solution (e.g. aluminum oxide at pH<8; other metal oxides that are positively charged at neutral pH include, but are not limited to, thallium oxide, iron oxide, yttrium oxide, zinc oxide, lanthanum oxide, and magnesium oxide).

In certain embodiments, the molecule of interest associates preferentially to the first surface component. For example, positively charged polymerase molecules preferentially associate with negatively charged silicate over positively charged metal surfaces. In other embodiments, the substrate is contacted with a first composition that selectively associates with the first surface component based upon the difference between the surface characteristics of the first and second surface components. The first composition can serve a blocking function, or it can associate, directly or indirectly, with the molecule of interest. Thus, for example, in one class of embodiments, the first composition comprises a first coupling group, and selectively coupling the molecule of interest to the first surface component comprises coupling the molecule of interest to the first coupling group (e.g., a functional chemical group, a binding group such as biotin, or the like).

In one class of embodiments, the first composition comprises a silane, e.g., for selective association with a silicate first surface component. Exemplary silanes include, but are not limited to, biotin-PEG-silanes. In another class of embodiments, the first composition comprises a phospholipid. In yet another class of embodiments, the first composition comprises polylysine-PEG or polylysine-PEG-biotin.

The methods optionally include contacting the substrate with a second composition that selectively associates with the second surface component based upon the difference between the surface characteristics of the first and second surface components. Treatment with the second composition is optionally performed before or after coupling of the molecule of interest to the first surface component, including before or after treatment with any first composition. In some embodiments, the second composition comprises a second coupling group, typically different from any first coupling group. Exemplary second compositions include, e.g., polyelectrolytes and polyelectrolyte-PEG copolymers. The method optionally includes depositing a polyelectrolyte multilayer on the second surface component.

Additional exemplary second compositions include compounds comprising one or more phosphonic acid or one or more phosphate groups. For example, the second composition can comprise polyvinylphosphonic acid; 2-carboxyethyl phosphonic acid; amino tri(methylene phosphonic acid); 1-hydroxyethylidene-1,1-diphosphonic acid; hexamethylenediaminetetra(methylenephosphonic acid); diethylenetriamine penta(methylene phosphonic acid); ethylenediamine tetra(methylene phosphonic acid); bis(hexamethylene triamine penta(methylenephosphonic acid)); 2-phosphonobutane-1,2,4-tricarboxylic acid; or monoethanolamine diphosphonate. As additional examples, the second composition can comprise an alkyl phosphate or an alkyl phosphonate, such as octyl phosphonic acid, decyl phosphonic acid, dodecyl phosphonic acid, hexadecyl phosphonic acid, octadecyl phosphonic acid, docosyl phosphonic acid, hydroxy-dodecyl phosphonic acid, hydroxy-undecenyl-phosphonic acid, decanediylbis(phosphonic acid), dodecylphosphate, or hydroxy-dodecylphosphate.

The two surface components can be differentially modified by different compositions. Thus, in one class of embodiments, the methods include contacting the substrate with a first composition that selectively associates with the first surface component and coupling the molecule of interest to the first composition to selectively couple the molecule of interest to the first surface component, and contacting the substrate with a second composition that selectively associates with the second surface component (before or after coupling of the molecule of interest or deposition of the first composition).

In an alternative aspect, the invention provides methods of selectively depositing a molecule of interest on selected regions of a substrate, comprising providing a substrate having first and second components, the first component comprising a conductive material and the second component comprising an insulator, and applying an electrical potential to the first component so as to increase or decrease association of a molecule of interest with a surface of the first component.

BRIEF DESCRIPTION OF THE DRAWINGS

FIG. 14 I-II schematically illustrates an exemplary process for selective localization of molecules using an exclusionary process in which a site-specific deactivation component removes the molecule of interest from the substrate.

FIG. 15 I-III schematically illustrates an exemplary process for selective localization of molecules using an exclusionary process in which a site-specific deactivation component removes a coupling moiety from the substrate.

Figure 1:
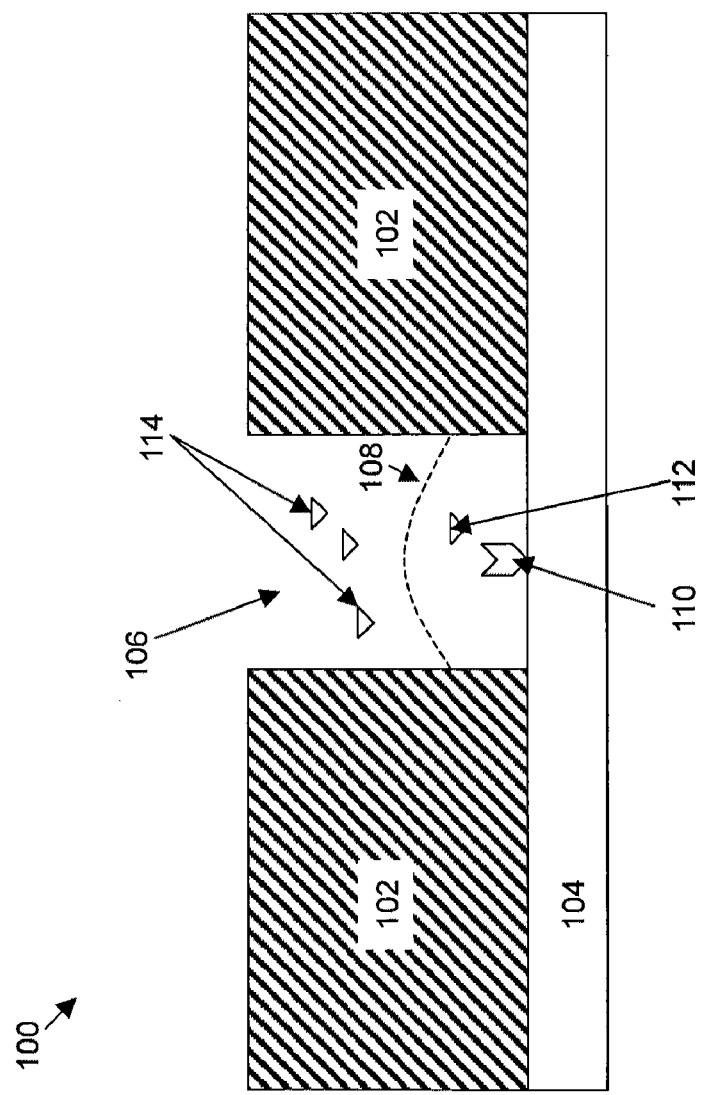
FIG. 1 shows a schematic illustration of a Zero Mode Waveguide (ZMW) in application.

Schematic figures are not necessarily to scale.

DETAILED DESCRIPTION OF THE INVENTION

I. General Description of Invention

The present invention is generally directed to methods and processes for providing desired molecules in preselected locations or areas on a substrate or within a set volume, and articles made from such methods or processes, and particularly, in desired low concentrations or as individual molecules, within an optical confinement. In particularly preferred aspects, the invention is directed to methods for localizing individual molecules within a particular space or volume, such that the spatial individuality of the molecule may be exploited, e.g., chemically, optically, electrically, or the like. The invention also provides the substrates, devices, receptacles and the like, e.g., the optical confinements, produced by these processes. While the processes of the invention may be broadly practical in providing individual molecules within any of a variety of given desired space or volume types, in particularly preferred aspects, the processes are used to selectively deposit or immobilize a desired molecule, such as an enzyme, within the optically accessible portion of an optical confinement, and particularly, a zero mode waveguide (ZMW).

In general, optical confinements are used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent substrate at an angle that yields total internal reflection within the substrate. Notwithstanding the TIR, some small fraction of the light will penetrate beyond the outer surface of the substrate and decay rapidly as a function of distance from the substrate surface, resulting in illumination of very small volumes at the surface. Similarly, ZMW structures may be employed that utilize a narrow core, e.g., from 10 to 100 nm, disposed through a cladding layer where the core is dimensioned such that the desired electromagnetic radiation is prevented from propagating through the core. As a result, the radiation will permeate the core only a very short distance from the opening of the core, and consequently illuminate only a very small volume within the core. A variety of other optical confinement techniques, including, e.g., field enhancement by sharp metal tips, nanotube confinement, thin slit confinement, near-field resonant energy transfer confinement, near field aperture confinement, diffraction limited optical confinement, and stimulated emission depletion confinement, are contemplated, as well as all other confinements described in U.S. Ser. Nos. 10/944,106 (now issued as U.S. Pat. No. 7,170,050) and 09/572,530 (now issued as U.S. Pat. No. 7,056,661) and U.S. Pat. No. 6,917,726, each of which is incorporated herein by reference in its entirety for all purposes.

Zero mode waveguides (ZMWs) are generally characterized by the existence of a core surrounded by a cladding, where the core is dimensioned such that it precludes a substantial amount of electromagnetic radiation that is above a cut-off frequency from propagating through the core. As a result, when illuminated with light of a frequency below the cutoff frequency, the light will only penetrate a short distance into the core, effectively illuminating only a small fraction of the core's volume. In accordance with the present invention, the core comprises an empty or preferably fluid filled cavity surrounded by the cladding layer. This core then provides a zone or volume in which a chemical, biochemical, and/or biological reaction may take place that is characterized by having an extremely small volume, and in some cases sufficient to include only a single molecule or set of reacting molecules. ZMWs, their fabrication, structure, and use in analytical operations are described in detail in U.S. Pat. No. 6,917,726 and Levene, et al., Science 299(5607):609-764 (2003), the full disclosures of which are hereby incorporated herein by reference in their entirety for all purposes.

In the context of chemical or biochemical analyses within ZMWs as well as other optical confinements, it is clearly desirable to ensure that the reactions of interest are taking place within the optically interrogated portions of the confinement, at a minimum, and preferably such that only a single reaction is occurring within an interrogated portion of an individual confinement. A number of methods may generally be used to provide individual molecules within the observation volume. A variety of these are described in U.S. patent application Ser. No. 11/240,662, filed Sep. 30, 2005 (now issued as U.S. Pat. No. 7,763,423), incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

In some cases, it may be further desirable that reactions of interest be reduced or even eliminated from other regions outside of the observation volume, e.g., on the overall substrate housing ZMWs, the cladding layer, etc., both inside and outside of the observation volume. In particular, reactions that are outside of the range of interrogation may, nonetheless, impact the reaction of interest or the monitoring of that reaction, by affecting reaction kinetics through depletion of reagents, increasing concentration of products, contributing to signal background noise levels, e.g., through the generation of products or consumption of reactants, that may interfere with the interrogated reaction or that provide excessive detectable background product levels that diffuse into and out of the interrogation volume of the waveguide. Accordingly, selective and preferential deposition and/or immobilization of the reaction components within the observation volume are particular advantages of the invention. These are generally practicable both as an alternative to and, preferably, in addition to the low density deposition methods referenced above. In the context of the foregoing, molecules of interest may be described as being preferentially located in a particular region, or localized substantially in a given region. It will be appreciated that use of the term preferentially is meant to indicate that the molecule is localized in a given location at a concentration or surface density that exceeds that of other locations in which it is not preferentially localized. Thus preferential immobilization of a given molecule in a first region will mean that the molecule is present in such region at a higher density or concentration than in other regions. Density in such regions may be as much as 20% greater, 30% greater, 50% greater, 100% greater, or upwards of 200%, up to 1000% or more of the concentration or density in other regions, and in some cases 100 times greater, 1000 times greater or more. Similar meaning is generally applicable to indications that a given molecule is substantially only located in a given region.

In the case of, for example, ZMWs used for single molecule enzymatic analysis, it may be desirable to provide a single enzyme molecule within the illumination volume of a waveguide, and preferably upon the bottom or base surface of the waveguide. As noted above, it may therefore be further desirable to ensure that additional enzyme molecules are not present upon surfaces other than the bottom surface, e.g., the walls of the core and/or the surfaces of the cladding layer that are not part of the core, and the like.

A particularly valuable application of the substrates produced by the process of the invention is in processes termed "single molecule sequencing applications." By way of example, a complex of a template nucleic acid, a primer sequence and a polymerase enzyme may be monitored, on a single molecule basis, to observe incorporation of each additional nucleotide during template dependent synthesis of the nascent strand. By identifying each added base, one can identify the complementary base in the template, and thus read off the sequence information for that template. In the context of ZMWs, an individual polymerase/template/primer complex may be provided within the observation volume of the ZMW. As each of four labeled (e.g., fluorescent) nucleotides or nucleotide analogs is incorporated into the synthesizing strand, the prolonged presence of the label on such nucleotide or nucleotide analogs will be observable by an associated optical detection system. Such sequencing processes and detection systems are described in, e.g., U.S. Patent Application Publication No. 2003/0044781 and U.S. patent application Ser. No. 11/201,768, filed Aug. 11, 2005 (now issued as U.S. Pat. No. 7,805,081), the full disclosures of which are incorporated herein by reference in their entirety for all purposes. Such single molecule sequencing applications are envisioned as being benefited by the methods described herein, through the selected immobilization of polymerases, templates or primers or complexes of any or all of these, preferentially within selected regions on a substrate, and/or substantially not on other portions of the substrate.

In general, selective provision of a molecule of interest in a given location, e.g., in the illumination volume within a ZMW, may be accomplished using either additive or subtractive processes. By additive process, is generally meant that the individual molecule is placed or deposited in the desired location and not elsewhere. By contrast, subtractive processes denote the deposition of the molecule of interest more ubiquitously and non-selectively, e.g., over an entire substrate surface, followed by the selected removal of the molecule of interest from the non-desired locations. While these descriptions provide convenience in describing various processes, it will be appreciated that the result of one process may be indistinguishable from the result of the other process. It will also be appreciated that many processes may include steps that may be described as either additive, subtractive, or both. Although generally discussed in terms of localization of enzymes or other macromolecular groups, for purposes of the present invention, the molecule of interest may be any of a variety of different functional molecules for which one desires to provide spatial individuality or enhanced localization. Such groups include active molecules, such as catalytic molecules like enzymes, but also include molecules with more passive functionality, e.g., non catalytic groups, such as binding or coupling groups, hydrophobic or hydrophilic groups, structural enhancement groups, e.g., for adhesion promotion, activatable or deactivatable groups, or the like. Binding or coupling groups may include small molecule coupling groups or they may include macromolecular coupling groups, e.g., antibodies, antibody fragments, specific binding pairs, such as avidin/biotin, binding peptides, lectins, complementary nucleic acids, or any of a variety of other binding groups. Catalytically active molecules will typically include any catalytically active molecule for which one desires spatial individuality, e.g., to exploit in single molecule analyses, or the like.

In at least one aspect, the present invention is directed to providing enhanced isolation of discrete reaction and/or observation regions. This is not simply to provide optical isolation between such regions, but also to provide chemical and/or environmental isolation for such regions. In a general sense, this is accomplished by providing a barrier or zone between reaction and/or observation regions that substantially prevents the diffusion of reactants and/or products from outside a particular reaction zone from entering and potentially interfering with the reaction taking place therein, or the observation of that reaction. In providing the requisite isolation, one may focus on one or both of: (1) providing sufficient separation/isolation between neighboring reaction/observation regions; and (2) eliminating any potentially interfering components from the spaces between such neighboring regions, e.g., clearing any reactants, products and/or enzymes from such spaces, and creating a type of "demilitarized zone" between observation regions.

Providing enhanced isolation generally relates to providing a barrier of some sort between observation regions. In general, such barriers may simply include sufficient distance in a fluidic system such that reactants and products may not diffuse from one reaction into a particular observation region, whether the reaction is in a neighboring observation region or is located somewhere else. One may provide such distance across a planar substrate or one may increase the effective diffusion distance by providing a structured or contoured surface on the substrate. For example, in particularly preferred aspects, one may provide discrete reaction/observation regions within nanoscale wells to effectively increase the distance between such regions, as well as treat or otherwise produce such substrates, to reduce or eliminate any reactants and/or products from existing or being generated in the space or regions between the selected regions, e.g., surfaces other than those at or toward the bottom surface of the nanoscale wells.

II. Additive Processes

As noted above, in at least one aspect, an additive process is employed to provide the desired immobilized molecules of the invention. The additive processes typically rely upon the selective provision of binding or coupling groups at the desired location, followed by the deposition of the molecules of interest. This deposition may, again, be the result of additive or subtractive processes.

In at least a first aspect, the additive processes of the invention typically include the deposition of a coupling group upon the substrate surface that selectively binds the molecule of interest only within the desired region on the surface, e.g., within the observation area of an optical confinement such as a ZMW. Coupling of functional groups, including activatable functional groups, to surfaces may generally be carried out by any of a variety of methods known in the art. For example, in the context of silica based substrates, e.g., glass, quartz, fused silica, silicon, or the like, well characterized silane chemistries may be used to couple other groups to the surface. Such other groups may include functional groups, activatable groups, and/or linker molecules to either of the foregoing, or the actual molecules of interest that are intended for use in the end application of the surface. In the context of other substrate types, e.g., polymeric materials, metals or the like, other processes may be employed, e.g., using hybrid polymer surfaces having functional groups coupled thereto or extending from the polymer surface using, e.g., copolymers with functional groups coupled thereto, metal associative groups, i.e., chelators, thiols, or the like.

In at least a first aspect of the invention, providing coupling of a molecule of interest only within a desired area or region is typically carried out by providing an activatable coupling group coupled to the surface of the overall substrate that is selectively activated only within the desired region, or by using a selectively de-activatable coupling group and selectively deactivating it in all but the desired region. The selective provision of active coupling groups only where desired allows selective deposition and coupling of the molecule of interest substantially only in the desired regions. For ease of discussion, the portion of a surface or substrate in which one wishes to selectively provide molecules of interest for a given application are referred to herein as the "desired regions" while regions outside of these regions are referred to as the non-desired regions. Such desired and non-desired regions may include planar surfaces or may comprise three dimensional structures such as wells, recesses, surface irregularities, posts, pillars, trenches, troughs, channels, capillaries, porous materials, or the like.

A variety of different activatable coupling groups may be used in conjunction with this aspect of the invention. Typically, such groups include coupling groups that are capped or blocked with a selectively removable group. These include groups that are thermally altered, e.g., thermolabile protecting groups, chemically altered groups, e.g., acid or base labile protecting groups, and photo alterable groups, e.g., photocleavable or removable protecting groups.

Deactivation of coupling groups, e.g., in non-desired regions, may comprise the use of groups that may be directly selectively deactivated, e.g., through the use of thermal, chemical or photo-induced chemistries that cap or result in the removal of functional groups, i.e., through photo-induced cross-linking, photocleavage, or the like. Alternatively, and in certain preferred aspects, such deactivation methods utilize selective activation of the coupling group in the non-desired regions, followed by blocking or capping of the resulting active coupling group with a neutral or inert blocking group, e.g., a group that is substantially incapable of coupling to the molecule of interest, or an intermediate linking molecule, under coupling conditions subsequently applied to couple such groups to the desired regions. This subsequently added blocking group may be irreversible or reversible. However, reversibility of such capping, if any, will typically involve a mechanism other than that of the underlying activatable coupling group, to avoid re-activating capped groups in the non-desired regions while activating those underlying activatable groups in the desired regions. For example, where one is employing a photoactivation strategy to selectively activate groups in the desired regions, capping groups applied to non-desired regions will typically not be photoactivatable or otherwise activated by any conditions to which the surface will be exposed in application.

Following the capping of coupling groups in the non-desired regions, the coupling groups within the desired regions, or area of interest, may be selectively activated and coupled with the molecule of interest. For ease of discussion, whether photoactivation involves photocleavage of a blocking group, or photoactivation through alteration of a chemical structure without removal of a larger blocking group, per se, e.g., results in modified groups or addition of other groups, it will generally be referred to herein as activation, e.g., photoactivation.

In at least one particularly preferred aspect, photoactivatable coupling groups are used to selectively deposit molecules of interest in desired regions, e.g., using chemically active coupling groups that are capped with a photo-labile protecting groups. Such photoactivatable coupling mechanisms are particularly useful for systems that employ optical confinements such that light for both observation of an ultimate reaction of interest and for activation of the coupling group is only capable of illuminating the desired region, e.g., those regions of a ZMW closest to the core opening from which the core is illuminated. In particular, because activating light directed at a ZMW will only illuminate a restricted volume, e.g., the illumination volume, molecules of interest will be selectively coupled substantially only within the illumination volume. Restated, the same optical confinement effect used to only monitor reactions within the small confined volume of the illumination volume (which typically substantially defines the observation volume in the applicable analytical operations to which the ZMW will be put), likewise only permits activation (and consequent coupling) within that same confined volume or portion of the ZMW. As will be appreciated, by modulating the activation radiation, one can further control the illumination volume during activation to be a smaller volume than the illumination volume during application. In particular, by applying a lower power illumination, using a longer wavelength of activation light than illumination/interrogation light, one can illuminate, activate and thus couple molecules of interest only to a subset of the surface that will ultimately be within the illumination volume in the ultimate application.

For a number of the specific aspects of the invention, it is generally preferred to utilize a substrate that provides for the selective direction of electromagnetic radiation to desired regions, both in terms of the ultimate application of such substrates, e.g., in interrogating chemical, biochemical and/or biological reactions on those substrates, and in providing selectively activated surfaces for selectively immobilizing molecules of interest in those regions for exploitation during such analyses. In sum, one takes a basic function of the substrate that is used in its ultimate application, and exploits that function to improve the fabrication and processing of that substrate for that application. In the context of directing radiation, a substrate that is used to focus radiation into desired regions for interrogation of reactions within such regions is processed using the same radiation directing properties to selectively functionalize those desired regions.

A variety of different coupling groups may be used in this context, depending upon the nature of the molecule of interest to be subsequently deposited upon and coupled to the substrate. For example, the coupling groups may include functional chemical moieties, such as amine groups, carboxyl groups, hydroxyl groups, sulfhydryl groups, metals, chelators, and the like. Alternatively or additionally, they may include specific binding elements, such as biotin, avidin, streptavidin, neutravidin, lectins, SNAP-tags™ or substrates therefore (Covalys Biosciences AG; the SNAP-tag™ is a polypeptide based on mammalian O6-alkylguanine-DNA-alkyltransferase, and SNAP-tag substrates are derivates of benzyl purines and pyrimidines), associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a photoactivatable coupling group, e.g., photoactivatable biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin.

Photo-labile protecting groups employed in this aspect of the invention may include a variety of known photo-cleavable protecting groups, including, for example, nitroveratryl, 1-pyrenylmethyl, 6-nitroveratryloxycarbonyl, dimethyldimethoxybenzyloxycarbonyl, 2-nitrobenzyloxycarbonyl, methyl, methyl-6-nitropiperonyloxycarbonyl, 2-oxymethylene anthraquinone, dimethoxybenzyloxy carbonyl, 5-bromo-7-nitroindolinyl, o-hydroxy-alpha-methyl cinnamoyl, and mixtures thereof, as described in U.S. Pat. Nos. 5,412,087 and 5,143,854, each of which is incorporated herein by reference in its entirety for all purposes.

Coupling of the photoactivatable coupling groups to the surfaces of interest may be accomplished by a number of methods known in the art. For example, photoprotected or activatable groups may include a carboxyl group that is coupled through hydroxyl groups on the surface or attached to the surface through a linker group, e.g., a PEG molecule. Alternatively, amine groups on the photoactivatable groups may be coupled to surface bound epoxy groups. Alternatively, activatable groups precoupled to linker molecules, e.g., PEG groups, may be silanated and attached directly to surfaces through known processes.

Examples of the compounds used in the foregoing coupling strategies, e.g., using MeNPOC protected biotin, are illustrated below:

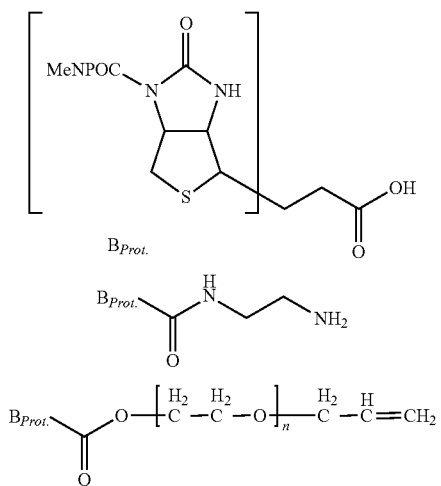

Additional light sensitive protecting groups include groups useful for coupling amines, such as trimethylphenyloxycarbonyl (TMPOC), groups useful for coupling acids, such as phenacyl ester (313 nm cleavage), α-phenacyl ester, Desyl ester (350 nm), Bis(o-nitrophenyl)methyl ester (320 nm), 1-pyrenylmethylester(340 nm), N-8-nitro-1,2,3,4-tetrahydroquinolylamide (350 nm), as well as esters of the following compounds:

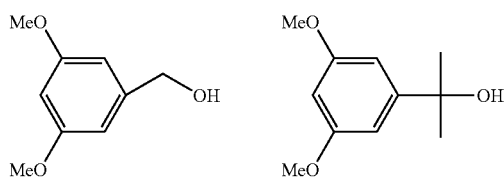

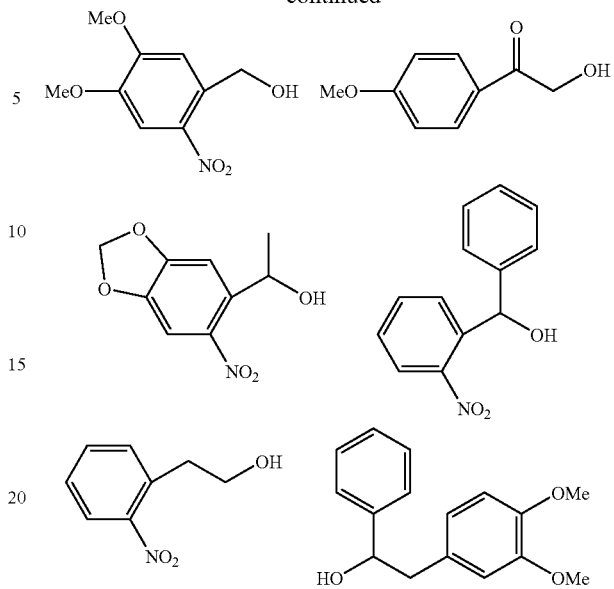

For those aspects of the invention that use longer wavelengths for activation or deprotection, appropriate longer wavelength labile groups would be used, such as brominated 7-hydroxyxoumarin-4-yl-methyls, which are photolabile at around 740 nm. Other such groups are known to those of skill in the art.

Also useful are such photolabile groups for coupling to alcohols, including, e.g., some of the groups described above, as well as p-nitrobenzyloxymethyl ether, p-methoxybenzylether, p-nitrobenzylether, mono, di or trimethoxytrityls, diphenylmethylsilyl ether, sisyl ether, 3',5'-dimethoxybenzoincarbonate, methanesulfate, tosylate, and the like. These and a variety of other photocleavable groups may be employed in conjunction with this aspect of the invention, and are described in, e.g., the CRC Handbook of Organic Photochemistry and Photobiology, Second Edition, and Protective Groups in Organic Synthesis (T. W. Greene and P. G. Wuts, $3^{rd}$ Ed. John Wiley & Sons, 1999), each of which is incorporated herein by reference in its entirety for all purposes.

In addition to, or as an alternative to, the use of the previously described, relatively large, photo-removable protecting groups, the invention also includes the use of photoactivatable groups, e.g., groups that are chemically altered, other than through the removal of such blocking groups. For example, vinyl or allyl groups may be coupled to surfaces and simultaneously illuminated and coupled with appropriate groups to be coupled that bear, e.g., sulfhydryl groups, such as biotin having a sulfhydryl group coupled to it either directly or through a linker molecule, which react with the activated vinyl or allyl group to couple to the surface. Alternatively, other groups, like nitroarylazides may be employed as the activatable coupling groups. A wide variety of other photoactivatable compounds may likewise be used, including, e.g., nitrospiropyran groups (See, Blonder et al., J. Am. Chem. Soc. 1997, 119:10467-10478, and Blonder et al., J. Am. Chem. Soc. 1997, 119:11747-11757.

In one aspect, a photoinitiator, e.g., a long wavelength photoinitiator, is employed, such as Irgacure 784 (bis-(eta 5-2,4-cyclopentadien-1-yl)bis[2,6-difluoro-3-(1H-pyrrol-1-yl)phenyl]titanium; Ciba Specialty Chemicals) that can initiate free radical reactions at wavelengths as long as 530 nm.

Such long wavelength photoinitiators have a variety of applications. For example, a surface (e.g., a metal oxide surface) can be coated with vinyl-alkyl-phosphonate. Exposure of a desired region of the surface to a 530 nm laser in the presence of Irgacure 784 and biotin-PEG-SH results in formation of biotin-PEG-alkyl-phosphonate in that region. The biotin can subsequently be employed to immobilize a molecule of interest to the desired region.

In related aspects, the photoactivatable component may be provided in solution and activated proximal to the surface region where localization is desired. For example, one may graft an activatable binding component or other molecule of interest onto an active silane surface. One example of such a system includes photoactivatable psoralen-biotin compounds (available from, e.g., Ambion, Inc.), that are activatable under UV light for coupling with a silanated surface, e.g., a trimethoxysilane modified surface.

Those aspects of the invention that include an additive process using a selective surface activation generally encompass a number of different strategies for selective activation in the desired locations. Such strategies may include a single activation step, a multiple activation step process, a multiple step process that includes both activation and deactivation steps or processes, or the like. For ease of discussion, such multiple step processes are described with reference to photoactivation and/or photodeactivation processes, although it will be appreciated that other non-photo driven processes may be similarly employed.

In at least a first, relatively simple aspect, the selective activation of photo-activatable coupling groups in the desired region involves a single step of directing activating radiation at the desired region and coupling the molecule of interest to the activated coupling groups that are disposed thereon. As noted, in the case of optical confinements where it is desirable to localize the molecule of interest, e.g., an enzyme, within the illumination volume, the single step photo-driven activation should result in coupling substantially only within the illumination volume. Further, as noted previously, by modulating the activation radiation, one can further focus the activation, and thus coupling of groups of interest, in a subset of the illumination volume that is interrogated during the ultimate application, e.g., in nucleic acid sequence determination using an immobilized polymerase enzyme.

The basic functional structure of a ZMW structure is schematically illustrated in FIG. 1. As shown, a ZMW structure 100 is provided that includes a cladding layer 102 deposited upon a transparent substrate layer 104. A core 106 is disposed through the cladding layer to expose the transparent layer 104 below. The core is dimensioned to provide optical confinement by preventing propagation of electromagnetic radiation that falls below a cut-off frequency through the core. Instead, the light only penetrates a short distance into the core, illuminating a relatively small volume, indicated as bounded by the dashed line 108. By providing reactants of interest within the observation volume, e.g., enzyme 110 and substrate 112, one can selectively observe their operation without interference from reactants, e.g., substrates 114 outside the observation volume, e.g., above line 108.

Figure 2:
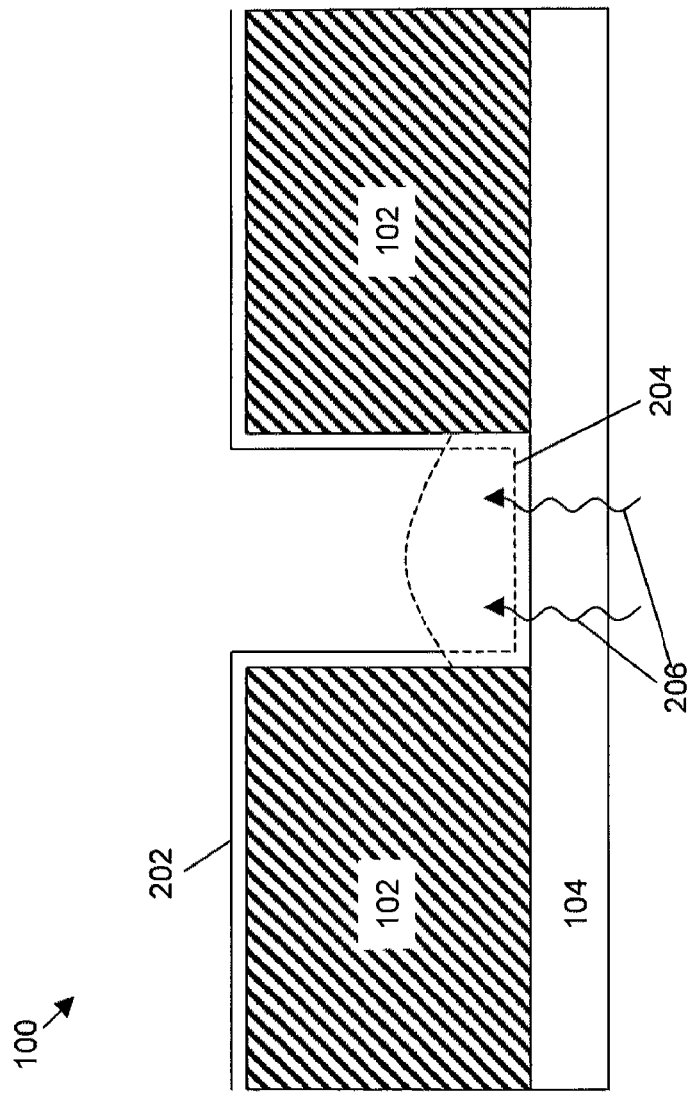
FIG. 2 provides a schematic illustration of a light directed surface activation process of the invention.

As noted previously, it is generally desirable that in performing molecular analyses, e.g., enzyme analyses, that the molecule of interest be provided preferentially within the illumination or observation volume. Accordingly, a simple activation strategy, as applied to ZMWs, is schematically illustrated in FIG. 2, with reference to FIG. 1. As shown, the ZMW structure 100 may be first treated to provide an activatable surface, e.g., shown as solid line 202. As shown, the treatment step is not selective, in that it provides such an activatable surface over the entire surface of the structure, including cladding layer 102. The activatable groups that are within the illumination volume, e.g., as bounded by dashed line 108, are then subjected to activation (as indicated by dashed line 204). In the context of a ZMW structure, this typically involves exposing the activatable groups to activating radiation through the transparent substrate 104, as indicated by waved arrows 206. As will be appreciated, the activation radiation decays sufficiently beyond the illumination volume, and as such, substantially activates only the groups therein, e.g., those below dashed line 108. Molecules of interest, e.g., enzymes, or enzyme specific coupling groups, are then coupled to the activated groups within the observation volume, and nowhere else on the surface. It will be appreciated that the reference to the illumination volume as having a well defined border is simplified for ease of discussion, and that decay of illumination through the ZMW core is not so abrupt. As a result, both the illumination and, as a result, the level of surface photo-activation from such illumination would be expected to decrease in a related fashion with increasing distance from the illuminated end of the waveguide core. The rate of radiation decay and the activation levels may decrease at different rates, depending upon the nature of the activation processes, e.g., whether there is saturation at any point, as well as whether the activation processes are single or multiple photon processes.

In an alternative process, an additional activation step may be employed to further select the region to which molecules of interest may be coupled. In particular, in a given activation step within an optical confinement, e.g., a ZMW, illumination as shown in FIGS. 1 and 2 will generally result in a spectrum of activation within the confinement, with more activated groups being present where illumination is greatest, e.g., at the bottom surface of the waveguide. As the illumination decreases with further penetration into the waveguide, the activation level or efficiency of activation will decrease depending upon the characteristics of the activatable group the intensity of the illumination and the amount of time exposed. This will result in a decreasing probability of activation of groups in the portions of the illumination region where light penetration decreases and thus, illumination is less. By then capping these activated groups with a second photoremovable group and repeating the activation step, the probability of the groups present being activated away from high illumination is similarly limited, but now is applied to a smaller number of groups. This is further illustrated with the following example: if one has a uniform distribution of photoactivatable groups in a ZMW-structure that are activatable with a first wavelength of light, at a particular distance from the bottom of the waveguide, one half of all activatable groups present are activated. If the active groups are then capped with a second photoactivatable group that is activated at a different wavelength, activation of those groups will again activate only half of the activatable groups present at the particular distance, or one fourth of the originally activatable groups. The result when applied over the spectrum of activation is a more narrowly focused activation/coupling area approaching the bottom of the waveguide structure.

Figure 3:
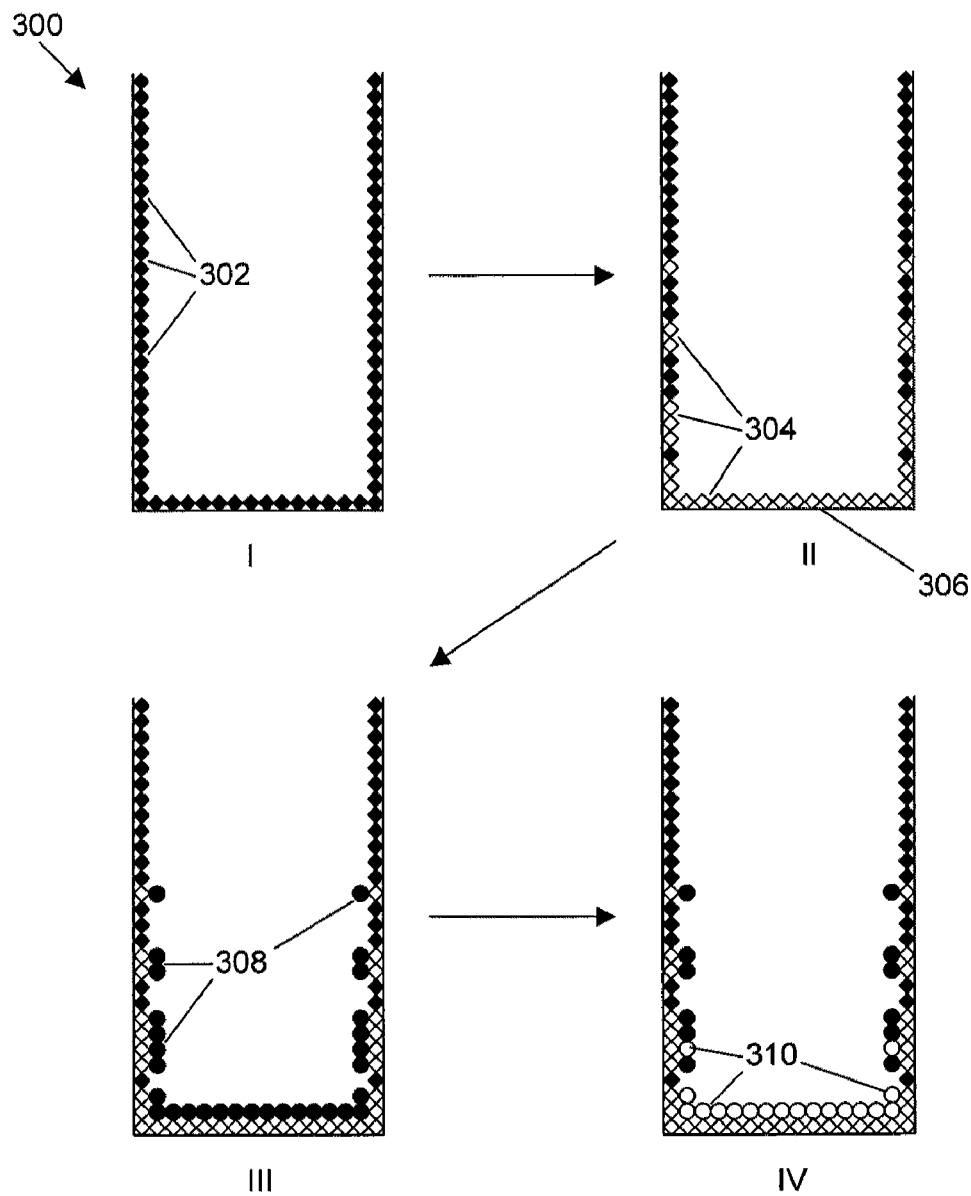
FIG. 3 I-IV provides a schematic illustration of a process for providing active surfaces in optically relevant portions of optical confinements like ZMWs.
Figure 4:
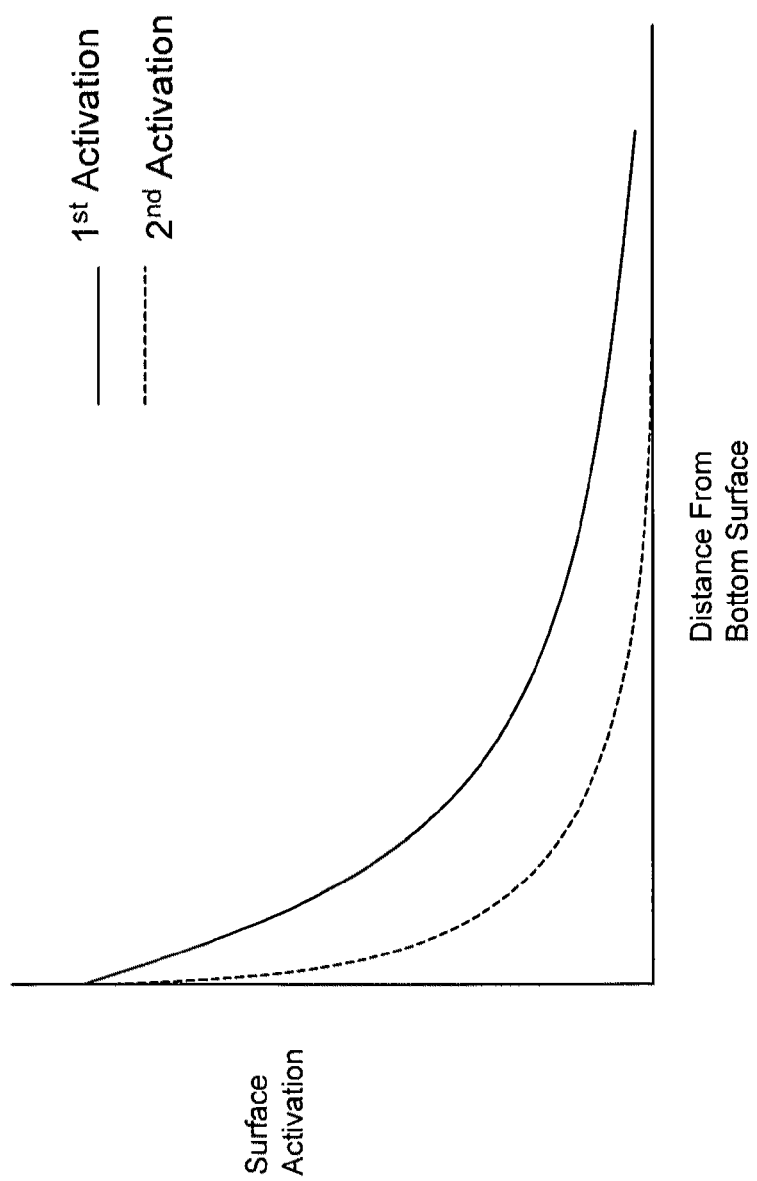
FIG. 4 provides a simulated plot of surface activation level as a function of the distance from the bottom surface of a ZMW over two separate activation stages.

A schematic illustration of a double activation method is provided in FIG. 3. In accordance with the double activation method, a waveguide structure 300, for example, is provided with a surface coating of photoactivatable groups uniformly applied over the surface (shown in panel I, as black diamonds 302). A first activation step (panel II) is used to activate the activatable groups within a waveguide (shown as open diamonds 304) by, e.g., directing an activation light through the bottom surface 306 of the waveguide 300. Instead of coupling the molecule of interest to those activated groups, a second activatable group (shown as black circles 308 in Panel III), that is activated by a different wavelength of light can be used to cap the activated groups 304. A subsequent activation step (Panel IV) then activates a subset of the newly capped groups (shown as open circles 310), and the molecule of interest (not shown) is then coupled to these newly activated groups. FIG. 4 provides an exemplary simulated plot of surface activation (concentration of activated surface groups) vs. distance from the bottom surface of a ZMW, for both a first and second activation step. As shown, a first activation step would be expected to yield an activation profile that falls off in conjunction with a rate of decay of activation light away from the bottom surface of a ZMW. After capping with a second photoremovable group, and reactivation at a different wavelength, one would expect a similar decay profile, but based upon only the previously activated groups. As a result, the activated groups would be more focused at the bottom surface of the waveguide than with just a single activation step. While described in terms of two steps, it will be appreciated that more steps could be performed to further focus the activated region on the surface.

As used herein, unless indicated otherwise from the specific context, capping generally refers to coupling an additional group to an otherwise reactive group such that the resulting compound is not active to further applied coupling or other reactions of interest. Such capping molecules typically comprise groups that will couple to the exposed coupling group but which are otherwise natural to the desired reaction, and will vary depending upon the nature of the groups to be capped. They may include neutral silane groups for capping silanol surface groups, or they may include other non-reactive materials, e.g., non-reactive organic materials, e.g., alcohols, alkyl groups, alkenyl groups, or the like. Such capping groups may be small molecules or may include larger polymeric or macromolecular structures, such as polyethylene glycols (PEGs), or the like. Capping chemistries are widely practiced in surface modification, derivatization and passivation processes that are discussed in, e.g., Immobilized Biomolecules in Analysis: A Practical Approach (Cass and Ligler Eds.) Oxford University Press, 1998, and Hermansonn et al., Immobilized Affinity Ligand Techniques, Academic Press, Inc. 1992, the full disclosures of which are incorporated herein by reference in their entirety for all purposes.

Figure 5:
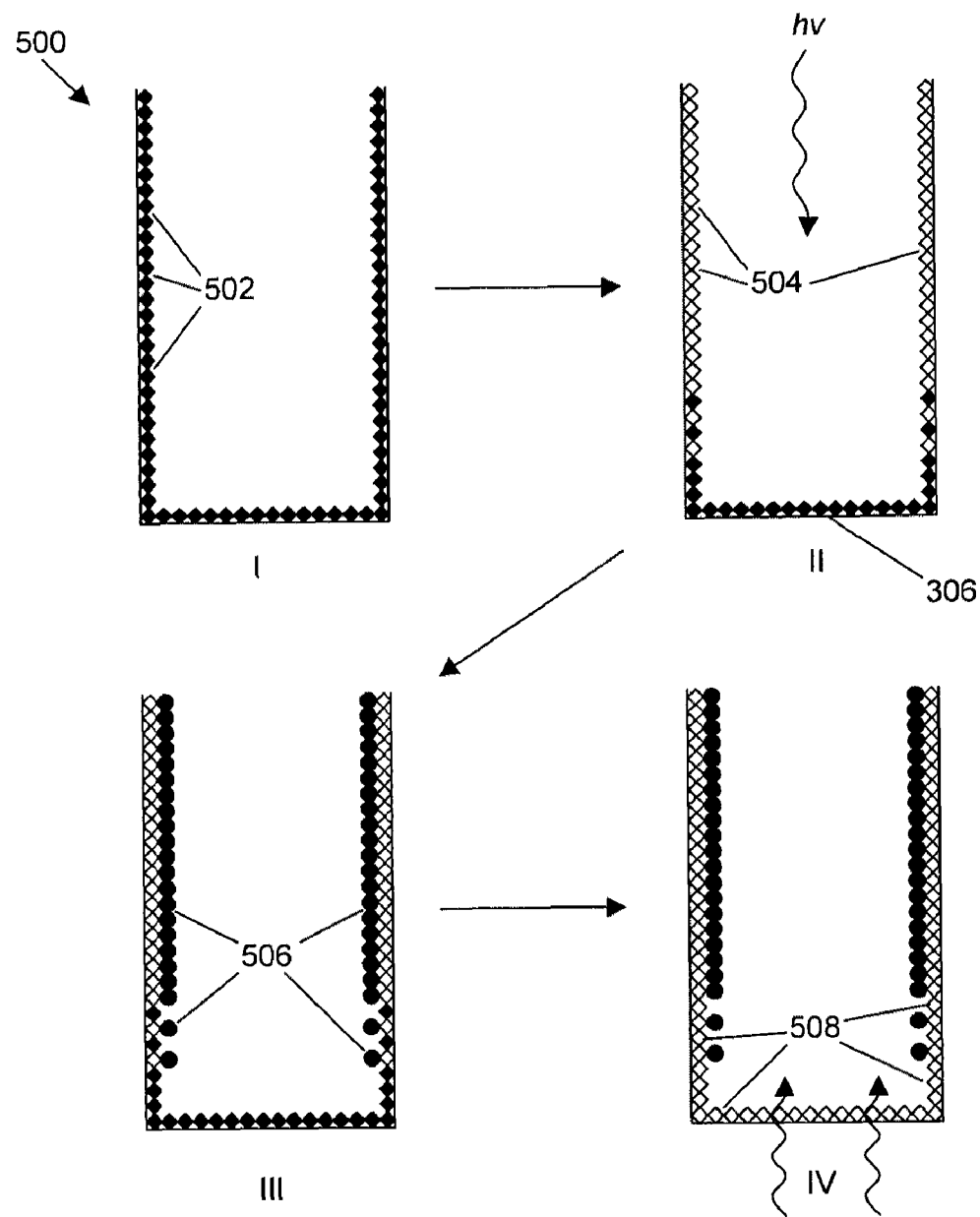
FIG. 5 I-IV provides a schematic illustration of an alternate light activation strategy using a two activation step process.

In another multi-step approach, iterative steps of activation and deactivation may be employed to focus the coupling of the molecule of interest. As noted previously, photoactivatable groups may be employed in accordance with the deactivation schemes described above, e.g., where areas other than the desired area are activated and capped or blocked, followed by activation within the area of interest and coupling of the molecule of interest. This method may prove more useful for applications based upon ZMWs. In particular, through an illumination from the open end of the waveguide, one will typically activate, and subsequently cap activatable groups not only on the upper surface of the cladding layer, but also, some portion of the activatable groups on the walls of the waveguide core. Subsequent activation from the bottom or closed end of the core will then only be able to activate those activatable groups that have not yet been capped. To the extent activation radiation penetrates greater than half the length of the core; this will result in a greater selection of activation for deposition at or toward the bottom of the ZMW. Such a method is schematically illustrated in FIG. 5.

In particular, on a substrate having optical confinements, such as ZMW 500, disposed upon it, one can provide a uniform surface that includes photo-activatable coupling groups (filled diamonds 502) over the entire surface, e.g., inside and outside of the confinement (Step I). In a subsequent step (step II), the surface is exposed to activation radiation from a top side, e.g., the side away from the area where one wishes to immobilize the molecules of interest. The activated groups (open diamonds 504) are then inactivated (Step III) by capping them with another protecting group (filled circles 506), e.g., a non-removable protecting group. Subsequently, the ZMWs are illuminated from the bottom, so that the illumination volume includes the desired regions and coupling groups in that region are activated (Step IV, open diamonds 508). The molecules of interest are then coupled to these activated groups. By controlling the initial activation illumination, one can effectively control the amount of activatable groups that are capped prior to the later activation step. In particular, by using activation radiation, or a waveguide geometry or other exposure conditions, that permit activation radiation to effectively propagate more than half way through the core of the waveguide, in the first activation step, one may effectively cap more than half of the activatable groups in the first activation and capping step. By then directing activation radiation from the bottom side, substantially all of the remaining activatable groups, which are primarily substantially disposed toward the bottom of the core which would not have been activated and capped in the first steps, may then be activated and made available for coupling to the molecules of interest. As will be appreciated, the various approaches described above may be combined to further enhance selectivity.

In an alternative process schematically similar to the photoactivation methods described above, deep UV etching processes may be employed in generating an active surface in desired regions, e.g., at the bottom surface of a ZMW. In particular, deep UV exposure, e.g., illumination at below 200 nm, i.e., using deep UV lasers, deep UV lamps, e.g., Xeradex excimer lamp, under vacuum has been used to selectively degrade surface bound organic or inorganic materials, as such UV exposure is capable of breaking chemical bonds directly, e.g., without assistance from oxygen radicals which may be formed during the process, which may contribute to excessive etching. By performing such exposure under vacuum or other restrictions on the ability of oxygen radicals to contact and etch other surfaces, one can irradiate and consequently controllably remove organic and inorganic materials from selected substrate regions.

In the context of the surfaces of the invention, for example, a ZMW substrate may be provided with a first blocking layer that is substantially inert to additional coupling groups, e.g., it is non-reactive with the coupling strategy to be employed in eventually joining the molecules of interest to the surface. As a result, the functional groups on the original surface are effectively blocked by this blocking layer. Examples of blocking layers include organosilanes, such as PEG-silane, deep UV resists, or other long chain organosilanes. Exposure of the waveguides from the bottom or substrate side to deep UV radiation then degrades the blocking layer within the waveguides and preferentially at the bottom surface of the waveguide.

During the exposure or etching process, it may be desirable to limit the ability for oxygen radicals to contact other portions of the surface, e.g., outside of the ZMW or outside the observation region toward the bottom of the ZMW. In such cases, the system may be operated under vacuum, or alternatively or additionally, a sealing layer may be provided over the ZMW. Such sealing layer may comprise a rigid layer, e.g., a glass or silicon wafer or a more flexible material, such as a polymer sheet, e.g., PDMS, PTFE, polypropylene, polyethylene, polystyrene, or any of a variety of polymeric materials that are capable of sealing the waveguide structures, preferably without excessive off-gassing or otherwise contributing undesired chemical residues to the waveguides.

Following exposure, the substrate is contacted with a material that includes the functional groups used to couple the molecule of interest, which binds preferentially to the unblocked region, e.g., the exposed silanol groups uncovered by the 'etching' process. This additional material may include only functionalized groups or it may include a mixture of functionalized and inert groups in order to control density of functional groups, and consequently, molecules of interest within the waveguide structure. Such functionalized groups may be reactive chemical species and/or specific binding moieties, such as avidin, biotin, or the like.

Once the appropriate density of coupling groups is deposited in the desired regions, e.g., at the bottom surface of the waveguide structure, the molecule of interest may be coupled to the coupling groups, e.g., through the reactive group or through an appended biotin or avidin group or other specific binding partner to the coupling group or that is linked to the coupling group.

In another process similar to the photoactivation methods described above, tethered or grafted photoinitiators are employed. Of particular interest are photo-iniferters such as dithiocarbamates (DTC) which initiate and control the radical polymerization of acrylates, alkenes or the terminal radical addition of a capping reagent with a ligand for specific immobilization of the molecule of interest. The desired region (or regions) of a surface coated with the photoinitiator is illuminated to initiate the reaction only in that region. For example, a hydroxylated silicon substrate can be treated with a photo-iniferter such as N,N-(diethylamino)dithiocarbamoylbenzyl (trimethoxy)-silane (SBDC), which forms a self-assembled monolayer on the surface of the substrate. A methyl-methacrylate solution is then supplied, and UV irradiation of the desired region of the surface initiates polymerization to form a surface-tethered polymer brush of PMMA (e.g., including a coupling group) only in that region.

Another method of selectively immobilizing molecules of interest in desired regions on substrate surfaces involves the selective patterning of materials with different characteristics in different regions and relying upon the differing characteristics of the surfaces in the selective immobilization process. In the exemplary ZMW substrates described herein (as well as in other hybrid substrate types, e.g., metal or semiconductor based sensors that rely on surface associated molecules of interest, e.g., ChemFETS), such patterned hybrid surfaces already exist. In particular, ZMW substrates typically comprise a metal cladding layer, e.g., aluminum typically including an aluminum oxide surface layer, deposited over a silica based layer, e.g., $SiO_2$, with an aperture disposed through the cladding layer atop the $SiO_2$ layer. The resulting structure of the waveguides includes metal or metal oxide walls, e.g., $Al_2O_3$ with a $SiO_2$ base. The aluminum oxide surface is typically relatively highly positively charged in aqueous solutions while the $SiO_2$ surface carries a substantial negative charge. Such charge differentials may be readily employed to selectively localize and immobilize molecules of interest upon one surface relative to the other.

By way of example, DNA polymerase enzymes typically possess a relatively high level of positively charged surface residues. As a result, a polymerase will generally be repelled by the positively charged metal cladding layer while being attracted and adsorbing to the negatively charged glass surface at the base of a waveguide structure. Coupling groups can be similarly deposited, and then polymerase (or another molecule of interest) coupled to the coupling groups. One may readily modify the relative attraction/repulsion of the different surfaces by adjusting the nature of the environment to alter the charge of the enzyme, e.g., ionic strength, pH, additives, etc., by modifying each surface to enhance or reduce the charge component on the surface or by electrically (dis)charging the metal, or by modifying the enzyme, coupling reagent, or other molecule of interest to adjust its level of surface charge, e.g., through mutation of the enzyme or through coupling to charged groups, e.g., polyions like polylysine, polyarginine, or the like. In one aspect, after deposition of the polymerase (or other group or molecule of interest) on the negatively charged surface, the positively charged surface is passivated by coating it with an agent such as bovine serum albumin (e.g., acetylated BSA), polyglutamate, a polyelectrolyte, a polyelectrolyte multilayer, a polyelectrolyte-PEG copolymer, a phosphonate, or a phosphate, as discussed in greater detail below. Such passivation can, for example, prevent nonspecific binding of nucleotide analogs to the positively charged metal walls of a ZMW core during single molecule nucleic acid sequencing applications. In a related aspect, passivation is accomplished prior to deposition of the polymerase (or other group or molecule of interest), and optionally facilitates selective deposition, e.g., by blocking polymerase binding to the walls.

As noted above, the surface charge of a material can, in some embodiments, be an active, tunable characteristic which can be addressed, e.g., by pH tuning and/or by external polarization of the surface. For example, tin oxide (a transparent material) can be doped to make it conductive, and its surface charge (polarization) can be modulated to a desired value.

Other surface selective chemistries may likewise be employed. For example, different phospholipid compositions have shown the ability, in the presence and absence of calcium, to form different levels of supported phospholipid bilayers on metal oxide surfaces and silicon dioxide based surfaces. By selecting the lipid composition and the presence or absence of calcium, one can target deposition of molecules, either as blocking or coupling groups, onto the different surface types. For example, one can select a phospholipid that has high binding selectivity for metal oxide surfaces and use it to block the metal portion of the surface. Alternatively, one can utilize a phospholipid with an appropriate coupling group that has high binding selectivity for the underlying glass substrate, and thus selectively couple additional groups to the transparent substrate. Examples of these selective phospholipid compositions are described in, e.g., Rossetti, et al., Langmuir. 2005; 21(14):6443-50, which is incorporated herein by reference in its entirety for all purposes. Briefly, phospholipid vesicles containing between 50% and 20% DOPS (dioleoyl phosphatidyl serine) in DOPC (dioleoyl phosphatidyl choline), added to a hybrid $TiO_2/SiO_2$ surface exhibit selective formation of the lipid bilayer on the $SiO_2$ surface in the absence of calcium, whereas calcium presence permits bilayer formation upon the $TiO_2$ surface as well.

As will be appreciated, one may employ the glass selective phospholipid bilayer (or other surface-selective composition) as the coupling groups or may use it as a masking layer for a subsequent blocking layer deposition upon the metallic layer. This would then be followed by removal of the lipid bilayer from the glass substrate followed by coupling of the molecules of interest.

Alternatively, physical/chemical differences between the different surfaces may be subjected to differential binding based upon specifically selective chemistries. For example, specific groups that associate with particular metal groups may be employed to selectively localize molecules to one surface relative to the other, e.g., gold/thiol chemistries, etc.

As another example, silanes (e.g., methoxy-silane reagents) form stable bonds with silica surfaces via Si—O—Si bond formation, but do not significantly modify aluminum or aluminum oxide surfaces under appropriately selected reaction conditions (e.g., vapor phase favors modification of silica surfaces, as do certain conditions in solution). Silanes, for example, silanes modified with coupling groups for attachment of enzymes or other molecules of interest (e.g., biotin-PEG-silanes such as those described in U.S. patent application Ser. No. 11/240,662 (now issued as U.S. Pat. No. 7,763,423)), can thus be used to selectively pattern hybrid substrates such as ZMWs that contain silica surfaces. Ellipsometry and contact angle measurements on Si surfaces previously modified with $Al_2O_3$ show undetectable levels of silane reagent deposition. In addition, fluorescently labeled neutravidin does not bind specifically to $Al_2O_3$-modified fused silica slides after biotin-PEG-silane deposition on the slides, while, in contrast, biotin-PEG-silane modification of fused silica slides (not modified with $Al_2O_3$) results in very high specificity of neutravidin binding via the biotin ligand. Such results demonstrate the feasibility of modifying only the fused silica bottom of a ZMW or similar device with little or no modification of the aluminum walls or top surface of the device, using methoxysilane reagents.

As another example, negatively charged surfaces can be selectively modified by adsorption of copolymers containing positive polyelectrolyte blocks and PEG-ylated (or similar anti-fouling) blocks. The polycationic blocks bind to regions of the device that are electronegative, and the PEG components provide a nonreactive surface to preclude nonspecific binding. Exemplary polyelectrolyte-PEG copolymers include PLL-PEG (poly(L-lysine)-poly(ethylene glycol)). The PEG groups, or a subset thereof, can include a coupling group such as biotin or the other groups described herein (see, e.g., U.S. patent application publication 2002/0128234 "Multifunctional Polymeric Surface Coatings in Analytic and Sensor Devices" by Hubbell et al., Huang et al. (2002) "Biotin-Derivatized Poly(L-lysine))-g-Poly(ethylene glycol): A Novel Polymeric Interface for Bioaffinity Sensing" Langmuir 18(1): 220-230). Thus, for example, the $SiO_2$ surfaces of a ZMW can be coated with PLL-PEG-biotin, and biotinylated polymerase can then be coupled to the bottom of the ZMW via avidin or streptavidin binding to the PLL-PEG-biotin.

In one aspect, selective immobilization of the molecule of interest on one type of material in a hybrid substrate (e.g., a ZMW) is complemented or facilitated by modification of the other type of material. For example, for a ZMW that is to be used in an application such as single-molecule nucleic acid sequencing, it is desirable to selectively immobilize the polymerase to the bottom silica surface of the ZMW, and it is also desirable to passivate the metal walls and top surface of the device (before or after immobilization of the polymerase). Unmodified aluminum or aluminum oxide ZMW surfaces, which as noted above tend to be positively charged in aqueous solution, can demonstrate undesirable nonspecific binding of proteins (such as neutravidin or streptavidin and polymerase), nucleotide analogs (e.g., through the analog's phosphate groups), and dyes (e.g., dyes with sulfonic or carboxylic acid groups). As noted above, such undesirable electrostatic interactions can be minimized by binding of passivating agents to the surface; additional examples of suitable passivating agents include, but are not limited to, anionic polyelectrolytes such as poly(styrenesulfonate) and poly(acrylic acid) and macromolecules such as heparin and alginine.

In some instances, however, the adsorption of anionic polyelectrolytes to a positively charged surface may result in overcompensation of the net charge of the surface, where adsorption of the polyanion results in a change in the net surface charge from positive to negative. This change in principle minimizes the nonspecific adsorption of nucleotide analogs or other negatively charged compounds to the surface, but has the disadvantage that many proteins (e.g., polymerases) have affinity for electronegative surfaces. Thus, an electronegative surface produced by such overcompensation may result in undesirably high levels of polymerase nonspecific binding. This problem can be addressed by using high salt immobilization conditions; however, the high salt-regime can cause swelling of the polyelectrolyte layer as well as partial loss of polyelectrolytes. In addition, coating of surfaces with polyelectrolytes is a dynamic process, and it is possible that the polymerase may eventually form stable activity-blocking complexes with the polyelectrolytes.

Figure 16:
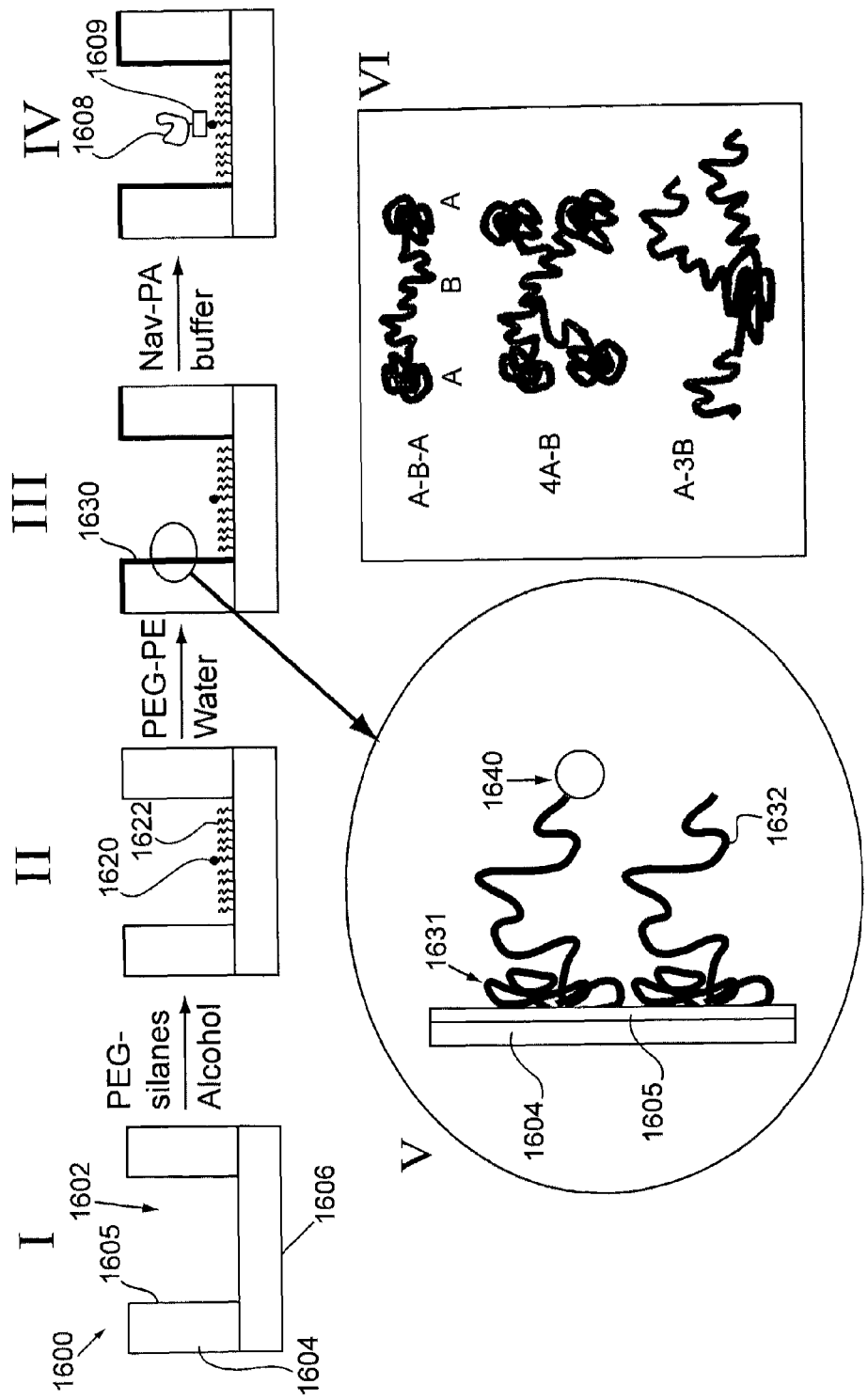
FIG. 16 I-VI schematically illustrates selective immobilization of molecules of interest by exploiting differing surface characteristics of different materials in hybrid substrates like ZMWs and passivation with a PE-PEG copolymer.

Optionally, instead of passivating the positively charged surface by adsorption of anionic polyelectrolytes, positively charged surfaces can be passivated by binding of copolymer structures containing polyelectrolyte blocks (negative) and PEG-ylated blocks. The polyelectrolyte blocks of the copolymer adsorb or anchor the macromolecules to regions of the device that are electropositive (e.g., the aluminum or aluminum oxide areas of a ZMW), and the PEG components provide a non-ionic cushion that precludes the surface attachment or the complexation of the polymerase with the polyelectrolyte blocks. The polyelectrolyte(PE)-PEG copolymers can, for example, be diblock (PEG-PE) or multiblock copolymers (e.g., PE-PEG-PE or PEG-PE-PEG), as well as branched polymers, comb polymers, or dendron-like polymers. A few exemplary linear and branched copolymers are schematically illustrated in FIG. 16 Panel VI. It will be evident that, while the exemplary copolymers described herein employ PEG, any anti-fouling backbone is applicable, for example, polypyrrolidone, polyvinyl alcohol, dextrans, and polyacrylamides. See, e.g., U.S. patent application publication 2002/0128234, Voros et al. (2003) "Polymer Cushions to Analyze Genes and Proteins" BioWorld 2:16-17, Huang et al. (2002) Langmuir 18(1): 220-230, and Zoulalian et al. (2006) J. Phys. Chem. B 110(51):25603-25605.

Orthogonal modification of a hybrid substrate with two compositions with different selectivities for different surface characteristics is schematically illustrated in FIG. 16. As shown in Panel I, ZMW 1600 includes core 1602 disposed through aluminum cladding layer 1604 to transparent silica substrate 1606. The aluminum core has a thin aluminum oxide layer 1605 on its surface. As shown in Panel II, the bottom surface of the ZMW is selectively modified with a mixture of biotin-PEG-silane 1620 and PEG-silane 1622 (e.g., at a ratio selected to provide a desired density of biotin coupling groups, and thus ultimately of molecules of interest, on the surface, optionally, one per core). As illustrated in Panel III, the walls and top surfaces of the device are then selectively modified with polyanion-PEG copolymer 1630. As shown in the expanded view in Panel V, copolymer 1630 includes polyanion (A) blocks 1631 and PEG (B) blocks 1632. (It is worth noting that modification of the aluminum surfaces optionally performed before, rather than after, modification of the silica surface.) Biotinylated polymerase 1608 is then bound via neutravidin 1609 to the biotin coupling group on biotin-PEG-silane 1620, as shown in Panel IV.

In one aspect, the compositions used to passivate the surface to which the molecule of interest is not attached (e.g., the aluminum surface) can also have a selected density of moieties that add functionality to the surface. For example, in the PE-PEG copolymers described above, fluorescence quenching moieties 1640 can be attached to the functional ends of the PEG blocks (FIG. 16 Panel V). As another example, orthogonal ligand schemes can be used to attach proteins to work in tandem with polymerases or other molecules of interest; e.g., in embodiments in which biotin is used to immobilize polymerase 1608, functional group 1640 can be a SNAP, HA, GST, or similar non-biotin coupling group, to bind a suitably modified second protein. These second proteins can be used to break up newly synthesized DNA chains, assist in removing reaction products from solution, assist in bringing reactants to the region of reaction, assist in regeneration of triplet quenchers, or the like.

Figure 17:
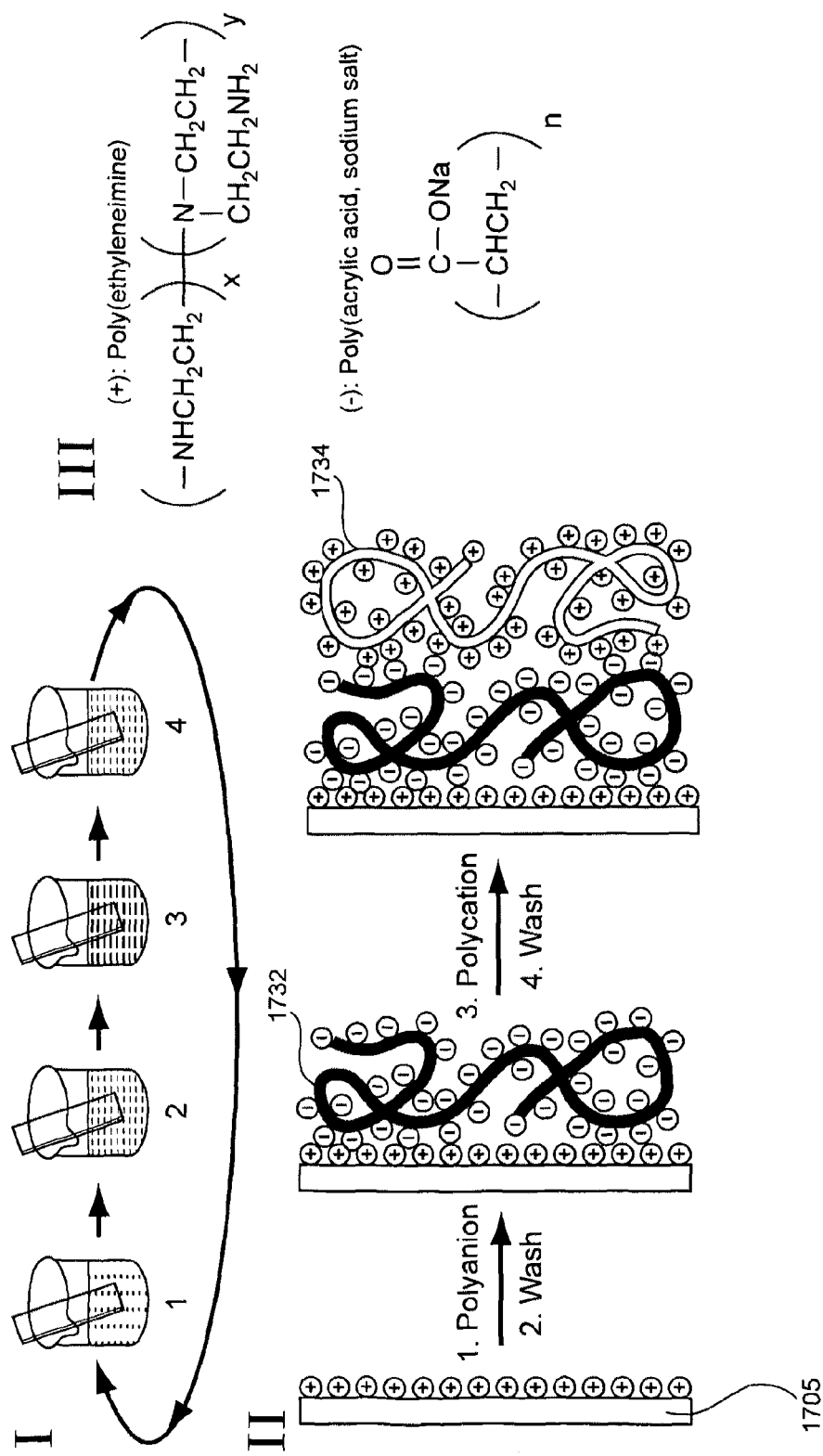
FIG. 17 I-III schematically illustrates formation of a polyelectrolyte multilayer.

As another example, the surface of the hybrid substrate to which the molecule of interest is not immobilized can be passivated using a polyelectrolyte multilayer. Polyelectrolyte multilayers are conveniently formed through successive deposition of alternating layers of polyelectrolytes of opposite charge. See, e.g., Decher (1997) Science 277:1232. Formation of a polyelectrolyte multilayer is schematically illustrated in FIG. 17. As shown in Panels I and II, in step 1 positively charged substrate 1705 is contacted with polyanion 1732, which adsorbs to the surface of the substrate. Excess polyanion is washed away in step 2. In step 3, a layer of polycation 1734 is deposited over the layer of polyanion 1732 formed in step 1; excess polycation is washed away in step 4. Steps 1-2 and/or 3-4 are repeated as desired, to deposit alternating layers of oppositely charged polyelectrolytes and form multilayers of essentially any desired thickness and resulting surface charge (negative when the polyanion is deposited last, or positive when the polycation is deposited last). Panel III illustrates exemplary polycation poly(ethyleneimine) and exemplary polyanion poly(acrylic acid), which are optionally employed to form polyelectrolyte multilayers.

Optionally, the final layer in a polyelectrolyte multilayer comprises a polyelectrolyte-PEG copolymer, for example, a copolymer such as those described above containing polyelectrolyte blocks (either positive or negative, depending on the charge of the preceding layer in the multilayer) and PEGylated blocks. As just one example, a poly(acrylic acid) layer in a polyelectrolyte multilayer can be followed by a layer of PLL-PEG or polyglutamate-PEG, to provide a PEG finish. It will be evident that, while the exemplary copolymers described herein employ PEG, any anti-fouling backbone is applicable, for example, polypyrrolidone, polyvinyl alcohol, dextrans, and polyacrylamides.

Figure 18:
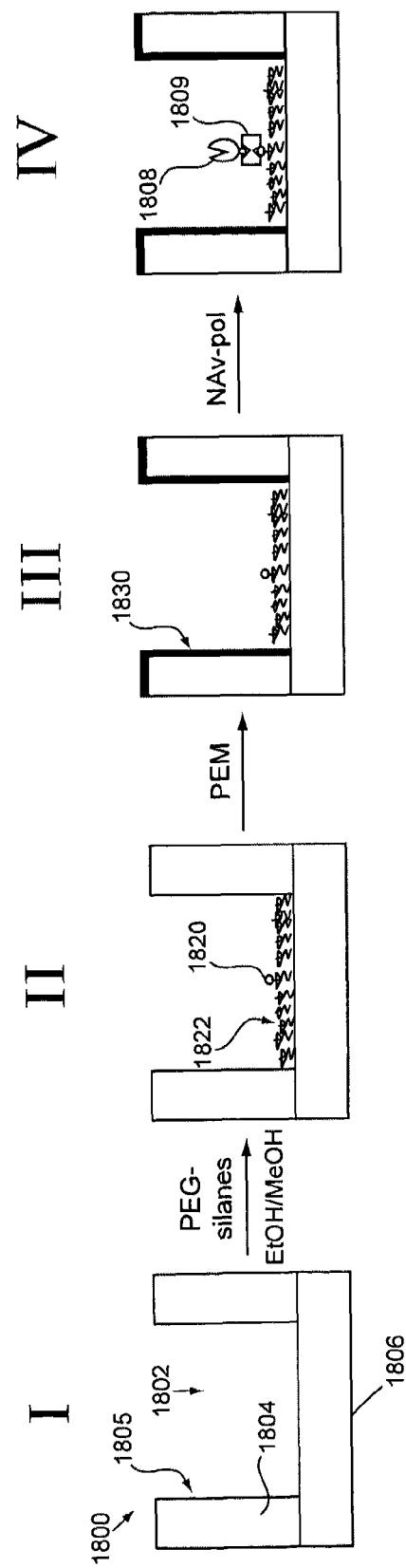
FIG. 18 I-IV schematically illustrates selective immobilization of molecules of interest by exploiting differing surface characteristics of different materials in hybrid substrates like ZMWs and passivation with a polyelectrolyte multilayer.

Differential surface derivatization of a hybrid substrate with two compositions having different selectivities for different surface characteristics and formation of a polyelectrolyte multilayer is schematically illustrated in FIG. 18. As shown in Panel I, ZMW 1800 includes core 1802 disposed through aluminum cladding layer 1804 to transparent fused silica layer 1806. The aluminum walls have a thin aluminum oxide layer 1805 on their surface. As shown in Panel II, the bottom surface of the ZMW is selectively modified with a mixture of biotin-PEG-silane 1820 and PEG-silane 1822. As illustrated in Panel III, polyelectrolyte multilayer 1830 is then deposited on the walls and top surfaces of the device. The polyelectrolyte multilayer can be deposited as illustrated in FIG. 17, for example; a layer of polyanion (e.g., poly(acrylic acid)) is deposited on the positively charged aluminum oxide layer 1805, followed by a layer of polycation (e.g., poly (ethyleneimine)), then another layer of polyanion, etc. For single molecule sequencing or similar applications, the final layer of the polyelectrolyte multilayer is typically a polyanionic layer, such that the surface of the polyelectrolyte multilayer is negatively charged to repel nucleotide analogs (or optionally a polyelectrolyte-PEG copolymer or similar, again to provide a surface with low binding to the analogs). As shown in panel IV, biotinylated polymerase 1808 is then bound via neutravidin 1809 to the biotin coupling group on biotin-PEG-silane 1820. Such exploitation of the differences in surface properties of the materials constituting a ZMW, e.g., silanization specific to the glass bottom and passivation of the sides and top aluminum oxide surfaces with polyelectrolyte multilayers to prevent nonspecific binding, can limit polymerase occupancy to the ZMW bottom, avoiding polymerase occupancy on side wall and top surfaces while limiting nonspecific binding of nucleotide analogs or the like.

As yet another example of ways in which the different materials in a hybrid substrate can be differentially modified based on their different surface characteristics, phosphate and phosphonic acid compounds can be employed (as can other compounds that exhibit surface specific chemisorption and/or self-assembled monolayer formation). Phosphate or phosphonic acid moieties bind strongly to metal oxides (e.g., aluminum oxide, titanium oxide, zirconium oxide, tantalum oxide, niobium oxide, iron oxide, and tin oxide) but do not bind strongly to silicon oxide. Thus, compounds that comprise at least one phosphate group (—OP(O)(OH)$_2$, whether protonated, partially or completely deprotonated, and/or partially or completely neutralized) or phosphonic acid group (—P(O)(OH)$_2$, whether protonated, partially or completely deprotonated, and/or partially or completely neutralized) can be used to selectively modify the aluminum oxide surfaces of a ZMW or similar hybrid substrate.

For example, a metal oxide surface can be modified with an alkyl phosphate or an alkyl phosphonate. (The terms phosphonic acid and phosphonate are used interchangeably herein.) Exemplary alkyl phosphates and alkyl phosphonates include, but are not limited to, an alkyl phosphate or alkyl phosphonate in which the alkyl group is a straight chain unsubstituted alkyl group (e.g., a straight chain alkyl group having from 1 to 26 carbons, e.g., from 8 to 20 carbons, e.g., from 12 to 18 carbons). Additional exemplary alkyl phosphates and alkyl phosphonates include functionalized or substituted alkyl phosphonates and alkyl phosphates, for example, functionalized X-alkyl-phosphonates and X-alkyl-phosphates where X is a terminal group comprising or consisting of a vinyl (CH$_2$), methyl (CH$_3$), amine (NH$_2$), alcohol (CH$_2$OH), epoxide, acrylate, methacrylate, thiol, carboxylate, active ester (NHS-ester), maleimide, halide, phosphonate, or phosphate group, or an ethylene glycol (EG) oligomer (EG4, EG6, EG8) or polyethylene glycol (PEG), photo-initiator (e.g., photo-iniferters such as dithiocarbamates (DTC)), photocaged group, or photoreactive group (e.g., psoralen). The alkyl chain spacer in the X-alkyl-phosphonate or X-alkyl-phosphate molecule is a hydrophobic tether that optionally has 1 to 26 methylene (CH$_2$) repeat units, preferably from 8 to 20, and more preferably from 12 to 18. The alkyl chain may contain one or more (up to all) fluorinated groups and/or can instead be a hydrocarbon chain with one or more double or triple bonds along the chain. The X-alkyl-phosphate or X-alkyl-phosphonate layer can furthermore be used as a substrate to anchor other ligands or components of the surface stack, such as a polyelectrolyte multilayer or chemisorbed multilayer. The alkyl phosphates/phosphonates can form a stable, solvent resistant self-assembled monolayer that can protect the underlying material (e.g., aluminum) from corrosion etc.; the role of the alkyl tether in the above structures is to enhance the lateral stability of the chemisorbed monolayer in aqueous environments. In embodiments in which the phosphonate or phosphate compound includes an unsaturated hydrocarbon chain, the double or triple bond(s) can serve as lateral crosslinking moieties to stabilize a self-assembled monolayer comprising the compound.

Specific exemplary alkyl phosphates and alkyl phosphonates include, but are not limited to, octyl phosphonic acid, decyl phosphonic acid, dodecyl phosphonic acid, hexadecyl phosphonic acid, octadecyl phosphonic acid, docosyl phosphonic acid (i.e., C22 phosphonic acid), hydroxy-dodecyl phosphonic acid (HO(CH$_2$)$_{12}$P(O)(OH)$_2$), hydroxy-undecenyl-phosphonic acid, decanediylbis(phosphonic acid), dodecylphosphate, and hydroxy-dodecylphosphate. Ellipsometry and/or contact angle measurements show that octyl phosphonic acid, octadecyl phosphonic acid, hydroxy-dodecyl phosphonic acid, and dodecyl phosphonic acid exhibit specificity toward aluminum/aluminum oxide surfaces relative to Si/SiO$_2$ surfaces. Modification of metal oxides with such phosphates and phosphonates has been described, e.g., in Langmuir (2001) 17:3428, Chem. Mater. (2004) 16:5670; J. Phys. Chem. B (2005) 109:1441, Langmuir (2006) 22:6469, Langmuir (2006) 22:9254, Langmuir (2006) 22:3988, J. Phys. Chem. B (2003) 107:11726, J. Phys. Chem. B (2003) 107:5877, Langmuir (2001) 17:462, J. Phys. Chem. B (2006) 110:25603, Langmuir (2002) 18:3957, Langmuir (2002) 18:3537, and Langmuir (2001) 17:4014.

Metal oxide surfaces can similarly be modified with polyphosphates or polyphosphonates. Chemisorption, e.g., of polyphosphonates differs from the previous description of polyelectrolyte adsorption in that the ligands (phosphonic acid moieties) form a chemical complex with the substrate (e.g., alumina, zirconia, or titania). Such interaction is stronger and less reversible to salt exchange than are simple electrostatic interactions. Examples include, but are not limited to, PEG-phosphonates such as those described in Zoulalian et al. (2006) "Functionalization of titanium oxide surfaces by means of poly(alkyl-phosphonates)" J. Phys. Chem. B 110 (51):25603-25605 or PEG-polyvinyl(phosphonate) copolymers. (In general, copolymers including chemisorbing moieties plus PEG or other anti-fouling moieties are contemplated herein.)

Other suitable phosphonates include high molecular weight polymeric phosphonates such as polyvinylphosphonic acid (PVPA)

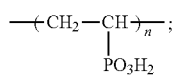

end-capped phosphonates such as

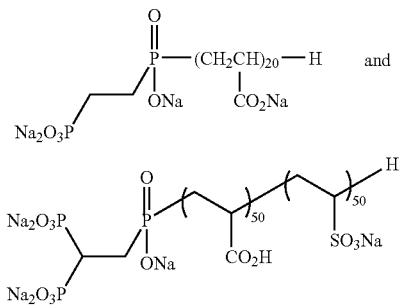

(commercially available from Rhodia as Aquarite® EC4020 and Aquarite® ESL, respectively); and copolymers such as vinyl phosphonic acid-acrylic acid copolymer

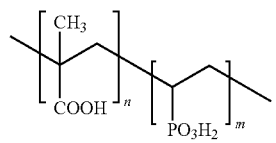

(commercially available from Rhodia as Albritect™ CP30).

Suitable phosphonates also include low molecular weight phosphonates such as 2-carboxyethyl phosphonic acid (also known as 3-phosphonopropionic acid; commercially available from Rhodia as Albritect™ PM2) and the compounds listed in Table 1 (commercially available as Dequest® compounds from Solutia, Inc., St. Louis Mo.). Phosphonate compounds can be supplied as salts (e.g., sodium, potassium, lithium, or ammonium salts) or, preferably, as free acids.

TABLE 1

Exemplary phosphonic acid compounds.

| Chemical Name | Structure |
|---|---|
| Amino tri (methylene phosphonic acid) | 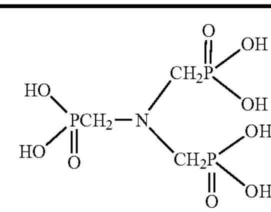 |
| 1-Hydroxyethylidene-1,1,-diphosphonic acid | 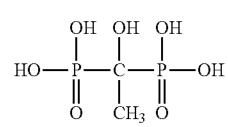 |

TABLE 1-continued

Exemplary phosphonic acid compounds.

| Chemical Name | Structure |
|---|---|
| Hexamethylenediaminetetra (methylenephosphonic acid) | (structure) |
| Diethylenetriamine penta(methylene phosphonic acid) | (structure) |
| ethylenediamine tetra(methylene phosphonic acid) | (structure) |
| bis(hexamethylene triamine penta(methylenephosphonic acid)) | |
| Amino methylene phosphonic acid | |
| 2-Phosphonobutane-1,2,4-tricarboxylic acid | (structure) |
| Monoethanloamine diphosphonate | |

A few exemplary uses of phosphonates and phosphates follow, with respect to treatment of a ZMW where a molecule of interest such as a polymerase is to be immobilized selectively on the bottom, silica surface of the ZMW waveguide cores. It will be evident that similar considerations apply to treatment of other hybrid substrates. As one example, a ZMW chip can be treated with a phosphonate to passivate the aluminum oxide surface of the ZMW, and a positively charged polymerase can then be immobilized by selective binding to the negatively charged silica surface. Similarly, the ZMW chip can be treated with a phosphonate, a capture reagent that can be used for subsequent immobilization of the polymerase (e.g., neutravidin) can be immobilized by binding to the silica surface, and then the polymerase can be immobilized by binding to the capture agent. In these examples, the phosphonate passivates the aluminum oxide surface, providing bias (e.g., by blocking the aluminum oxide) and providing a surface with low nonspecific binding of nucleotide analogs, etc. In related examples, after immobilization of the polymerase or the capture agent, a polyelectrolyte multilayer is formed on the aluminum oxide surfaces to passivate them. Phosphonates and phosphates can also be employed in combination with compounds that selectively modify the silica surfaces of the ZMW. Thus, for example, the aluminum oxide surface can be passivated and/or blocked with a phosphonate, and silane reagent(s) can then be employed to modify the silica surface (or vice versa, with modification of the silica surface preceding phosphonate deposition).

In one class of embodiments, the phosphate or phosphonate compound serves as the first layer on which a polyelectrolyte multilayer is built on the surface, e.g., by successive deposition of oppositely charged polyelectrolytes as described above. In a related class of embodiments, a chemisorbed multilayer is formed on the surface. The chemisorbed multilayer can include, e.g., alternating layers of a multiphosphonate-containing reagent (for example, a diphosphonate, such as 1,n-alkyl-diphosphonic acid, or a polyphosphonate, such as polyvinylphosphonate) and zirconium (IV) ligands. The zirconium (IV) ligand for the phosphonate can be provided by providing a precursor such as zirconium t-butoxide, zirconium acetylacetonate, or zirconium ethoxide, from which the phosphonate displaces the ligand around the zirconium. The multilayers can be formed using methods well known in the art, for example, by alternately dipping the substrate or surface in a solution of the phosphonate and in a solution of the zirconium precursor (with an intermediate heat annealing step), or by alternating dipping in a solution of the phosphonate with organometallic chemical vapor deposition (MOCVD) or rapid thermal chemical vapor deposition (RT-CVD) of the zirconium (with an annealing step if necessary). Such chemisorbed multilayers are robust, and are similar to polyelectrolyte multilayers but with the advantage of having the equivalent of chemisorbed "cross-links" between adjacent layers rather than physical electrostatic ones as in polyelectrolyte multilayers.

In another aspect, thermodynamic or diffusion limited processes may be employed in the selective activation and/or deactivation of desired or non-desired regions. In particular, active coupling groups may be disposed over a substrate surface, including within ZMW structures, and may be provided in active form. They are then subsequently and selectively deactivated by exposing the substrate to capping or blocking groups that will prevent any additional coupling to those groups. Because the coupling groups that are present on the desired regions reside within the ZMW, e.g., at the bottom surface, diffusion of the capping or blocking agents to these groups is somewhat limited. As a result, those coupling groups will be less prone to being blocked (will likely be the last groups to be blocked), and may be used to couple the molecules of interest toward the bottom surface of the ZMW. In particular, by controlling the time of exposure of the substrate as a whole to the blocking agent, the concentration of the blocking agent, and other conditions of the capping reaction, e.g., temperature, etc., one can control the degree to which the coupling groups within the waveguide become blocked or capped. In this aspect of the invention, it will be appreciated that the blocking component need not specifically bind to particular coupling groups to prevent coupling of the molecule of interest. In some cases, such blocking or capping groups may prevent such binding through its presence within the waveguide or other portions of the surface. This may include hydrophobic or hydrophilic coating materials that may form a thin or monolayer over the surface and thus block binding of the molecule of interest, or which provide a spatial or steric barrier to binding at a given coupling group without actually binding to the active coupling component of the coupling groups.

Figure 6:
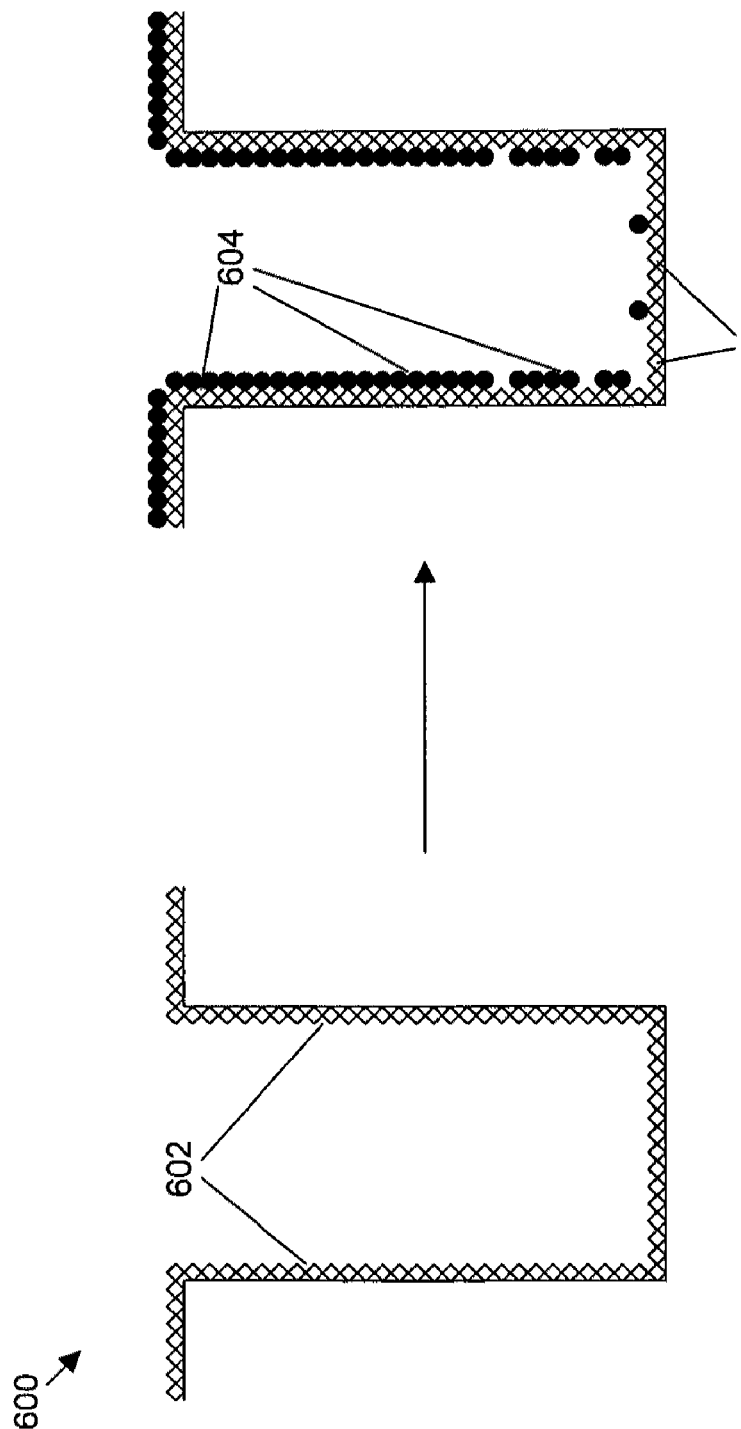
FIG. 6 provides a schematic illustration of a diffusion limited process for providing active surfaces within confined structures.

The foregoing aspects of the invention are schematically illustrated in FIG. 6. As shown, a waveguide structure 600 is provided with a uniform coating of coupling groups 602 disposed upon it (shown as open diamonds). Contacting the overall structure with capping groups 604 (shown as closed circles) results in diffusion limited capping within the waveguide structure, and as a result, leaves more active (uncapped) coupling groups 602 toward the bottom surface of the waveguide structure for coupling molecules of interest in a subsequent contacting step.

As will be appreciated, the initial step of providing active coupling groups over an entire surface may be avoided where one simply wishes to couple groups directly to the underlying surface, e.g., silanol groups on glass substrates, or the like. In particular, by initially blocking any active coupling groups on the surface for a relatively short period, those groups that are most accessible, e.g., not within the bottom regions of a ZMW, will be blocked first. A subsequent, longer exposure of the partially blocked or capped surface groups to coupling groups that are capable of binding to such surface groups will yield such coupling groups immobilized upon the bottom regions of the waveguide structures. The amount of time, concentration, temperature, and other conditions of each step may be varied to provide optimal conditions for each of the blocking steps and coupling steps, and may be determined based upon readily identifiable characteristics and simple experimentation.

An alternative approach to additively providing molecules of interest in a desired location is through the optical trapping of the molecule in the desired location, e.g., using optical "tweezer" techniques. In particular, using the strongly enhanced electric field created by focused laser energy within an optical confinement, such as a ZMW, one may enhance the concentration of particles such as molecules of interest, or enrich for their presence within the focal region of a ZMW and subsequently couple it to a binding group located within that region. The molecule of interest may be provided coupled to additional groups, e.g., avidin, streptavidin, neutravidin, biotin, or particles, such as beads, e.g., heparin sparse beads, or the like, etc., in order to provide a sufficiently large particle for trapping. The use of such optical trapping/enhancement techniques has been described in detail for exerting trapping forces on particles as small as 10 nm. See, e.g., Novotny, et al., Phys. Rev. Letts. 79(4):645-648 (July 1997), which is incorporated herein by reference in its entirety for all purposes.

As an alternative or additional process to the selective activation/deactivation processes discussed above, or below, the present invention optionally or additionally may include an initial patterning step to provide neutral or inert groups upon areas where it is not desired to couple the molecules of interest. Such patterning typically provides a coarse selectivity to the localization, in that it is not specifically intended to yield the final selective surface. For example, in the context of micro or nanowells, or other structures provided in an otherwise planar surface, inert groups may be printed, applied or otherwise patterned upon the upper planar surface of the substrate without depositing such materials into the nanostructures, e.g., ZMWs. By first blocking the non-relevant surfaces with inert groups, one can then deposit and couple active groups within the relevant areas. Again, in the context of a ZMW array, depending upon the density of the array, e.g., the percentage of overall substrate occupied by waveguide structures, a substantial amount of non-relevant surface can be blocked and thus prevented from harboring molecules of interest that might otherwise interfere with the ultimate application of the device, e.g., through substrate depletion, excessive product formation, etc.

Figure 7:
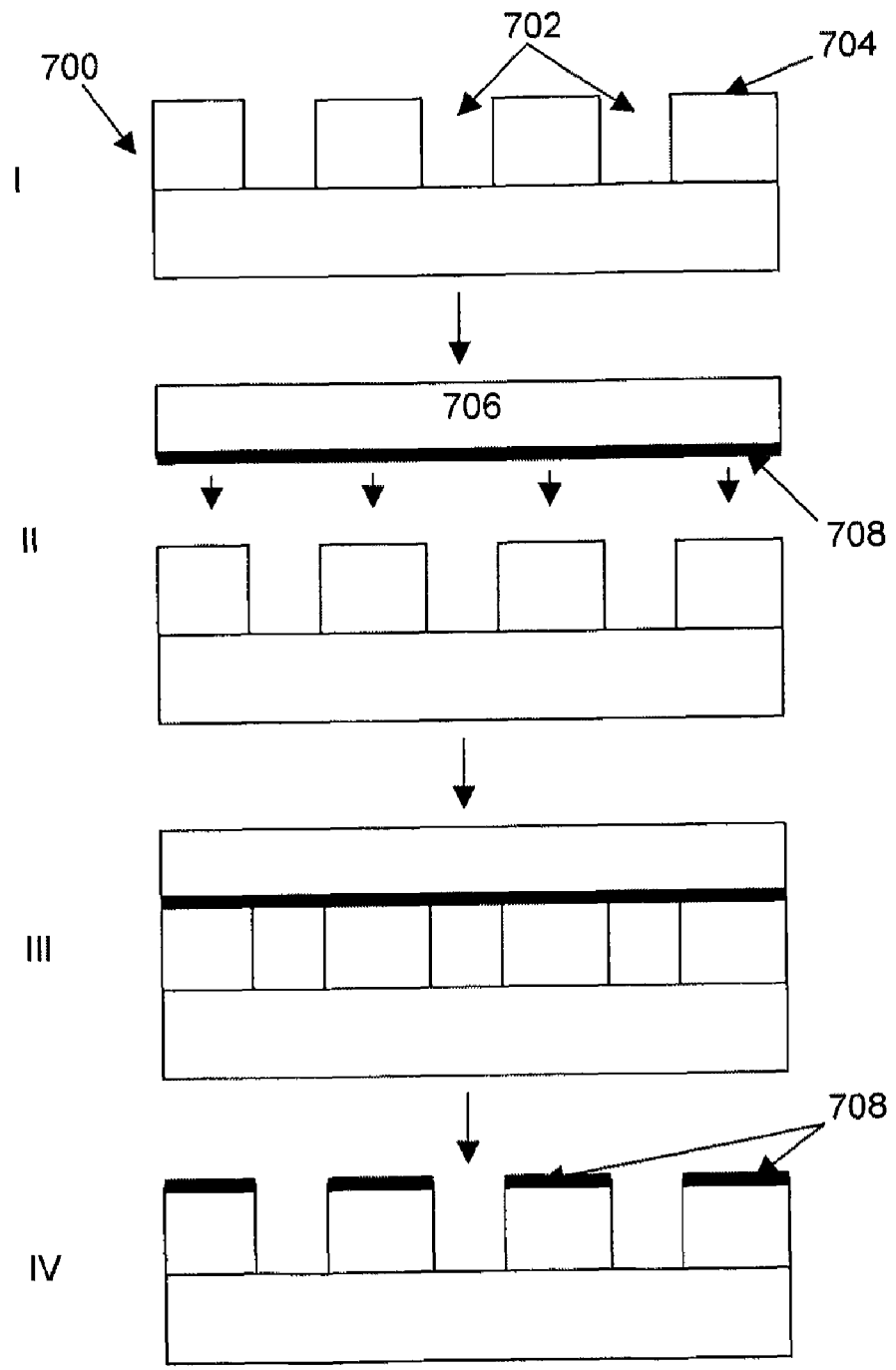
FIG. 7 I-IV provides an illustration of process for providing a printed masking layer on non-relevant surfaces of substrates.

Such patterning may include simple stamping of the inert molecules onto a surface whereby the inert groups will not penetrate the depressions on that surface, or it may involve more complex printing patterns using either nanolithographically produced stamps to provide selective deposition, ink jet printing, or the like, to selectively deposit inert groups upon the overall substrate surface. An example of the process of the invention is schematically illustrated in FIG. 7.

As shown, a substrate 700 that includes an array of ZMWs 702 disposed in its surface 704 (in panel I), is contacted with a separate substrate 706 bearing a printable material 708 thereon that prevents coupling of active functional groups to the substrate surface 704 (Panel II). By contacting surface 704 with the printable material 708, the material is transferred to the surface 704 while not penetrating ZMWs 702 (Panels III and IV). As a result, subsequent coupling of molecules of interest to the upper surface 704 of substrate 700 is blocked. The printable material may include any of a variety of different materials, including, e.g., inert surface associating groups that simply cap any active groups on the surface. Alternatively, such material may include coating materials that prevent association with the molecules of interest, e.g., hydrophobic or hydrophilic materials, highly charged materials that repel any binding or other association, or materials that provide an impenetrable barrier to such materials, e.g., polymer coatings, resists, or the like.

As will be appreciated, any of the foregoing processes may be practiced in conjunction with other processes described herein to further enhance surface selectivity and/or localization.

III. Subtractive Processes

As noted previously, in alternative aspects, subtractive processes are employed to provide the molecule(s) of interest in the desired regions of a substrate and at the desired concentration and/or density of molecules. As noted, subtractive processes are generally characterized and differentiated from the additive processes described above, in that they deposit the molecule of interest more ubiquitously, e.g., over an entire substrate surface including in the desired regions. Subsequently, the excess molecules of interest, e.g., that are located in non-desired regions, are removed. A variety of different processes may be employed in such subtractive processes.

In one example, a process may be employed that is roughly the inverse of the photoactivatable processes described above. In particular, coupling of the molecule of interest may be accomplished over the substrate surface using a selectively cleavable linker or coupling group. A variety of photocleavable linker chemistries are known in the art and include 2-nitrobenzyl linkers (See, e.g., Rodebaugh, R.; Fraser-Reid, B.; Geysen, H. M. *Tetrahedron Lett.* 1997, 38, 7653-7656), as well as a number of other known photocleavable linker types, see e.g., *Org. Lett.*, 2 (15), 2315-2317, 2000.

In the context of the present invention, a coupling group may be broadly applied to a substrate surface using a photocleavable linker group. The molecule of interest is then coupled to the coupling groups substantially non-selectively. Selective illumination of areas that are outside the desired regions then releases the molecules of interest from these areas, leaving such molecules substantially only coupled within the desired regions. Washing of the substrate then removes the molecules from any potential interference with the desired application.

Figure 8:
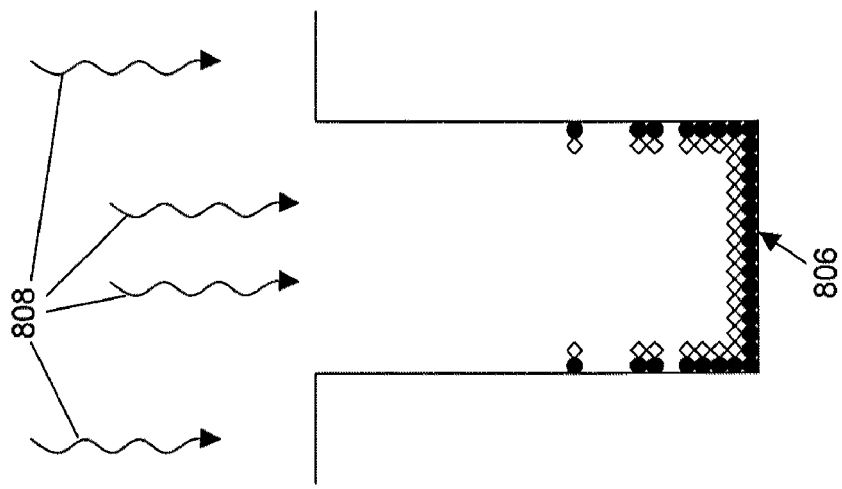
FIG. 8 schematically illustrates a photocleaving process for removing active groups from non-relevant portions of substrate surfaces.
Figure 8:
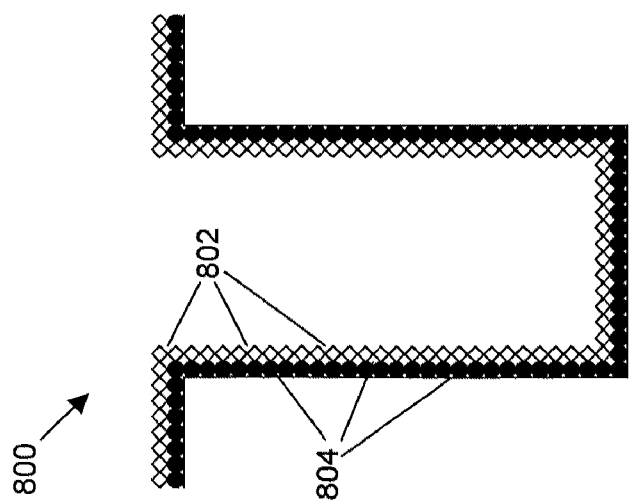

This aspect of the invention is schematically illustrated in FIG. 8. In particular, coupling groups 802 (shown as open diamonds) are provided in a uniform coating over the surface of the waveguide structure, but are attached to that surface through photocleavable linker groups 804 (shown as filled circles). The surface that is outside of the area of interest, e.g., not at the bottom surface 806 of ZMW core, is then exposed to light (shown as wavy arrows 808) to cleave the linker groups in the non-desired regions, where, coupling is not ultimately desired, leaving those coupling groups in the desired regions for subsequent coupling, e.g., at bottom surface 806, available for coupling.

Another subtractive approach to the selective immobilization of molecules of interest, particularly within nanostructured wells or other constrained spaces, e.g., optical confinements like ZMWs, utilizes deactivation components, e.g., that deactivate either the molecule of interest or the component linking that molecule to the surface, or otherwise cause the digestion, deactivation, release or removal of such molecules from the surface. For ease of discussion, such components are referred to herein as "deactivation components" regardless of whether such components degrade and/or digest the molecules of interest, inactivate such molecules, e.g., through nonreversible binding to active sites or other modification of such molecules of interest, or the like, or merely release them from the surface, e.g., through the cleavage of a linking group or otherwise.

Such approaches may rely upon thermodynamics to selectively avoid deactivation or removal within a ZMW, as diffusion of larger deactivation components, e.g., enzymes, i.e., proteases or other larger macromolecular compounds, or the like, will diffuse into a waveguide more slowly, similar to the diffusion limited capping of coupling groups shown in FIG. 6.

Alternatively, the method may rely upon the use of additional components to prevent the deactivation components from accessing the molecules of interest within the constrained space, e.g., a ZMW. One particularly preferred aspect of such prevention involves the coupling of the deactivation component to a large component, such as a bead or other particle, or a large polymeric molecule or aggregation of molecules, that are at least partially incapable of entering into the ZMW. Such larger components are generally referred to as exclusionary components as they are sized or shaped to be at least partially excluded from recesses such as ZMWs on substrates. Because the deactivation component is coupled to the exclusionary component, it is only capable or more capable of accessing molecules of interest that are exposed upon or proximal to the upper surface of the substrate incorporating the ZMW(s), and are thus accessible to the deactivation component, and not those molecules that are well within the structures.

Figure 9:
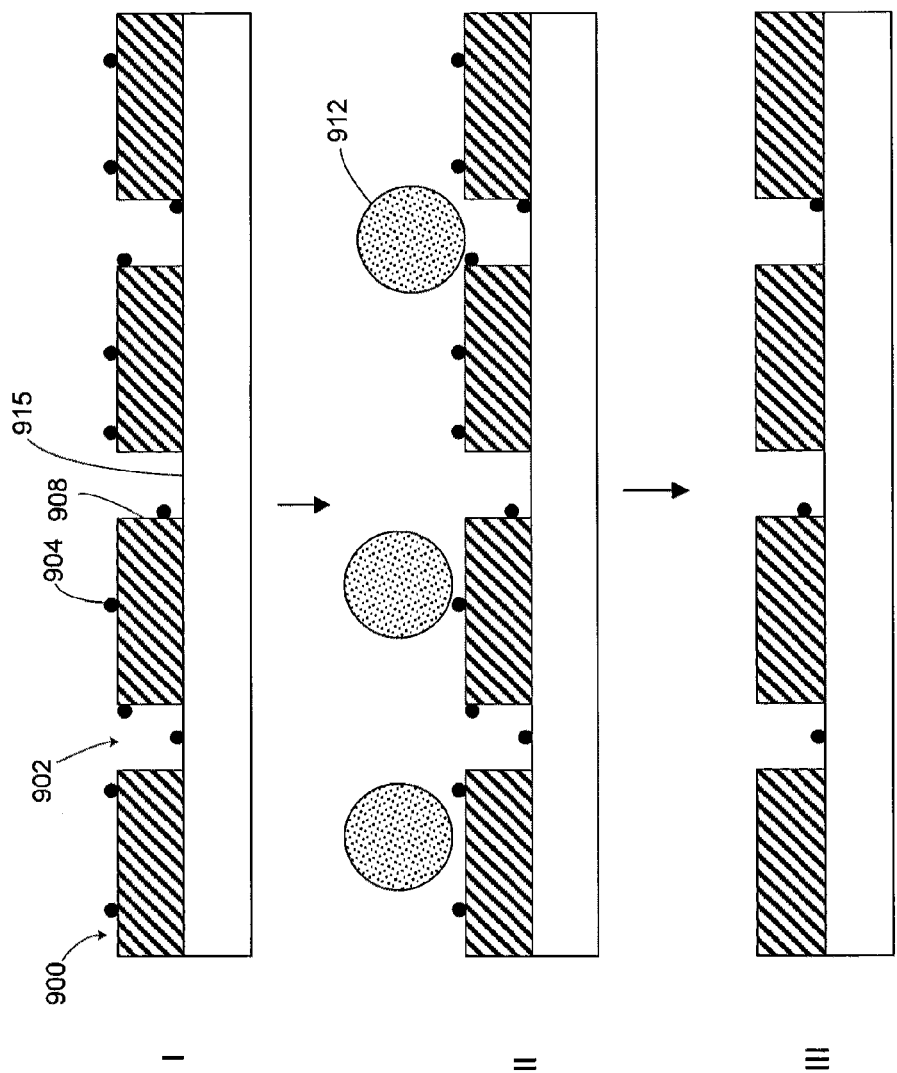
FIG. 9 I-III illustrates a size excluded particle based process for removing molecules of interest from non-relevant portions of substrate surfaces.

In accordance with this aspect of the invention, the deactivation component might include digestive molecules, e.g., proteases, such as serine proteases, i.e. proteinase. K, subtilisin, and the like, threonine proteases, aspartic acid proteases, cysteine proteases, metalloproteases, and glutamic acid proteases, e.g., for digestion, cleaving or release of protein or peptide based molecules of interest or linking components in either non-specific or specific fashion, e.g., using a target protease to cleave a particular linking molecule, e.g., a biotin. Alternatively, such deactivation components might include carbohydrate digesting enzymes (also termed carbohydrases), such as cellulases and amylases, or nucleases, such as exo- or endonucleases, etc., for the digestion or cleaving of carbohydrate or nucleic acid based linking molecules or the molecules of interest. This aspect of the invention is schematically illustrated in FIG. 9.

As shown, an array 900 of confining structures, e.g., ZMWs 902, is provided with molecules of interest 904 randomly deposited over its entire surface, e.g., including the surface of cladding layer 908 and substrate layer 915 (Step I). Large particles, such as beads 912, having deactivation components immobilized upon their surface (or components that otherwise deactivate, cleave or release the molecules of interest), are then contacted with the array 900. Because beads 912 are larger than the openings to the waveguides 902, the deactivation components immobilized on the beads are only capable of accessing and inactivating, digesting, cleaving or releasing molecules of interest that are deposited on surfaces outside the structures 902 or that are sufficiently proximal to the opening of such structures as to be accessible by the immobilized components on the beads 912. As a result, molecules upon or near the surface outside of the ZMW structures are removed or otherwise deactivated, leaving only those molecules that are well within the constrained or exclusionary space of the waveguide (Step III). This aspect of the invention is also further illustrated, below.

In related aspects, the beads may be provided with a binding or crosslinking component that binds or crosslinks with or to the molecule of interest. Subsequently, the bead may be mechanically removed from the surface taking at least a portion of the molecules of interest with it.

A variety of different types of beads may be used, including beads generally used in chemical and biochemical analyses, i.e., agarose, acrylic, silica, or polyacrylamide beads or the like, or other chromatographic or enzyme immobilization media/matrices, such as F7m or G3m matrices, available from MoBiTec, GmbH (Göttingen, Germany), magnetic beads or other metallic beads. Similarly, methods for linking the deactivation component to the beads may be varied to achieve desired results. For example, linker groups having varied lengths may be used to permit penetration of the deactivation component partially into a ZMW or other constrained space. Likewise, linker stiffness may be adjusted through the chemical structure and/or crosslinking of the linkers to provide greater or lesser ability for the deactivation component to enter into a confined space such as a ZMW.

In an alternative approach to the use of beads, other scaffold materials may be used to support the deactivation component and provide that component with accessibility to the upper surface of the overall substrate, and in some cases, a subset of the surfaces within recesses on that surface, e.g., a waveguide core. In particular, the scaffold component would result in the deactivation component being not entirely excluded from a given recess on the substrate surface, e.g., a zero mode waveguide core. By way of example, the deactivation component may be provided tethered or coupled to a scaffold or supporting molecule that is either only partially excluded from the recess or is only excluded when provided in certain orientations. For example, a rigid or semi-rigid linear molecule, such as a double stranded nucleic acid or other rigid or semi-rigid elongated polymer, may be used that includes the deactivation component, e.g., a protease, coupled to it at an intermediate position. The supporting molecule is provided of sufficient length that it can only move into the recess if oriented appropriately, e.g., lengthwise. As a result of entering the recess lengthwise or being retained upon the upper surface, only those molecules on the upper surface or within the recess but within reach of the deactivation component will be deactivated. By way of analogy, the supporting molecule and intermediate deactivation component function as a chimney sweep to remove molecules of interest from the upper surface of the substrate and a certain distance within the recesses, as dictated, at least in part, by the intermediate positioning of the deactivation component on the supporting molecule.

In the case of a relatively typical zero mode waveguide structure of approximately 100 nm in depth and 70 nm in diameter, for example, a double-stranded DNA oligonucleotide 150 nm in length could be used with the deactivation component, e.g., a protease or the like, affixed to it. Positioning and coupling are accomplished through covalent coupling chemistry to a nucleotide analog that has been inserted in the oligonucleotide sequence at a selected position a given distance from one or both ends. Because double-stranded DNA is mechanically rigid, the center portion of the oligonucleotide to which the deactivation component is affixed is away from the end of the supporting molecule. Upon entry into a waveguide core, only the end of the supporting double stranded DNA molecule will be able to reach the bottom of the core, and thus the deactivation component will be geometrically constrained away from the bottom of the core, or other confined space. Thus, molecules of interest that are on the top surface or on the side walls of (for example) a ZMW would be removed, while a molecule of interest on or near the floor of the ZMW, e.g., within the illumination volume, would remain. Positional coupling of deactivation components to double stranded nucleic acids may be carried out by a variety of methods. For example, in the case of coupling proteins, such as proteases or other enzymes, to nucleic acid supporting molecules, a protease or other enzyme can be maleimide activated by conjugation with a bifunctional crosslinker such as GMBS (available from PIERCE). This maleimide-activated protein can be directly coupled to a single strand or double strand of DNA possessing an internal thiol modification (e.g., a THSS internally labeled molecule available from, e.g., Operon, Inc.). The thiol modification is capped via a disulfide which is removed during the conjugation by TCEP (also available from PIERCE). Similarly, a nucleic acid with an internal thiol can be conjugated with a heterobifunctional crosslinker (e.g., MAL-NHS, maleimide-N-hydroxysuccinimide) and then conjugated to a protease via an amine-NHS reaction. Similar reactions can be employed to conjugate amino-modified DNA to a protease with thiols available on or near its surface.

Figure 13:
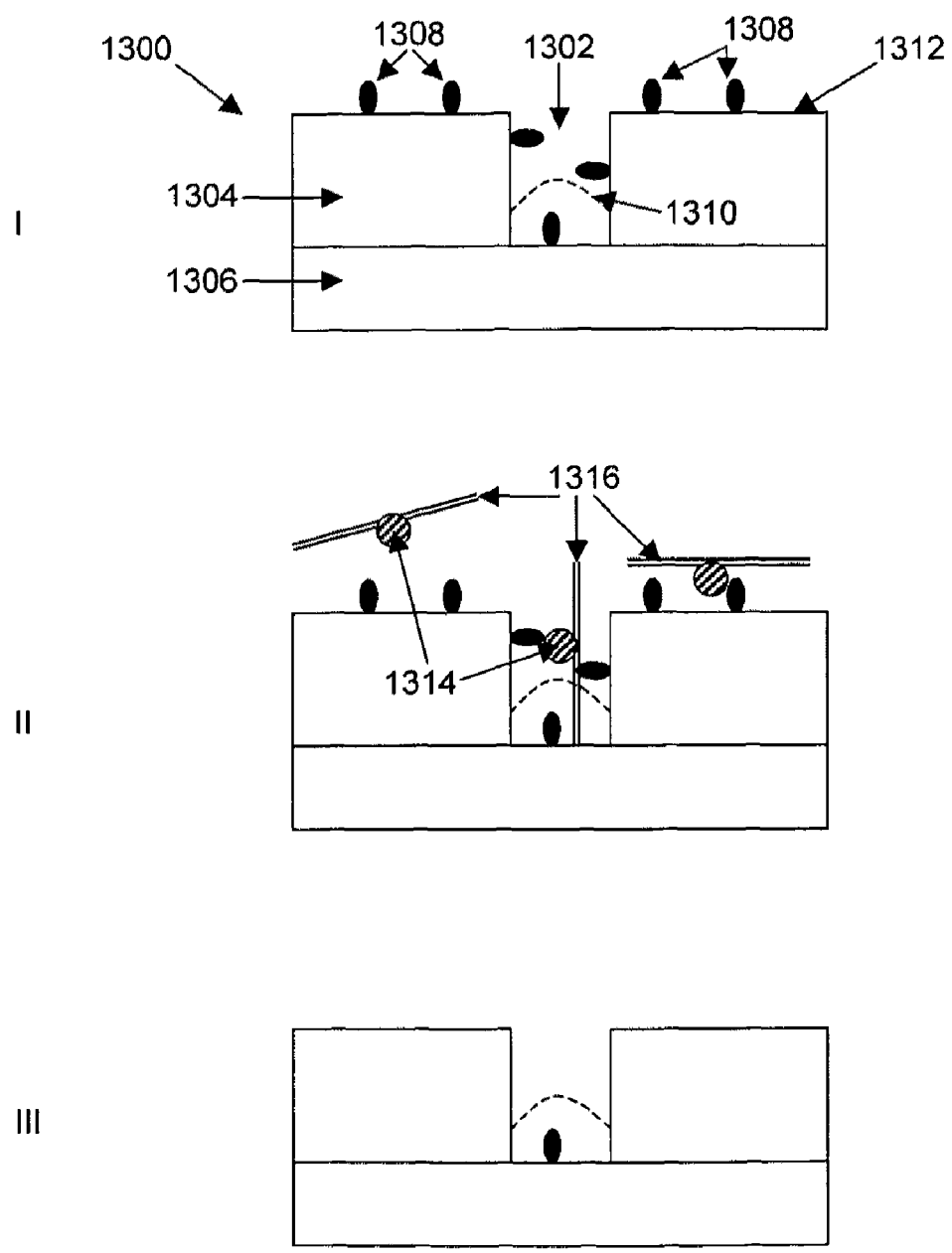
FIG. 13 I-III schematically illustrates a process for selective localization of molecules using an alternate exclusionary process.

The foregoing process is schematically illustrated in FIG. 13. As shown, a ZMW device 1300 includes a core 1302 disposed within a cladding layer 1304, again extending to an underlying transparent substrate 1306. As shown in panel I, a number of active molecules of interest, e.g., polymerase molecules 1308, are adsorbed or otherwise coupled to the surface of the overall substrate, including both within a desired illumination region (as indicated by dashed line 1310), on upper surface 1312 and at the upper wall surfaces of the core 1302. In the context of the invention, and as shown in panel II, a deactivation component, such as protease molecule 1314, is coupled at an intermediate position to a rigid, linear or elongated supporting molecule, such as dsDNA molecule 1316. Because of its size and structural rigidity, the supporting molecule 1316 with associated deactivation component 1314 only penetrates the core 1302 of the waveguide structure 1300 in an end-on orientation, or it lays across the upper surface 1312 of the overall structure. As a result of this, only polymerases that are disposed upon the upper surface or within reach of the deactivation component that penetrates a partial distance into the waveguide core will be potentially affected by the deactivation component. As such, polymerase molecules that are disposed at or near the bottom surface of the waveguide core, e.g., within the illumination region, will be spared deactivation (Panel III). As will be appreciated, the positioning of the deactivation component and/or the rigidity of the supporting molecule may generally be chosen to adjust the depth within a core structure at which deactivation can occur.

As noted above, the deactivation component is optionally a protease such as Proteinase K that nonspecifically digests the active molecule or a coupling group etc., thereby removing it from the surface of the substrate. In other embodiments, the deactivation component is a site-specific protease (e.g., enterokinase, thrombin, TEV protease, or any of the variety of other site-specific proteases available in the art). Use of a site-specific protease can avoid autoproteolytic cleavage of the protease from the exclusionary component, which would release soluble active protease able to undesirably access the optimal confined illumination volume of the structures.

An exemplary embodiment employing a site-specific protease is schematically illustrated in FIG. 14. As shown, a ZMW device 1400 includes a core 1402 disposed within a cladding layer 1404, again extending to an underlying transparent layer 1406. In this example, polymerase molecule 1408 is covalently linked to biotin 1420 through peptide linker 1421, which includes a cleavage recognition site for site-specific protease 1415. Binding of biotin 1420 to streptavidin 1409, which is in turn bound to biotin 1422 that is adsorbed or otherwise coupled to the surface of the substrate, couples polymerase 1408 to the surface. As shown in panel I, a number of active molecules of interest, e.g., polymerase molecules 1408, are coupled to the surface of the overall substrate, including both within a desired illumination region (as indicated by dashed line 1410) and at the upper wall surfaces of the core 1402 (and optionally also on upper surface 1412). As shown in Panel II, cleavage of linker 1421 by protease 1415 releases polymerase 1408 from the surface. The site-specific protease molecule 1415 is coupled at an intermediate position to a rigid, linear or elongated supporting molecule, such as dsDNA molecule 1416. As for the embodiments described above, because of its size and structural rigidity, the exclusionary component 1416 with associated protease 1415 only penetrates the core 1402 of the waveguide structure 1400 in an end-on orientation, or it lies across the upper surface 1412 of the overall structure. As a result of this, only polymerases that are disposed upon the upper surface or within reach of the deactivation component that penetrates a partial distance into the waveguide core are potentially affected by the deactivation component. As such, polymerase molecules that are disposed at or near the bottom surface of the waveguide core, e.g., within the illumination region, will remain attached to the surface since their linkers are inaccessible to the protease and are not cleaved.

Another exemplary embodiment employing a site-specific protease is schematically illustrated in FIG. 15. As shown, ZMW device 1500 includes core 1502 disposed within cladding layer 1504 that extends to underlying transparent layer 1506. In this example, as illustrated in Panel I, biotin coupling group 1522 is coupled to the surface of the overall substrate via peptide linker 1521, which includes a cleavage recognition site for site-specific protease 1515. Cleavage of linker 1521 by protease 1515 releases biotin 1522 from the surface. Since protease 1515 is coupled to exclusionary component double-stranded DNA 1516, as shown in Panel II the protease removes biotin 1522 from the surface everywhere except the lowest portion of core 1502. As shown in Panel III, streptavidin 1509 (or neutravidin etc.) and polymerase 1508 coupled to biotin 1520 are then deposited on the substrate and are retained by binding to biotin 1522 only in optimal confined illumination volume 1510.

Another alternative subtractive method for the selective localization of molecules of interest involves the use of that molecule's own activity against it within the undesired regions. For example, in the case of immobilized nucleic acid polymerase enzymes, it has been determined that such enzymes, when incorporating fluorescently labeled nucleotides under excitation illumination, can suffer from substantial inactivation as a result of photodamage. In accordance with the subtractive aspects of the present invention, by subjecting enzymes at the upper surface of a waveguide substrate to prolonged illumination during nucleic acid synthesis in the presence of fluorescently labeled nucleotides or nucleotide analogs, one can effectively inactivate those molecules. As with the activation/inactivation based additive approaches described above, it will be appreciated that damaging illumination would not penetrate to the bottom surface, or area of interest, of the ZMW, and thus, such enzymes present at these locations would remain active. Fluorophore mediated inactivation of polymerases is discussed at length in commonly assigned U.S. patent application Ser. No. 11/293,040, filed Dec. 2, 2005 (now issued as U.S. Pat. No. 7,998,717), and incorporated herein in its entirety for all purposes. Other enzyme/fluorescent substrate pairs would be expected to yield similar characteristics, e.g., ATP binding proteins/fluorescently labeled ATP. Additionally, other components may be employed that generate radicals upon irradiation, that will damage those molecules that are within diffusive contact. By illuminating the upper surface of a waveguide structure in the presence of such compounds, for example, one could generate oxygen or other free radicals, that will deactivate molecules of interest within diffusive reach of such compounds. A variety of such compounds are known in the art and include, e.g., methylene blue, hypocrellin A, hypocrellin B, hypericin, Rose Bengal Diacetate, Merocyanine 540, and other dyes available from, e.g., Invitrogen/Molecular Probes (Eugene, Oreg.).

Figure 10:
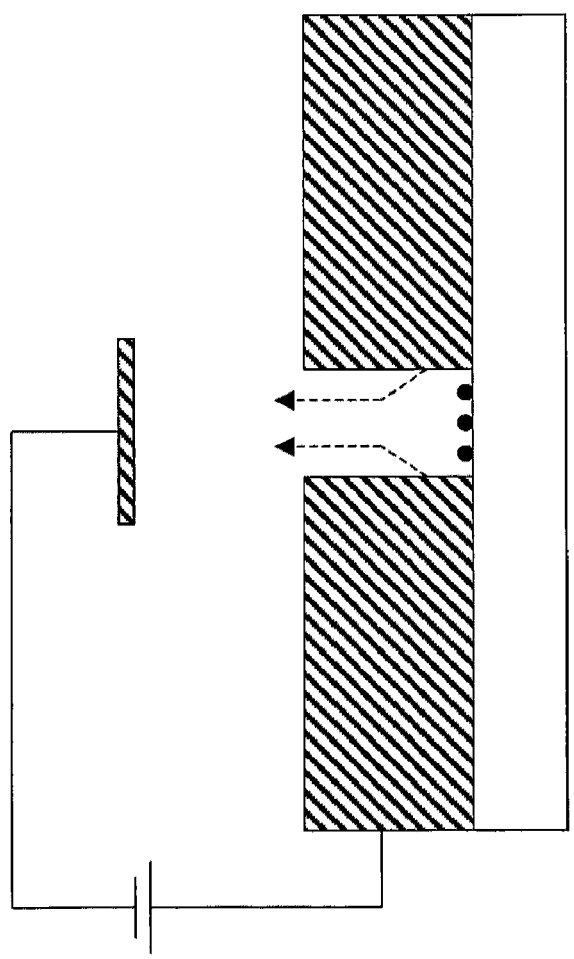
FIG. 10 illustrates selective immobilization of molecules of interest using an electrically driven system.

In another aspect of the invention, the structural characteristics of a substrate may be actively employed in subtractively selecting molecules of interest. In particular, substrates including optical confinements, such as ZMWs, typically include a metal layer deposited upon a transparent layer, e.g., glass or quartz, through which the waveguides are disposed, exposing the transparent substrate at the bottom surface of the waveguide. In accordance with the invention, an overall substrate that includes molecules of interest both coupled to the metal layer and the glass layer may be selectively partitioned, e.g., removing molecules of interest from the metal surfaces, by applying an electrical potential between the metal layer and the solution deposited over it, e.g., through the use of an electrode in contact with such fluid. Because the underlying substrate is not electrically conductive, the field between the surface of the substrate and the fluid will be substantially less than that between the metal layer and the fluid. The electrical potential may then be employed to selectively drive the molecules of interest from the metal surface and into solution (see FIG. 10). This driving force may be selected and/or controlled to result in electrophoretic forces, e.g., driving charged molecules of interest away from the surface in the non-desired surface regions or driving capping groups toward such surfaces, or alternatively or additionally, changes in the local environment at the metal surface, e.g., pH changes resulting from the generation of protons at the metal surface, that result in release from the surface, e.g., through the use of acid labile linkers, charge based linkages, e.g., hydrogen bonding, hydrolytic degradation of molecules of interest on the metal surfaces through the generation of locally harsh environments, or the like.

In another aspect, electrochemically releasable linker compounds may be employed to release molecules of interest from electrically active surfaces. By way of example, linking molecules that include electrochemically controllable coupling may be patterned upon the overall surface of a hybrid (metal/insulator) substrate. Applying a current through the metal portion of the surface results in release of the coupled molecule. Examples of such electrically switchable linkers include self assembled monolayers of biotin linked to quinone propionic ester bearing linker compounds, i.e., alkanethiolates on gold surfaces. Application of a potential to the underlying metal substrate results in reduction of the quinine to hydroquinone that rapidly undergoes lactonization with the release of the tethered molecule, e.g., biotin (See, e.g., Hodneland, et al., J. Am. Chem. Soc. 2000, 122:4235-4236).

In addition to the use of such methods in optical confinements, it will be appreciated that such electrophoretic and/or electrochemical selection and immobilization processes may be similarly applied to other hybrid analytical substrate types, including, e.g., metal or semiconductor based sensors that rely on surface associated molecules of interest, e.g., ChemFETS (chemical field effect transistors), and the like. In particular, the metal or semiconductor sensor element may be employed as one electrode in the repulsion or attraction of different groups from or to the surface of the sensor to enhance coupling.

Other subtractive processes may employ lift-off methods where an otherwise active surface is coated with a lift-off layer that entrains the molecules of interest on the upper surface of the substrate, and in some cases penetrating a certain distance into a ZMW. Lifting off of the layer brings the entrained molecules of interest with it, allowing those not entrained, e.g., those at the bottom surface of the ZMW, to remain.

Figure 11:
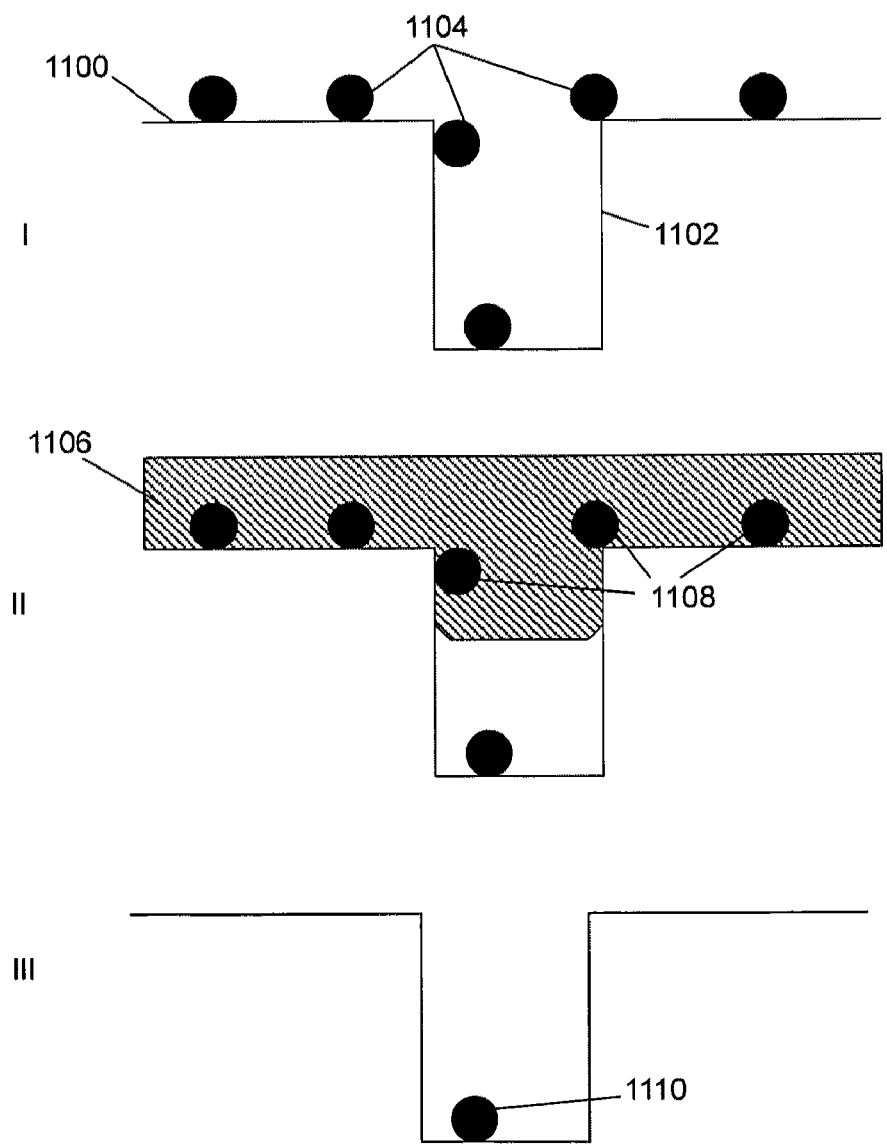
FIG. 11 I-III schematically illustrates a process for removal of molecules from non-relevant surfaces of substrates using an entraining matrix followed by a lift-off, technique.

This technique is schematically illustrated in FIG. 11. As shown, a uniform or random distribution of molecules of interest 1104 is deposited over a substrate 1100 that includes selected regions where such molecules are desired (Step I). In the case of FIG. 11, such areas include optical confinements like ZMWs 1102. A coating layer 1106 is then deposited over the surface as a viscous liquid, e.g., having a viscosity of 1 or greater (Step II). Because of its relative viscosity and the relatively small dimensions of the waveguides 1102, and/or the material's relatively slow diffusion in a liquid material present in the waveguide core, the coating layer 1106 will typically not flow completely into the waveguide structure. The coating layer is then typically allowed to cure, e.g., through air drying, heating or exposure to UV radiation, chemical crosslinking, entraining molecules of interest within the coating layer, e.g., molecules of interest 1108. Upon removal, any molecules of interest entrained in the coating layer are removed as well, leaving only those molecules of interest that were well within the waveguide structure, e.g., molecules 1110 (Step III). Although the above described method relies upon the limited ability of the coating layer to penetrate the waveguide structure to leave molecules of interest within such structures, it will be appreciated that such methods may be applied in the absence of such constrained structures. For example, the coating layer may be selectively patterned upon the surface, e.g., through screening or ink jet printing methods, to entrain and remove molecules of interest from selected regions.

Another subtractive, selective immobilization process relies generally upon masking strategies to ensure localization of the molecule of interest where desired. In particular, such masking strategies typically utilize a masking layer that may be either removed to eliminate molecules of interest from undesired locations, or which is deposited over a uniformly distributed population of the molecules of interest to render those in undesired locations inaccessible to the desired operation.

Other simpler brute force techniques are also within certain aspects of the invention, particularly related to subtractive processes. For example, one may use simple ablative processes to remove coupling groups from exposed surfaces, e.g., surfaces upon or near the upper surfaces of waveguide array substrates. Removal of such groups would be expected to reduce the amount of molecules of interest that are bound to surfaces outside of the waveguide structure. Such ablative processes include, e.g., laser ablation techniques, high sheer fluid ablation techniques, mechanical abrasion techniques, and the like that will remove materials upon contact or exposure. By directing such ablative processes at the upper surfaces, it is expected that little or none of the ablative forces will propagate into waveguide structures. Additional adjustments may be made to further enhance the selectivity of the process. For example, using laser ablation techniques, one could direct the beam at an oblique angle to the upper surface of the substrate, thereby penetrating only a minimal distance into high aspect ratio recesses, e.g., ZMWs. Likewise, ablation energy could be modulated to focus on regions that did not include the regions where eventual coupling of molecules of interest is desired, e.g., focused upon substrate surface regions or spaces between ZMWs in an array.

Once the coupling groups have been provided upon the surface of the substrate, e.g., in the desired regions such as at the bottom surface of a ZMW, the molecules of interest are then coupled to those active groups. As noted elsewhere herein, coupling may be via functional chemical groups, e.g., hydroxyl groups, amino groups, epoxy groups or the like. Alternatively, coupling may occur through specific binding partners, e.g., where one member of a specific binding pair is the coupling group attached to the surface (or is attached to a coupling group that is attached to the surface), and the other member of the binding pair is attached to or is integral with the molecule of interest. In particularly preferred aspects, such specific binding pairs are used to couple the molecule of interest to the surface, including, e.g., the use of avidin, streptavidin or neutravidin as one member of the binding pair, and biotin as the other member. Additionally, sandwich binding strategies may be employed, e.g., coupling biotin to the surface in the area of interest, followed by linkage to avidin, which is in turn, linked to a biotin molecule coupled to the molecule of interest. Typically, a linker silane group is used as the initial functional group. This group may be provided directly upon the surface or, as alluded to previously, diluted with similar linker silanes that are inert to additional coupling. In particularly preferred aspects, a linker silane bearing, e.g., a biotin group is immobilized in the initial step, followed by coupling of a molecule of interest, e.g., a polymerase enzyme, through a bridging avidin group coupled with an enzyme linked biotin group. As will be appreciated any of a variety of different configurations may be practiced within the context of the invention.

In the case of molecules of interest that are enzymes or otherwise active proteins, the orientation of immobilization may be an important characteristic to optimizing activity of the enzyme. For example, in the case of DNA polymerases, random adsorption of polymerases to a surface can yield substantially less than 100% activity at least partially as a result of some molecules being oriented in a way so as to prevent them from exhibiting optimal activity. As such, it may be desirable to provide for a specific orientation of the molecule by providing an anchoring group or groups on the molecule to increase the probability of correct orientation. Such methods have been previously described in commonly owned U.S. Patent Application No. 60/753,446, filed Dec. 22, 2005 (now expired), and incorporated herein by reference in its entirety for all purposes. Alternatively, one may provide the enzyme with a substrate molecule or substrate proxy that can prevent surface adsorption in a manner that blocks the active site of the enzyme. By way of example, it has been determined that immobilization of nucleic acid polymerase enzymes, such as DNA polymerases, in the presence of template nucleic acid molecules yields substantially higher activity of surface immobilized polymerases. Without being bound to a particular theory of operation, it is believed that the presence of the template molecule within the active site of the polymerase prevents immobilization of the polymerase in a manner that interferes with the active site, due to steric or other interference from the associated template. While template nucleic acid molecules can be used, other template-like molecules may also be used, including, e.g., LNA polymer strands, PNA polymers, or other nucleic acid analogs.

IV. Examples

Example 1

Photoactivatable Groups for Selective Immobilization of DNA Polymerases

A substrate may be used that includes a glass substrate layer with an aluminum cladding layer deposited over the glass layer. An array of ZMW cores is fabricated into the cladding layer to provide apertures through the cladding layer to the glass substrate. The overall substrate is optionally further treated to provide a thin insulating layer over the cladding layer and cores, e.g., to provide a substantially uniform surface. Such layers typically include $SiO_2$ coatings applied by vapor deposition techniques, including, e.g., CVD and MVD methods, as well as other methods such as fluid deposition or in situ formation using, e.g., spin on glass systems. The substrate surface is derivatized to first provide a relatively uniform population of amino terminated groups coupled to the surface. For example, for glass surfaces, such derivatization typically employs standard aminosilane chemistries known in the art. Alternatively, amine groups may be provided upon a linker molecule that is coupled to the surface through existing hydroxyl groups or surfaces otherwise derivatized. Such coupling groups may be provided at limited densities in order to further control the density of the molecules of interest that will ultimately be bound to the surface (see, e.g., commonly assigned U.S. patent application Ser. No. 11/240,662, filed Sep. 30, 2005 (now issued as U.S. Pat. No. 7,763,423), incorporated herein by reference in its entirety for all purposes).

Biotin molecules capped with an appropriate photolabile protecting group, such as MeNPOC, are then coupled to the derivatized surface using known chemistries, e.g., through an included epoxy group on the biotin molecule.

Following washing of the surface, appropriate illumination radiation is directed at the substrate through the transparent glass substrate layer, illuminating and deprotecting only the biotin groups at or near the bottom surface of the ZMW. DNA polymerase enzyme linked to avidin, streptavidin or neutravidin is then contacted with the substrate and selectively binds with the exposed biotin at the bottom of the waveguides.

In a second exemplary process, a photoactivatable acid group, e.g., surface coupled α-methylphenacyl ester, is coupled to the surface in the same fashion provided above. Illumination, e.g., at 313 nm, through the ZMW yields the acid groups at the bottom surface of the waveguides, which are then contacted with amino biotin groups followed by coupling to avidin linked polymerase enzymes, to yield enzyme groups only at or near the bottom surface of the waveguide.

Example 2

Selective Digestion of DNA Polymerase Enzymes Using Bead Bound Proteases

ZMWs that had previously been plasma treated in the presence of a PDMS gasket (to provide a priming layer), were provided with $\Phi29^{N62D}$ DNA Polymerase (complexed with a circular template nucleic acid) substantially uniformly surface adsorbed over the entire surface of the array, including upon the upper surface of the cladding layer.

The array was then contacted with beads bearing immobilized Proteinase-K (Sigma Chemical Co., P0803 or P9290) for 5 minutes at room temperature in 25 mM Tris-HCl, pH 7.5, 10 mM β-mercaptoethanol, 1 mM EDTA. The bead diameter far exceeded the nominal diameter of the waveguide cores on the array, preventing entry to the bead or its associated protease molecules into the cores to any substantial degree.

Polymerization reaction mixture including four dNTPs was then contacted with the array under conditions suitable for DNA synthesis (50 mM Tris-HCl, pH 7.5, 75 mM KCl, 20 mM $(NH_4)_2SO_4$, 10 mM β-mercaptoethanol, 0.7 mM $MnCl_2$), and synthesis was allowed to proceed for 30 minutes at 30° C.

Figure 12:
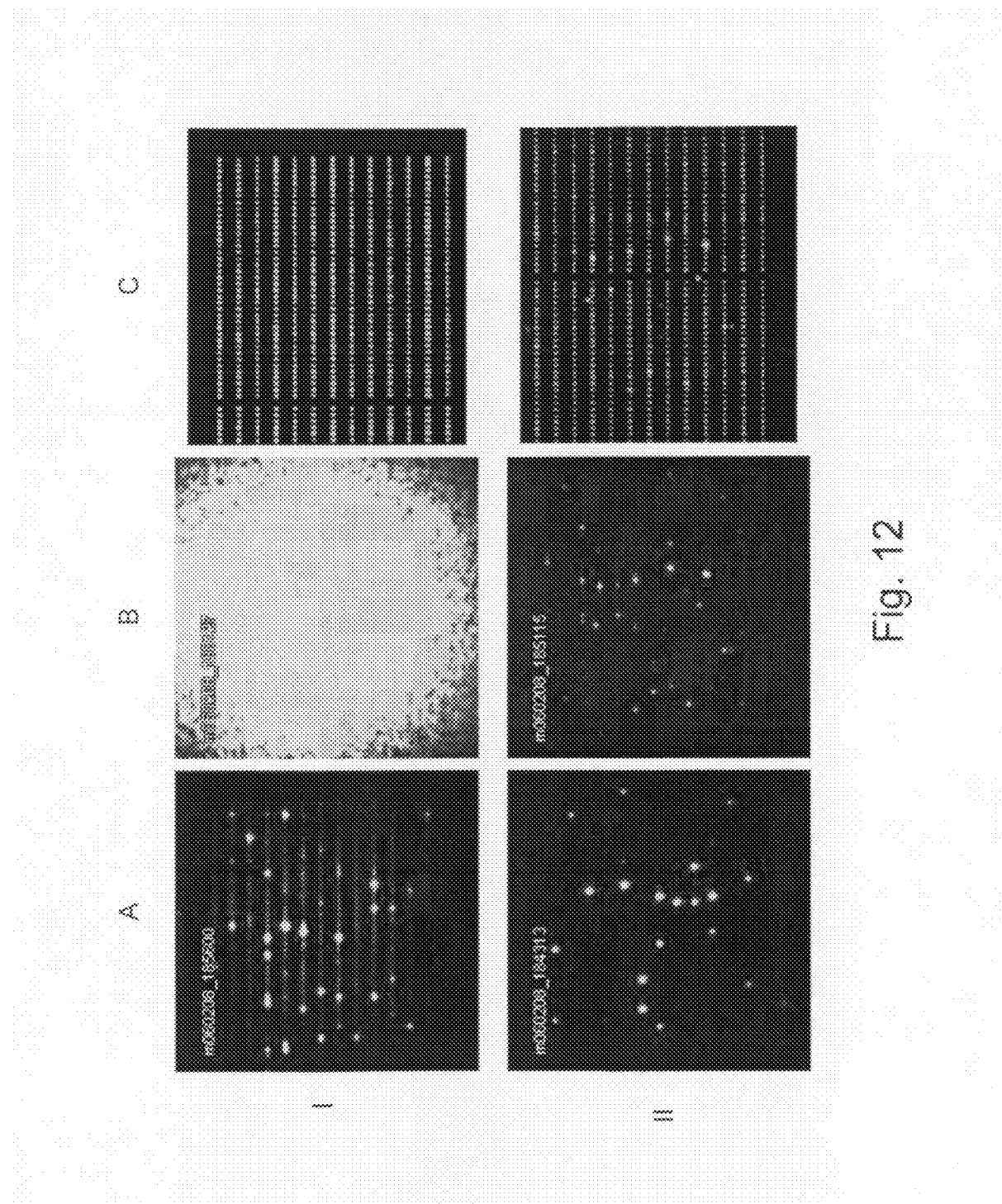
FIG. 12 IA-C, IIA-C illustrates the effects of selective immobilization processes of the invention and particularly using a size excluded particle process.

Following synthesis any synthesized DNA on the array was stained with SybrGold stain. The array was then imaged using a standard fluorescence microscope. The array images, as well as images of the negative control experiment, are shown in FIG. 12. As shown in the negative control (Row I), bottom side illumination (Column A) shows the presence of a significant amount of DNA within the waveguide structures, while top side illumination and observation (Column B) shows a uniform layer of DNA produced over the entire surface of the array. In the proteinase treated array (Row II), both the bottom side (Column A) and top side (Column B) show a similar pattern of DNA presence within specific waveguides. Further, as can be seen, there is little DNA present upon the upper surface other than within waveguides in the array, showing a substantial reduction from the high level of DNA synthesis present in the control experiment. Also of note is that the waveguides showing DNA presence from the upper surface track to the same waveguides showing DNA presence from the lower surface, indicating that DNA synthesis is occurring within the waveguide structure, and not outside the waveguide core. This also indicates that DNA being synthesized within the waveguide structure is of substantial length, e.g., greater than 500 bases, potentially up to 1000 or more bases in length, as it spans the illumination regions at the top and bottom portions of a waveguide structure having a core region of approximately 70 nm in diameter and 100 nm deep.

DNA synthesis experiments were also carried out in the presence of labeled nucleoside polyphosphate analogs, labeled at the terminal phosphate group (see, e.g., U.S. Patent Application Publication No. 2003-0044781 and Levene, et al., Science (2003) 299:609-764, the full disclosures of which are incorporated herein in their entirety for all purposes). These assays indicated substantially better signal to noise ratios than waveguide arrays that were not proteinase treated, showing markedly less interference from other noise sources, e.g., labeled by products of the polymerase reaction. As a result, it appears clear that provision of molecules of interest such as polymerase enzymes only within a desired region of an analytical substrate, i.e., an observation region, can have profoundly beneficial results on the application to which the substrate is to be put.

The following sets forth a series of experiments that demonstrate selective immobilization of a DNA polymerase on the bottom surface of ZMWs and passivation of the remaining ZMW surfaces with a polyelectrolyte multilayer. The process, which exploits the differential reactivity of silanes with glass and aluminum oxide, is schematically illustrated in FIG. 18. PEG-biotin silanization is specific to glass under the conditions employed, thereby resulting in chemical derivatization of only the ZMW bottom surface. The aluminum layer is then passivated using a polyelectrolyte multilayer, in this example, a 2.5× multilayer of PAA/PEI/PAA/PEI/PAA (where PAA is poly(acrylic acid) and PEI is poly(ethyleneimine)). Biotin tagged polymerase is rejected by the polyelectrolyte multilayer but binds to the biotinylated PEG surface via avidin chemistry, thereby resulting in biased immobilization of the polymerase to the bottom surface of the ZMW. In addition, the polyelectrolyte multilayer limits nonspecific binding of nucleotide analogs to the aluminum layer.

Biased immobilization of polymerase on the bottom surface of ZMWs was accomplished as follows. ZMW chips are cleaned in an oxygen plasma for 2 minutes at 2 torr (medium power setting). The PEG-Biotin silanization is carried out for 3 hours at 4° C. using a mixture of PEG methoxy silane and Biotin-PEG silane (Polymer Source Inc.) in 270:1 (w/w) ethanol:methanol solvent. The samples are rinsed with methanol, sonicated for 3 minutes in hot (70° C.) water, and washed with cold water. The polyelectrolyte procedure consists of consecutive immersion of the chips for 5 minutes at room temperature in 20 mg/ml Polyacrylic acid and Polyethylenimine (Sigma-Aldrich, pH 7.5 adjusted with HCl), each step followed by 3× rinsing with water, in the order: PAA/PEI/PAA/PEI/PAA. The last wash is with 5 volume equivalents of water.

Figure 19:
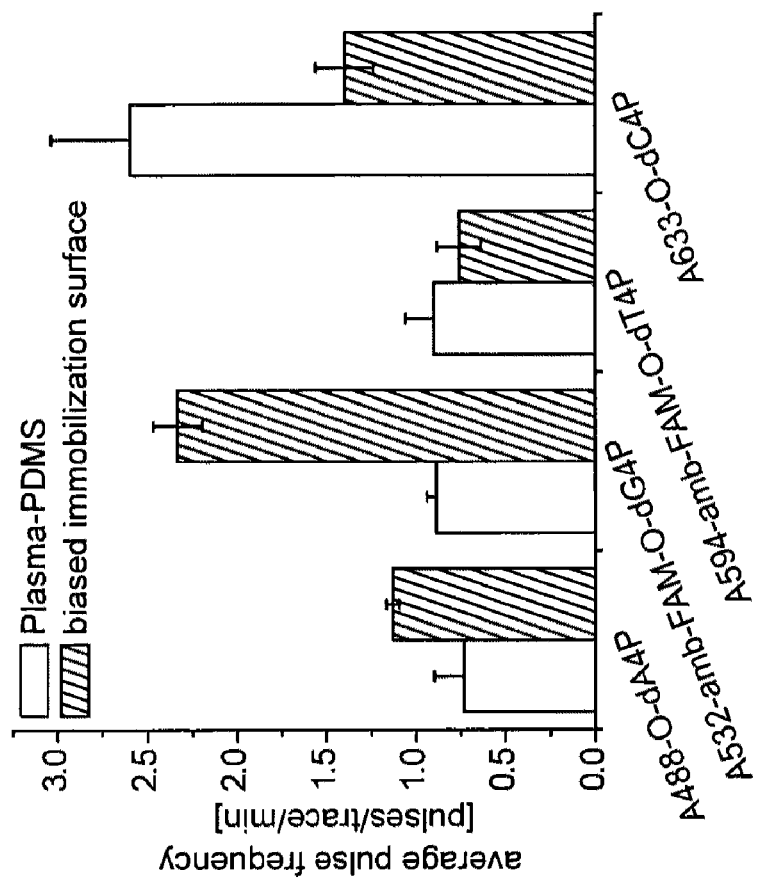
FIG. 19 illustrates binding of nucleotide analogs to a polyelectrolyte multilayer-treated versus a plasma-PDMS treated (non-biased treated) surface.

Nonspecific binding of four nucleotide analogs to the biased immobilization surface (ZMW chip treated with the mixture of PEG-silanes followed by polyelectrolyte multilayer formation) and to a control surface (a plasma-PDMS treated chip) was compared (FIG. 19). The plasma-PDMS treatment used on the control chip removes bias because it coats the entire structure with a uniform layer; see International Application Number PCT/US 2006/045,429 filed Nov. 27, 2006. Chips were incubated with a mixture of fluorescently labeled nucleotide analogs (A488-dA4P, FAM-A532-dG4P, FAM-A594-dT4P, A633-dC4P, 5 µM each; see, e.g., U.S. patent application Ser. No. 11/645,223 for analog nomenclature), and subjected to laser illumination. Movies were acquired for 1 minute at 100 fps camera speed. Fluorescence traces were analyzed by a custom-build analysis software, using a threshold algorithm to determine the number of non-specific adsorption events shown in the graph for each, spectrally separated analog. As shown in FIG. 19, the biased immobilization surface is as good at preventing nonspecific analog binding as is the plasma-PDMS surface (which exhibits good nonspecific binding characteristics). Analog binding to an untreated surface was not quantified, since the analogs bind the untreated surface to such an extent that single pulses cannot be identified.

Figure 20I:
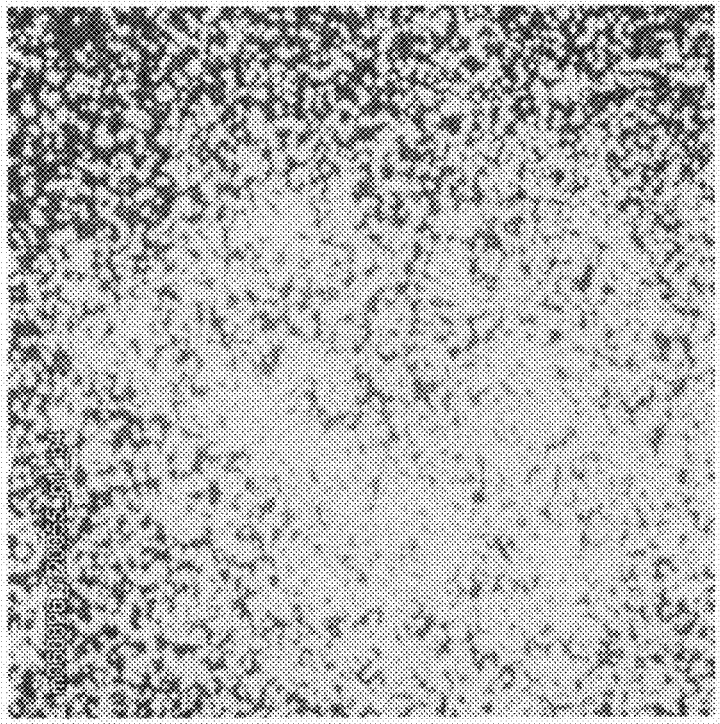
FIG. 20 I and II illustrates binding of polymerase to a polyelectrolyte multilayer-treated versus an untreated aluminum surface.
Figure 20I:
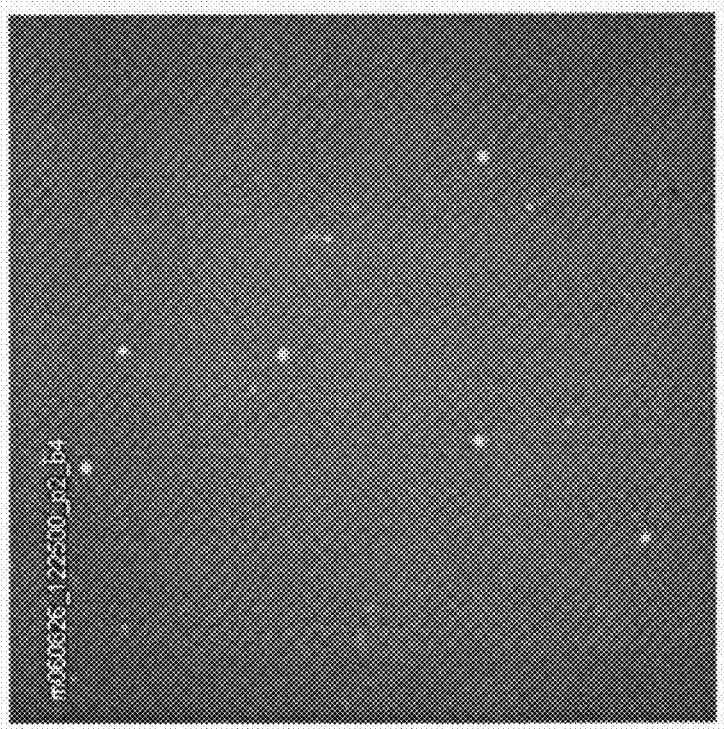

Polyelectrolyte multilayer deposition on an aluminum surface inhibits nonspecific binding of polymerase, as illustrated in FIG. 20. Essentially no DNA synthesis is observed on the aluminum surface treated with a 2.5×PAA/PEI/PAA/PEI/PAA polyelectrolyte multilayer (Panel I), while DNA is produced over the entire surface of a control surface not treated with the polyelectrolyte multilayer (Panel II). Polymerization reactions were carried out as follows: 100 nM polymerase was bound to Neutravidin (present in excess at 150 nM) in a BF-300 buffer containing 25 mM Tris-acetate, pH 7.5, 300 mM potassium acetate, 0.05% Tween 20 and 5 mM dithiothreitol for 30 minutes at 4° C. The solution was diluted to an effective potassium acetate concentration of 150 mM by 2-fold dilution with the same buffer as above but lacking potassium acetate (BF-0). The polymerase/Neutravidin mixture was incubated for 30 minutes at 4° C. on the ZMW chip, and washed 3× with BF-150 buffer (the same buffer as BF-300 but including 150 mM potassium acetate). Template at 100 nM was added for 20 minutes at 4° C., in reaction buffer (50 mM Tris acetate, pH 7.5, 75 mM potassium acetate, 20 mM ammonium sulfate, 0.05% Tween 20 and 5 mM dithiothreitol) supplemented with 4 mM EDTA. Template solution was removed and the extension reaction mixture was added, containing 0.7 mM $MnCl_2$, 10 µM of each dATP, Alexa Fluor ChromaTide 488-dCTP (Invitrogen), dGTP and dTTP in reaction buffer. DNA synthesis proceeded for 10 minutes at room temperature, followed by 5× washing with BF-150 supplemented with 1 mM EDTA. ChromaTide nucleotide incorporation into DNA was visualized on a wide-field fluorescence microscope (Olympus), using a 60×0.9NA physiology objective lens to image the top (solution) side of the ZMW chips, and a 60×1.2NA objective lens for the bottom side.

Figure 21:
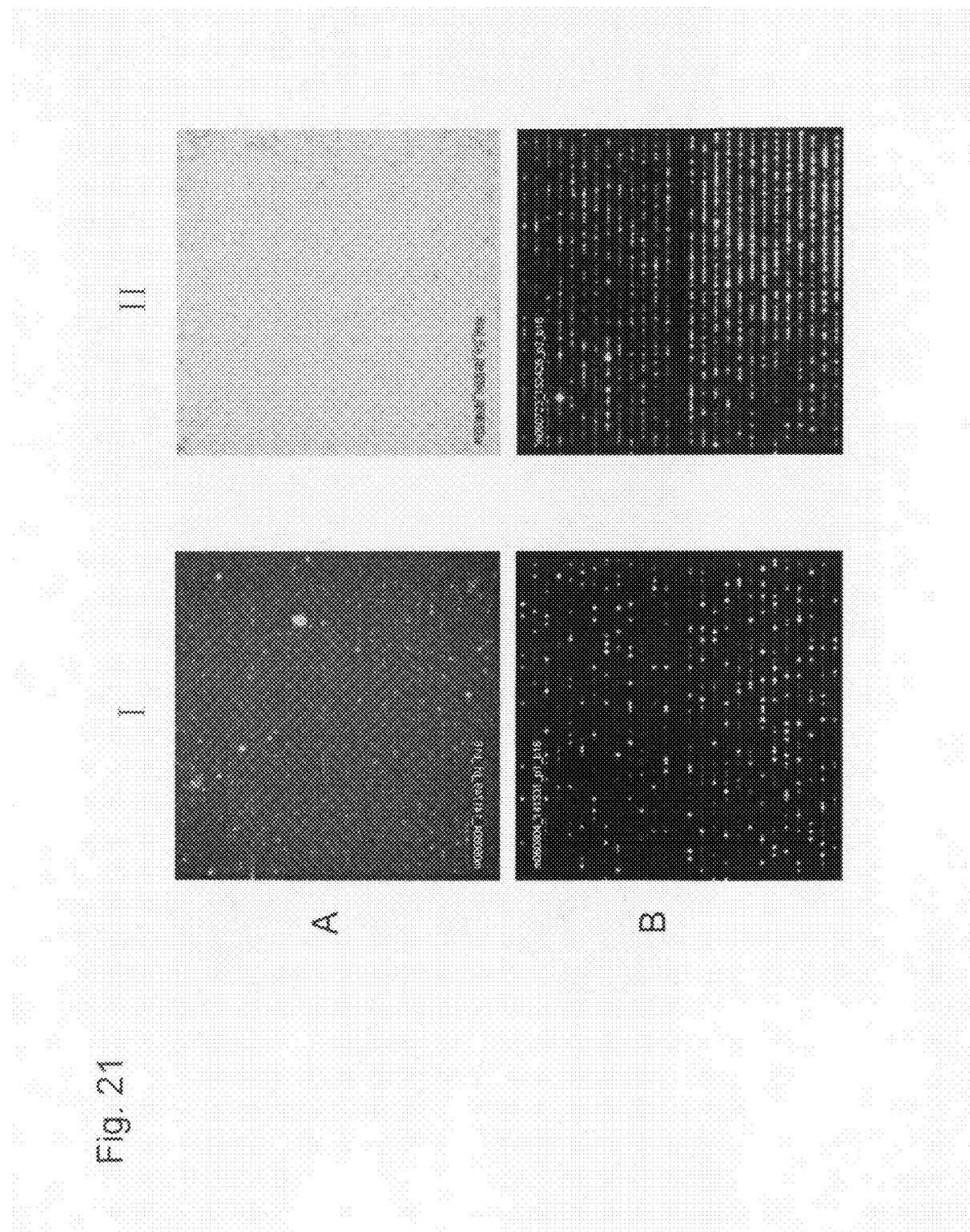
FIG. 21 IA-IIB illustrates the effects of selective immobilization processes of the invention and particularly using a selective silanization and polyelectrolyte multilayer passivation process.
Figure 22:
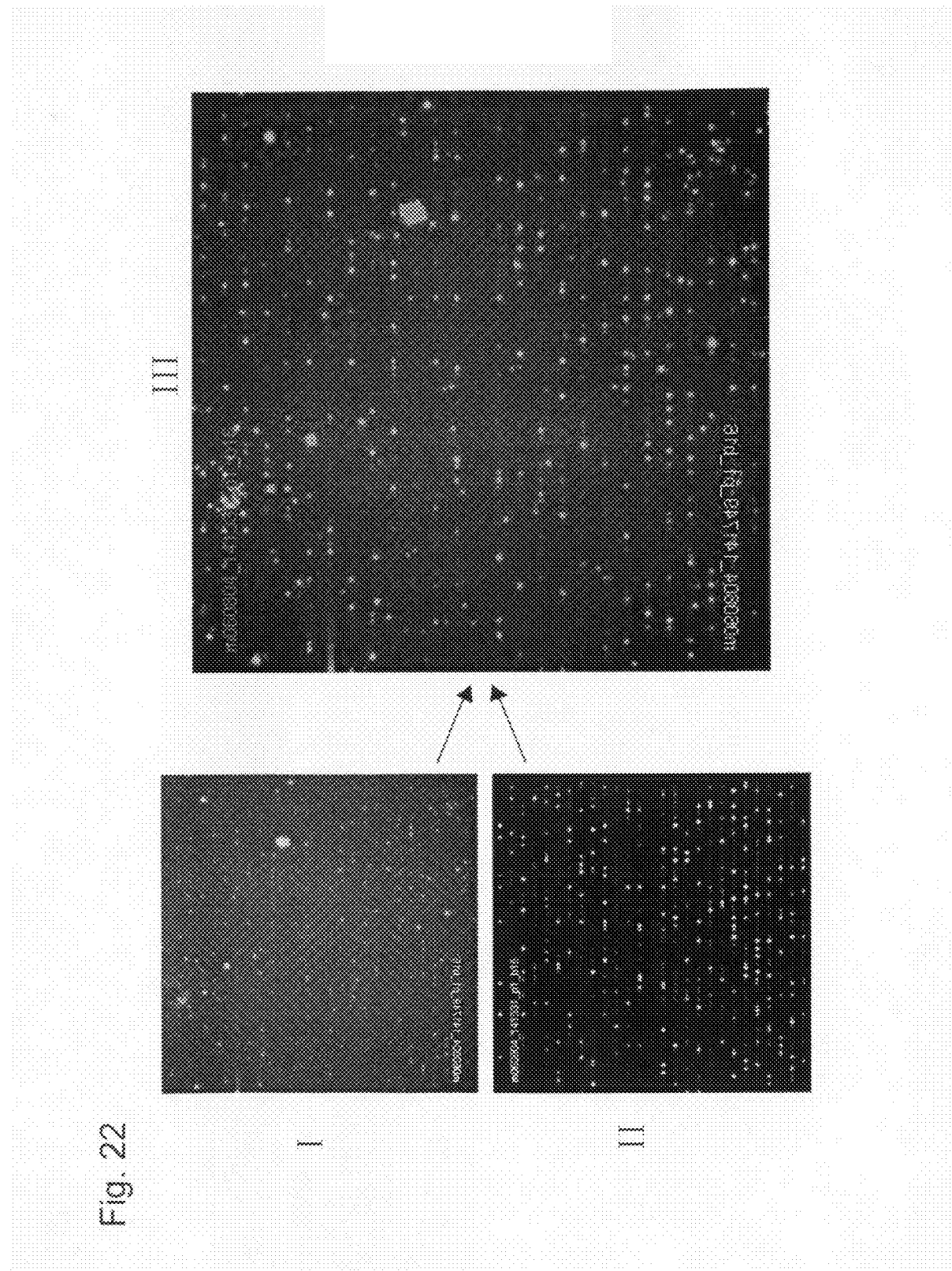
FIG. 22 I-III illustrates the effects of selective immobilization processes of the invention and particularly using a selective silanization and polyelectrolyte multilayer passivation process.

The biased immobilization procedure (treatment of the ZMW chip with the mixture of PEG-silanes followed by polyelectrolyte multilayer formation) results in selective immobilization of the polymerase within the waveguides. Polymerization reactions were carried out as described in the preceding paragraph on a biased immobilization ZMW chip and on a control ZMW chip (uniformly coated, with a plasma-PDMS layer underneath followed by PEG-methoxy/Biotin-PEG silane derivatization). Images of the biased immobilization ZMW array, as well as images of the control array, are shown in FIG. 21. As shown in the control (Column II), bottom side illumination (Row B) shows the presence of a significant amount of DNA within the waveguide structures, while top side illumination (Row A) shows a uniform layer of DNA produced over the entire surface of the array. For the biased immobilization ZMW array (Column I), in contrast, both the bottom side (Row B) and top side (Row A) show a similar pattern of DNA presence within specific waveguides. Further, as can be seen, there is little DNA present upon the upper surface other than within waveguides in the array, showing a substantial reduction from the high level of DNA synthesis present in the control experiment. Also of note is that the waveguides showing DNA presence from the upper surface track to the same waveguides showing DNA presence from the lower surface, indicating that DNA synthesis is occurring within the waveguide structure, and not outside the waveguide core; see FIG. 22, in which an image of the top surface of a biased immobilization ZMW array (Panel I) and an image at the bottom surface of the same array (Panel II) are overlaid (Panel III).

These results indicate that the polyelectrolyte multilayer is relatively non-sticky to nucleotide analogs and that the polyelectrolyte multilayer passivates well against polymerase binding to aluminum surfaces. Differential PEG-biotin-silane chemistry, followed by polyelectrolyte multilayer passivation, yields biased immobilization of the polymerase with high contrast.

Example 4

Selective Immobilization and Passivation Using a Phosphonic Acid

Deposition of polyvinylphosphonic acid (PVPA) onto untreated ZMWs results in a ZMW that is passivated from nonspecific protein (e.g., neutravidin and polymerase) and nucleotide analog binding to the aluminum surface. PVPA is specific to aluminum and does not affect the $SiO_2$ bottom surface of the ZMW, which can be used for nonspecific capture agent or polymerization immobilization or subsequent derivatization (e.g., by silanization or binding of compounds such as PLL-PEG) for specific polymerase deposition.

Figure 23:
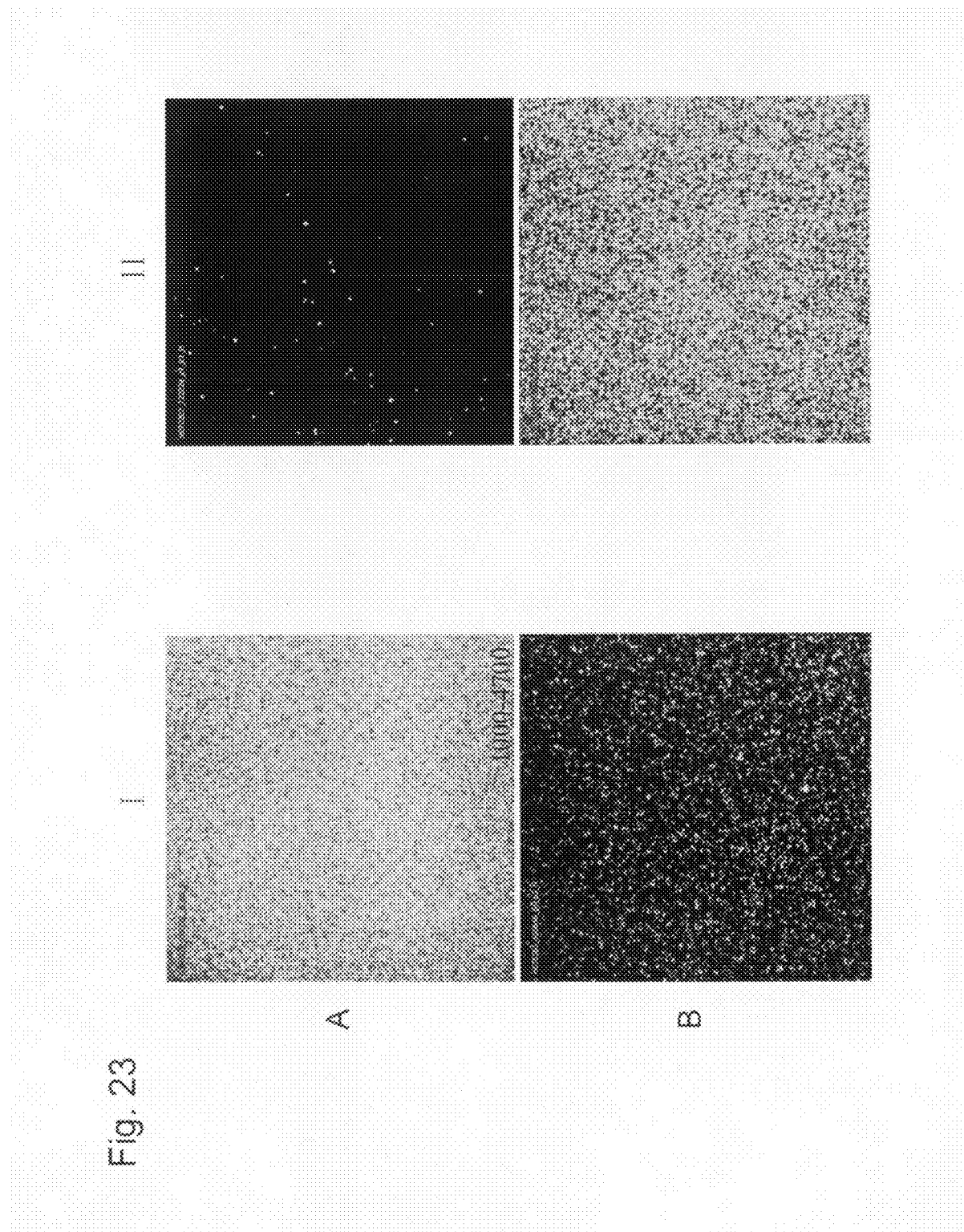
FIG. 23 IA-IIB illustrates binding of neutravidin-coated fluorescent beads to a phosphonate-treated ZMW versus an untreated ZMW.

Treatment of a mixed material substrate (e.g., 100 nm aluminum film on glass) with PVPA results in immobilization of a neutravidin capture agent preferentially on the $SiO_2$, rather than the aluminum, portion of the substrate, as illustrated in FIG. 23. On a substrate not treated with PVPA, more neutravidin is deposited on the aluminum portion of the substrate (Panel I Row A) than on the $SiO_2$ portion (Panel I Row B). On a PVPA-treated substrate, in contrast, neutravidin is immobilized preferentially on the $SiO_2$ portion of the substrate (Panel II Row B), while little neutravidin sticks to the aluminum portion of the substrate (Panel II Row A).

To assess neutravidin binding, chips are cleaned from a protective photoresist layer by first rinsing them in acetone, followed by rinsing in isopropanol and drying with a stream of nitrogen. They are cleaned in a plasma cleaner (Harrick) for 2 minutes at 2 torr (medium power setting). PVPA treatment proceeds on a heat block set to 90° C., the chips are put on the heat block, and 90° C. PVPA solution (molecular weight 24,000, from Polysciences Inc. (Warrington, Pa.), 25% stock diluted to 2% working solution concentration in water) is put on the chip for 2 minutes, followed by rinsing with water. Excess water is blown away by a stream of nitrogen, followed by heat treatment for 10 minutes at 80° C. in a dry oven. 40 nm A488-Neutravidin latex beads (Invitrogen) are diluted to 0.01% in buffer (50 mM MOPS-acetate, pH 7.5, 75 mM potassium acetate, 5 mM DTT) and incubated with the chips for 15 minutes at room temperature. The chips are rinsed with water and imaged on a wide-field fluorescence microscope, using a 60×0.9 NA physiology objective lens (Olympus).

Figure 24:
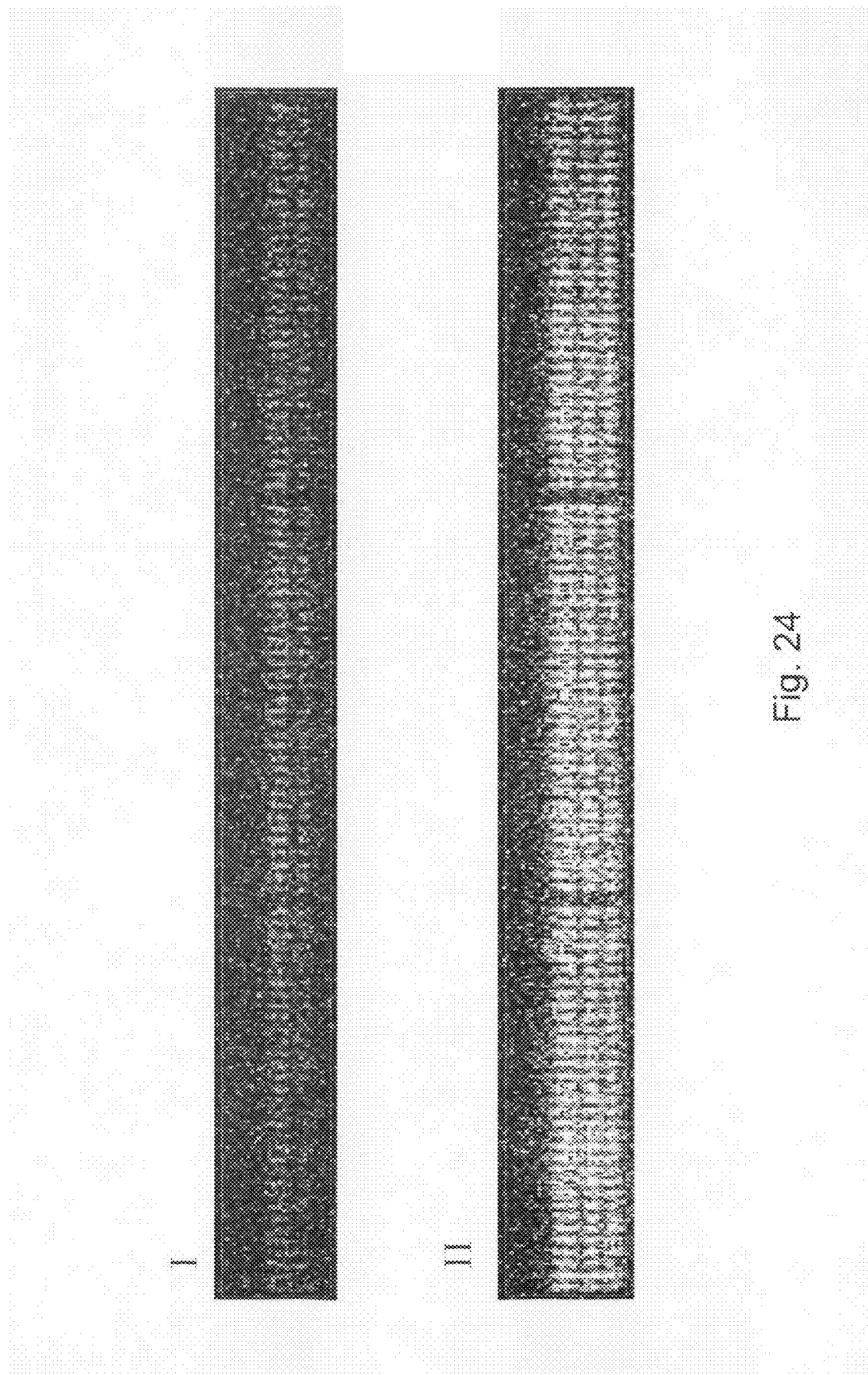
FIG. 24 I-II illustrates binding of nucleotide analogs to a phosphonate-treated ZMW versus an untreated ZMW.

PVPA treatment reduces nucleotide analog binding, as illustrated in FIG. 24. ZMW chips were treated with PVPA, and nonspecific binding of nucleotide analogs to the chips was analyzed as described above in Example 3. As shown in FIG. 24, the analogs exhibit considerable nonspecific binding to an untreated ZMW (Panel II), while little analog binding to a PVPA-treated ZMW is observed (Panel I).

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A method of selectively immobilizing an enzyme on a substrate, comprising:
    providing a substrate having a first surface component and a second surface component where the first and second surface component have different surface characteristics, wherein the substrate comprises a layer of the second surface component on a layer of the first surface component, and wherein the substrate comprises a zero mode waveguide disposed through the second surface component layer to the first surface component layer and exposing a portion of the first surface component layer, the portion of the first surface component layer thereby exposed forming a bottom reading surface of the zero mode waveguide;
    contacting the substrate with a first composition that selectively associates with the first surface component and coupling the enzyme to the first composition, thereby selectively coupling the enzyme atop the bottom reading surface in the zero mode waveguide; and
    contacting the substrate with a second composition that selectively associates with the second surface component, wherein the second composition comprises a compound comprising one or more phosphonic acid groups.

2. The method of claim 1, wherein the first surface component comprises $SiO_2$ and the second surface component comprises a metal or metal oxide.

3. The method of claim 1, wherein the differing surface characteristics comprise surface charge.

4. The method of claim 3, wherein the first surface component has a negative surface charge and the second surface component has a positive surface charge.

5. The method of claim 1, wherein the first composition comprises a first coupling group, and wherein selectively coupling the enzyme to the first composition comprises coupling the enzyme to the first coupling group.

6. The method of claim 5, wherein the first coupling group comprises biotin.

7. The method of claim 1, wherein the first composition comprises a silane.

8. The method of claim 7, wherein the first composition comprises a biotin-PEG-silane.

9. The method of claim 1, wherein the first composition comprises poly(L-lysine)-poly(ethylene glycol) or poly(L-lysine)-poly(ethylene glycol)-biotin.

10. The method of claim 1, wherein the second composition is polyvinylphosphonic acid.

11. The method of claim 1, wherein the second composition is selected from the group consisting of:

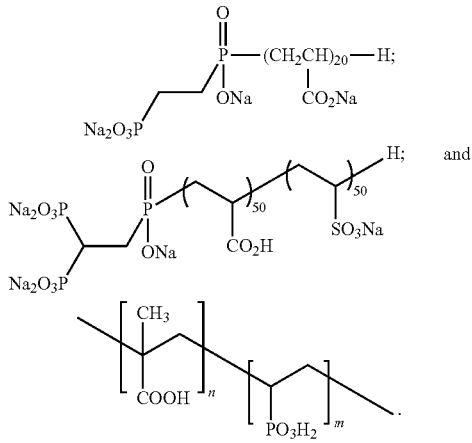

12. The method of claim 1, wherein the second composition is selected from the group consisting of: 2-carboxyethyl phosphonic acid; amino tri (methylene phosphonic acid); 1-hydroxyethylidene-1,1,-diphosphonic acid; hexamethylenediaminetetra(methylenephosphonic acid); diethylenetriamine penta(methylene phosphonic acid); ethylenediamine tetra(methylene phosphonic acid); bis(hexamethylene triamine penta(methylenephosphonic acid)); 2-phosphonobutane-1,2,4-tricarboxylic acid; and monoethanolamine diphosphonate.

13. The method of claim 1, wherein the second composition comprises an alkyl phosphonate.

14. The method of claim 1, wherein the second composition is selected from the group consisting of: octyl phosphonic acid, decyl phosphonic acid, dodecyl phosphonic acid, hexadecyl phosphonic acid, octadecyl phosphonic acid, docosyl phosphonic acid, hydroxy-dodecyl phosphonic acid, hydroxy-undecenyl-phosphonic acid, and decanediylbis (phosphonic acid).

15. The method of claim 1, wherein the second composition comprises a second coupling group.

16. The method of claim 1, wherein the enzyme comprises a polymerase.

17. The method of claim 1, wherein the substrate is contacted with the second composition and then contacted with the first composition.

18. A method of analyzing an enzyme that is selectively immobilized on a substrate, comprising:
  a) selectively immobilizing the enzyme on the substrate by:
    providing a substrate having a first surface component and a second surface component where the first and second surface component have different surface characteristics, wherein the substrate comprises a layer of the second surface component on a layer of the first surface component, and wherein the substrate comprises a zero mode waveguide disposed through the second surface component layer to the first surface component layer,
    contacting the substrate with a first composition that selectively associates with the first surface component and coupling the enzyme to the first composition, thereby selectively coupling the enzyme to the first surface component in the zero mode waveguide, and
    contacting the substrate with a second composition that selectively associates with the second surface component, wherein the second composition comprises a compound comprising one or more phosphonic acid groups; and
  b) after selectively immobilizing the enzyme on the substrate, providing illumination to and receiving electromagnetic radiation from an observation volume of the zero mode waveguide through the first surface component layer.

* * * * *